United States Patent
Shirasaka et al.

(10) Patent No.: US 8,594,402 B2
(45) Date of Patent: Nov. 26, 2013

(54) IMAGE DIAGNOSIS SUPPORT APPARATUS, METHOD AND PROGRAM

(75) Inventors: Hajime Shirasaka, Tokyo (JP); Keigo Nakamura, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 13/580,206

(22) PCT Filed: Mar. 2, 2011

(86) PCT No.: PCT/JP2011/001208
§ 371 (c)(1),
(2), (4) Date: Aug. 21, 2012

(87) PCT Pub. No.: WO2011/108262
PCT Pub. Date: Sep. 9, 2011

(65) Prior Publication Data
US 2013/0070984 A1 Mar. 21, 2013

(30) Foreign Application Priority Data

Mar. 5, 2010 (JP) .............................. 2010-049428
Aug. 30, 2010 (JP) .............................. 2010-192512

(51) Int. Cl.
*G06K 9/00* (2006.01)
(52) U.S. Cl.
USPC ...................................... 382/128; 382/154
(58) Field of Classification Search
USPC ......... 382/128, 131–132, 154, 173, 282–283; 378/4, 901; 600/407–411, 424–428; 345/419
See application file for complete search history.

(56) References Cited

U.S. PATENT DOCUMENTS 5,940,527 A 8/1999 Takeo
6,683,933 B2 * 1/2004 Saito et al. .................. 378/4
(Continued)

FOREIGN PATENT DOCUMENTS

JP 4-104380 4/1992
JP 8-215183 8/1996
(Continued)

OTHER PUBLICATIONS

Reinhard Beichel et al., "Liver Segment Approximation in CT Data for Surgical Resection Planning", Medical Imaging 2004: Image Processing, edited by J. M. Fitzpatrick; M. Sonka, Proceedings of the SPIE, vol. 5370, pp. 1435-1446, 2004.

(Continued)

Primary Examiner — Ishrat I Sherali
(74) Attorney, Agent, or Firm — Young & Thompson

(57) ABSTRACT

At least one specified position and, if necessary, a cutting surface are specified in a three-dimensional medical image. Plural anatomical structures present within a predetermined range from the specified position are extracted, as structures to be separated, by referring to a structure information storage unit that stores plural anatomical structures and a separation condition storage unit that stores a separation condition for each anatomical structure of a subject to determine, based on the specified position, a boundary surface and, if necessary, a cutting surface for separately displaying the plural anatomical structures. The boundary surface corresponding to the structures to be separated and the specified position and, if necessary, the cutting surface are set based on the separation condition. A three-dimensional medical image in which the structures to be separated are separated by the boundary surface and, if necessary, by the cutting surface is generated, and displayed.

12 Claims, 24 Drawing Sheets

(56) References Cited

U.S. PATENT DOCUMENTS

| | | | |
|---|---|---|---|
| 7,702,137 B2* | 4/2010 | Dwyer et al. | 382/128 |
| 7,738,701 B2* | 6/2010 | Matsumoto | 382/173 |
| 8,170,328 B2* | 5/2012 | Masumoto et al. | 382/154 |
| 8,199,984 B2* | 6/2012 | Mori et al. | 382/128 |
| 8,311,301 B2* | 11/2012 | Gindele | 382/128 |
| 8,355,775 B2* | 1/2013 | Oshiki et al. | 600/425 |
| 8,483,467 B2* | 7/2013 | Mizuno | 382/131 |
| 8,538,105 B2* | 9/2013 | Masumoto | 382/128 |
| 2002/0181754 A1 | 12/2002 | Masumoto et al. | |
| 2003/0095692 A1 | 5/2003 | Mundy et al. | |
| 2005/0010100 A1 | 1/2005 | Hornegger et al. | |
| 2005/0148852 A1 | 7/2005 | Tank | |
| 2009/0202122 A1 | 8/2009 | Wang | |
| 2011/0130653 A1 | 6/2011 | Wang | |

FOREIGN PATENT DOCUMENTS

| | | |
|---|---|---|
| JP | 10-097624 | 4/1998 |
| JP | 11-299782 | 11/1999 |
| JP | 2001-137230 | 5/2001 |
| JP | 2001-283191 | 10/2001 |
| JP | 2002-345807 | 12/2002 |
| JP | 2003-033349 | 2/2003 |
| JP | 2003-225231 | 8/2003 |
| JP | 2003-271924 | 9/2003 |
| JP | 2004-141612 | 5/2004 |
| JP | 2004-329929 | 11/2004 |
| JP | 2005-169120 | 6/2005 |
| JP | 2008-043564 | 2/2008 |
| JP | 2008-253293 | 10/2008 |
| JP | 4179661 | 11/2008 |
| JP | 2009-207886 | 9/2009 |
| JP | 2011-131040 | 7/2011 |

OTHER PUBLICATIONS

Daisuke Kobayashi et al., "Trial of Branch Base Tree Structure Model Construction for Blood Vessel Geometric Representation", [on line], Riken, Riken Symposium "Digitization and Database Construction Research of Organism Shape Information", pp. 84-92, 2005 [Search on Jan. 6, 2010], Internet URL:http//www.comp-bio.riken.jp/keijyo/products/2005_1_files/kobayashi_print.pdf.

Sho Nakamura et al., "Automated Classification of Pulmonary Artery and Vein from Chest X-ray CT Images by Tree Structure Analysis", Technical Research Report of the Institute of Electronics, Information and Communication Engineers, Technical Report of IEICE, vol. 105, No. 580, pp. 105-108, 2006 [Searched on Nov. 20, 2009], Internet URL:http//www.murase.nuie.nagoya-u.ac.jp/~ide/res/paper/j05-kenkyukai-snaka-1.pdf.

Yasushi Hirano et al., "Quantification of shrinkage of lung lobes in chest CT images using the 3D Voronoi division and application to tumor discrimination", [online], Proceedings of 20th Annual Meeting of the Japanese Society of Medical Imaging Technology, pp. 315-316, 2001 [Searched on Nov. 20, 2009] Internet URL:http://mase.itc.nagoya-u.ac.jp/~hirano/Papers/JAMIT2001.pdf.

K. Kubota et al., "Evaluation of Computer-Aided Diagnosis system for Lung Cancer based on Helical CT images", Technical Report of IEICE, vol. 101, No. 310, pp. 41-46, 2001.

Shoji Kido et al., "Intelligent CAD for diffuse lung diseases", Grant-in-Aid for Scientific Research, granted by the Ministry of Education, Culture, Sports, Science and Technology, Study in Specific Field, "Intellectual Diagnosis Aid of Multi-Dimensional Medical Image", Proceedings of 4th Symposium, pp. 45-54, 2007.

Yuki Wakida et al., "Liver Cancer Detection based on a Temporal Density Feature from Abdominal Dynamic X-ray CT Images", Proceedings of Journal of Computer Aided Diagnosis of Medical Image, vol. 10, No. 1, pp. 1-10, 2007.

Hiroshi Fujita et al., "Intelligent Computer-aided Diagnosis Based on Normal Structure Recognition of Human Body", Grant-in-Aid for Scientific Research, granted by the Ministry of Education, Culture, Sports, Science and Technology, Study in Specific Field, "Intellectual Diagnosis Aid of Multi-Dimensional Medical Image", Proceedings of 4th Symposium, pp. 55-60, 2007.

International Search Report PCT/JP2011/001208 dated Apr. 5, 2011, with English translation.

* cited by examiner

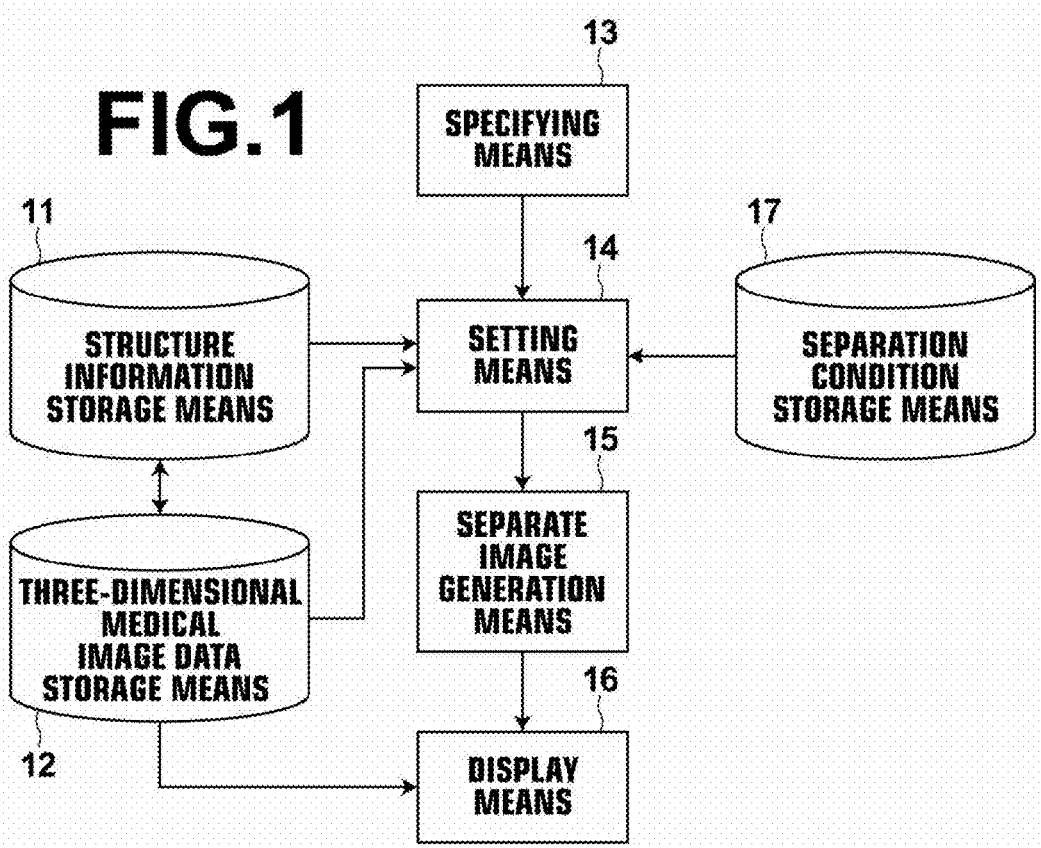
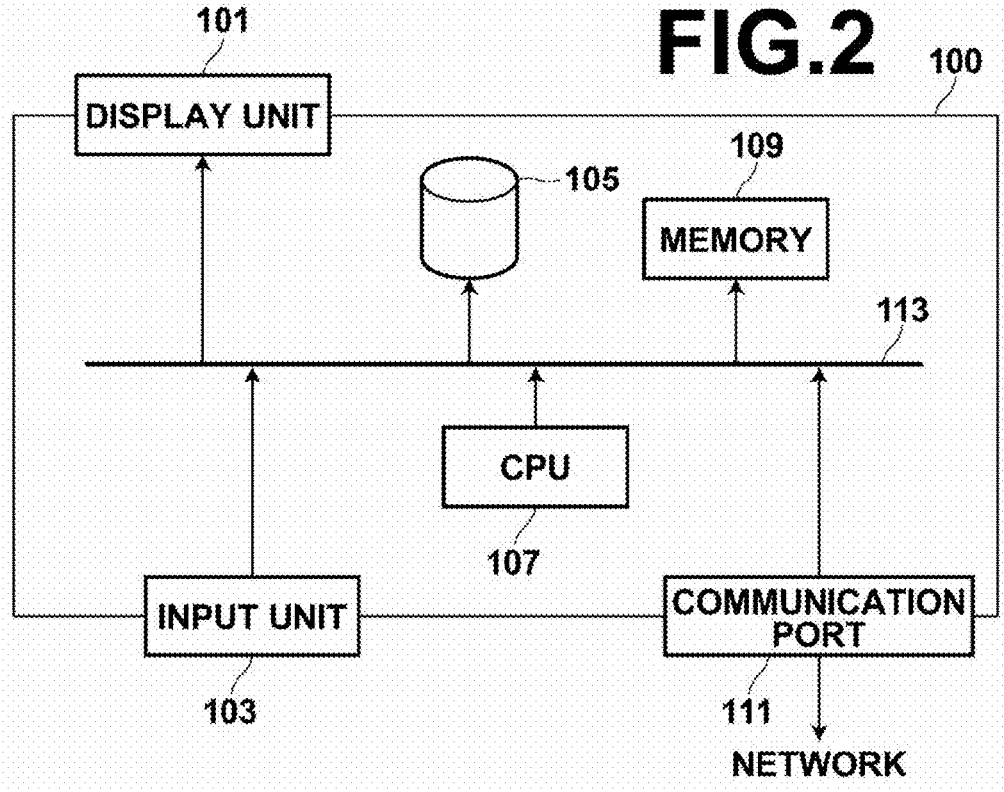

FIG.3

| ANATOMICAL STRUCTURE | BOUNDARY SURFACE / CUTTING SURFACE | MOVEMENT DIRECTION | MOVEMENT AMOUNT |
|---|---|---|---|
| RIGHT LOBE (LIVER) | CONTOUR | NOT SPECIFIED | 0 |
| LEFT LOBE (LIVER) | CONTOUR | DIRECTION PERPENDICULARLY AWAY FROM SPECIFIED SURFACE | $d_{37}$ |
| BLOOD VESSEL (LIVER) | CONTOUR | NOT SPECIFIED | 0 |
| RIGHT VENTRICLE (HEART) | CONTOUR | DIRECTION PERPENDICULARLY AWAY FROM SPECIFIED SURFACE | $d_{31}$ |
| RIGHT ATRIUM (HEART) | CONTOUR | DIRECTION PERPENDICULARLY AWAY FROM SPECIFIED SURFACE | $d_{32}$ |
| LEFT VENTRICLE (HEART) | CONTOUR | DIRECTION PERPENDICULARLY AWAY FROM SPECIFIED SURFACE | $d_{33}$ |
| LEFT ATRIUM (HEART) | CONTOUR | DIRECTION PERPENDICULARLY AWAY FROM SPECIFIED SURFACE | $d_{34}$ |
| SUBCUTANEOUS FAT | SPECIFIED SURFACE | DIRECTION PERPENDICULARLY AWAY FROM SPECIFIED SURFACE | $d_{51}$ |
| VISCERAL FAT | CONTOUR | NOT SPECIFIED | 0 |
| LARGE INTESTINE | CONTOUR | DIRECTION PERPENDICULARLY AWAY FROM SPECIFIED SURFACE | $d_{53}$ |
| SMALL INTESTINE | CONTOUR | DIRECTION PERPENDICULARLY AWAY FROM SPECIFIED SURFACE | $d_{54}$ |

~170

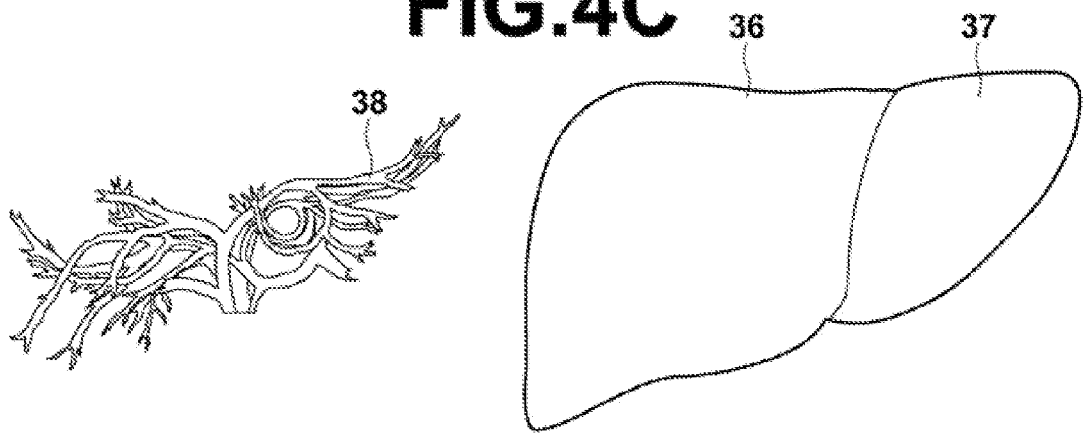
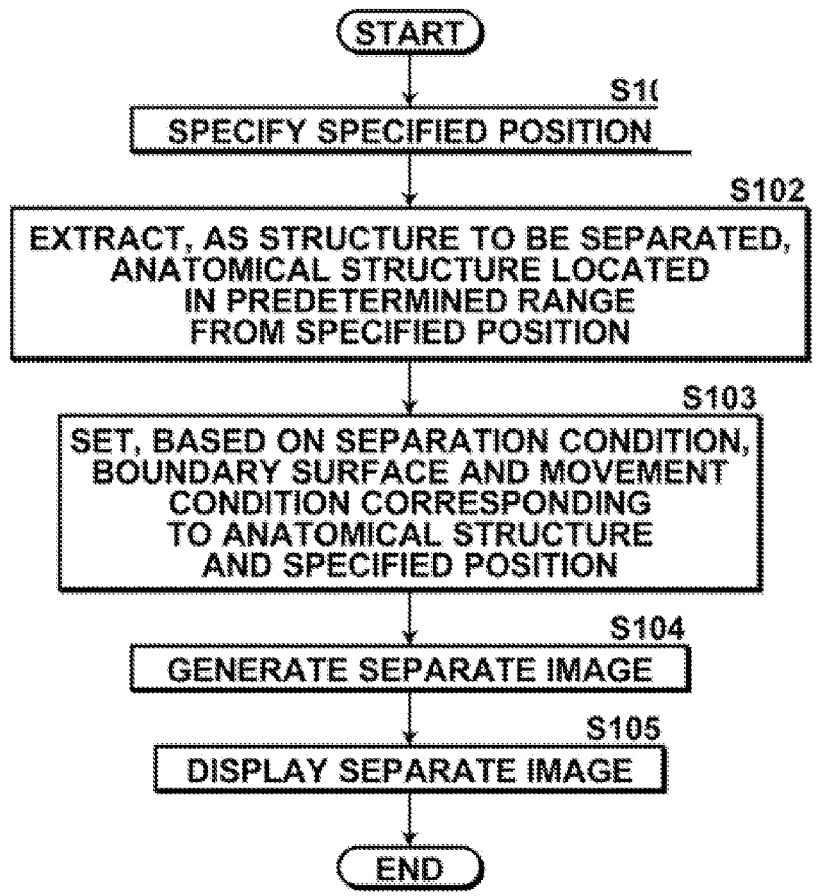

FIG.10

| ANATOMICAL STRUCTURE | BOUNDARY SURFACE / CUTTING SURFACE | SPECIFIED POSITION | MOVEMENT DIRECTION | MOVEMENT AMOUNT | OPTION |
|---|---|---|---|---|---|
| CRANIAL BONE | SPECIFIED SURFACE | SURFACE | DIRECTION PERPENDICULARLY AWAY FROM SPECIFIED SURFACE | $d_{41}$ | HIERARCHICAL DISPLAY (RANK 1) |
| CRANIAL BONE | SPECIFIED SURFACE | SURFACE | DIRECTION PERPENDICULARLY AWAY FROM SPECIFIED SURFACE | $d_{411}$ | HIERARCHICAL DISPLAY (RANK 2) |
| RIGHT CEREBRAL HEMISPHERE | CONTOUR | SURFACE | NOT SPECIFIED | 0 | HIERARCHICAL DISPLAY (RANK 1) |
| RIGHT CEREBRAL HEMISPHERE | CONTOUR | SURFACE | DIRECTION PERPENDICULARLY AWAY FROM SPECIFIED SURFACE | $d_{42}$ | HIERARCHICAL DISPLAY (RANK 2) |
| LEFT CEREBRAL HEMISPHERE | CONTOUR | SURFACE | NOT SPECIFIED | 0 | HIERARCHICAL DISPLAY (RANK 1) |
| LEFT CEREBRAL HEMISPHERE | CONTOUR | SURFACE | DIRECTION PERPENDICULARLY AWAY FROM SPECIFIED SURFACE | $d_{43}$ | HIERARCHICAL DISPLAY (RANK 2) |
| CORPUS CALLOSUM | CONTOUR | SURFACE | NOT SPECIFIED | 0 | HIERARCHICAL DISPLAY (RANK 1) |
| CORPUS CALLOSUM | CONTOUR | SURFACE | DIRECTION PERPENDICULARLY AWAY FROM SPECIFIED SURFACE | $d_{44}$ | HIERARCHICAL DISPLAY (RANK 2) |
| BLOOD VESSELS IN CEREBRUM | CONTOUR | SURFACE | NOT SPECIFIED | 0 | HIERARCHICAL DISPLAY (RANK 1) |
| RIGHT LOBE (LIVER) | CONTOUR | SURFACE | NOT SPECIFIED | 0 | |
| LEFT LOBE (LIVER) | CONTOUR | SURFACE | ROTATE IN DIRECTION AWAY FROM RIGHT LOBE OF LIVER | $r_{37}$ | PARTIAL SEPARATE DISPLAY MOVEMENT AMOUNT OF A REGION OF CONTOUR ADJACENT TO RIGHT LOBE IS SET TO 0 OUTSIDE PREDETERMINED RANGE FROM SPECIFIED SURFACE |
| BLOOD VESSEL (LIVER) | CONTOUR | SURFACE | NOT SPECIFIED | 0 | |
| TOOTH | CONTOUR | POINT | DIRECTION FROM CENTER OF GRAVITY OF TOOTH TOWARD SPECIFIED POINT | $d_{55}$ | |
| ABNORMAL REGION (LARGE INTESTINE) | CONTOUR | CURVED LINE | DIRECTION FROM CENTER OF GRAVITY OF ABNORMAL REGION TOWARD MIDPOINT OF CURVED LINE | $d_{56}$ | |
| ABNORMAL REGION (LARGE INTESTINE) | CONTOUR | CYLINDER | AXIAL DIRECTION OF CYLINDER, AND THE DIRECTION HAVING BEEN SPECIFIED | $d_{56}$ | |

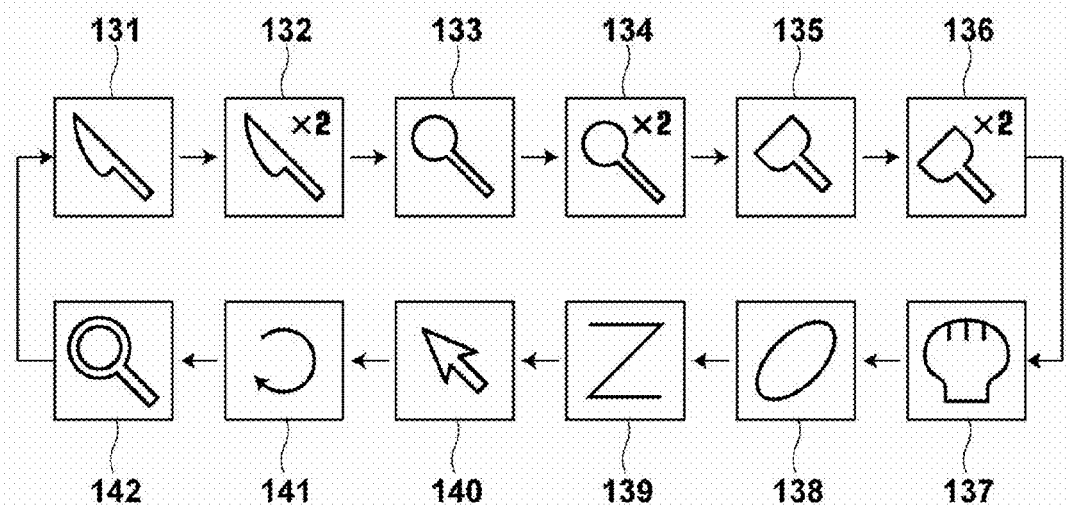
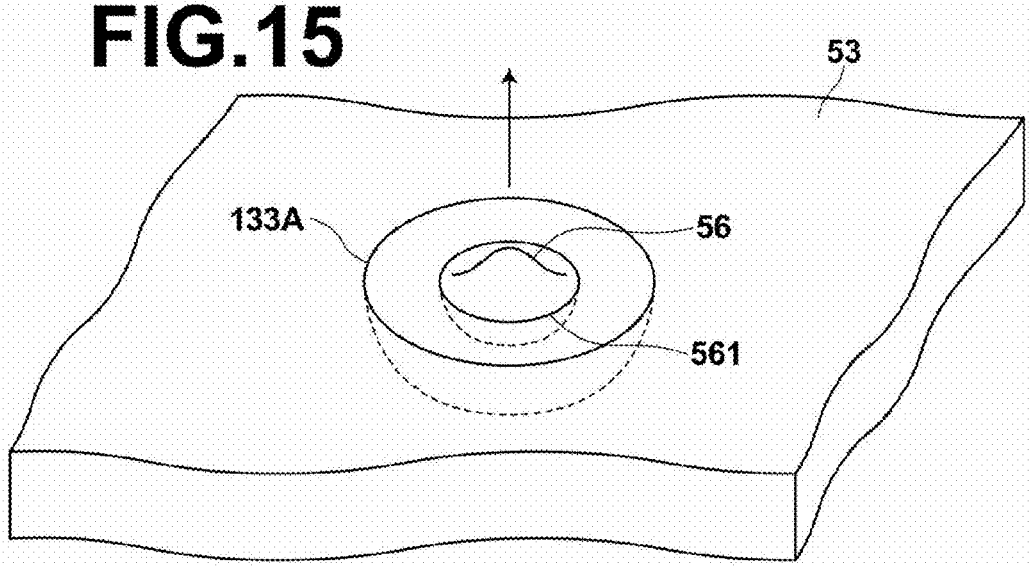

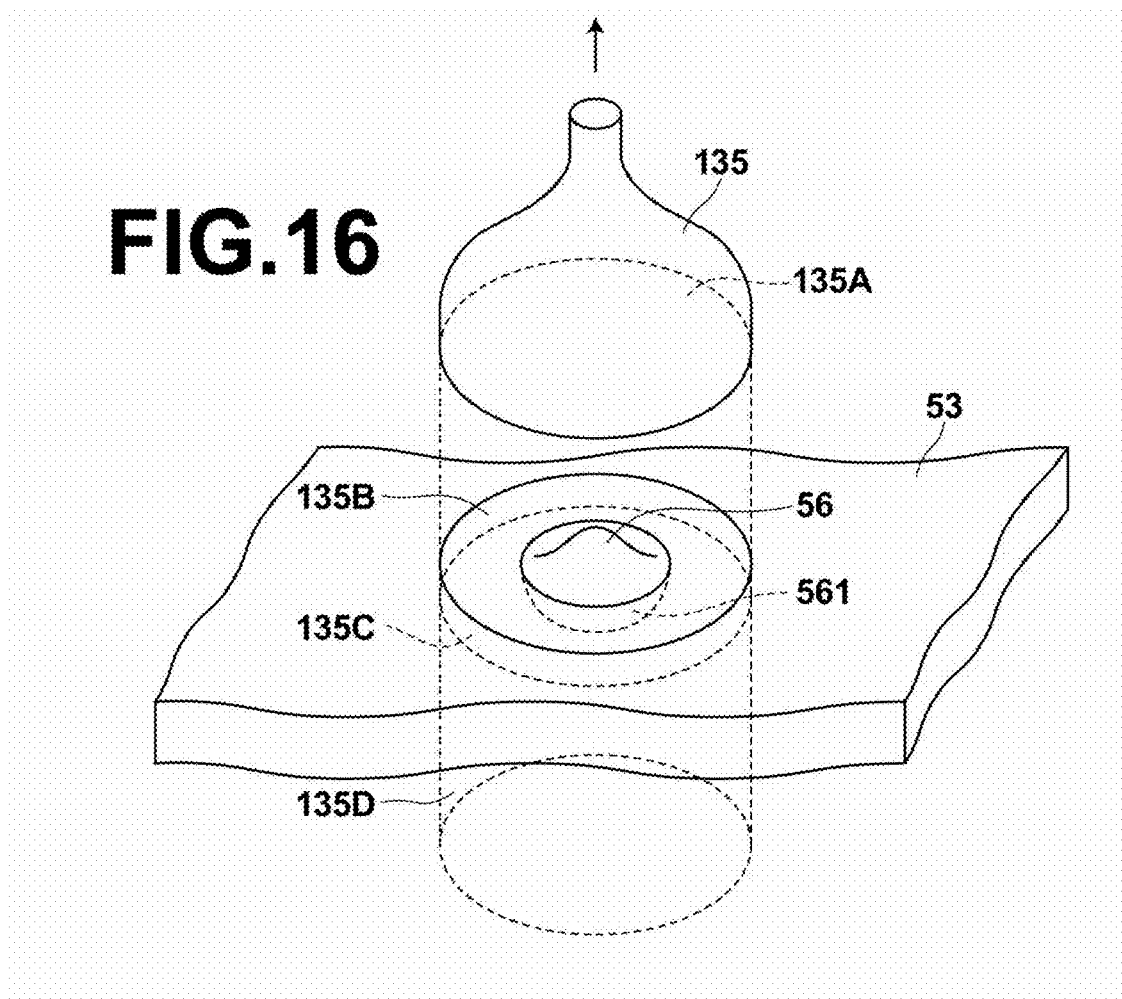

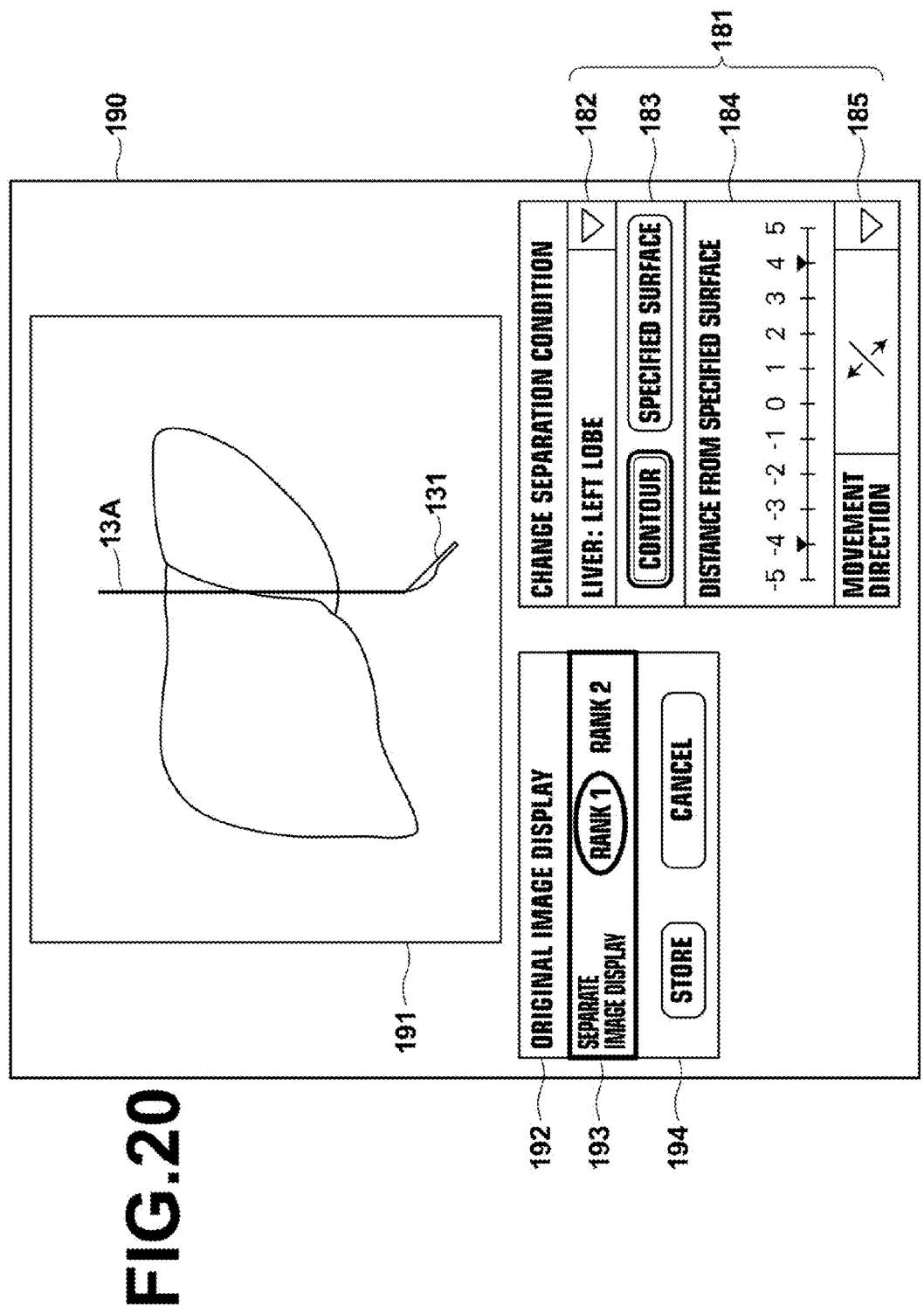

FIG.21

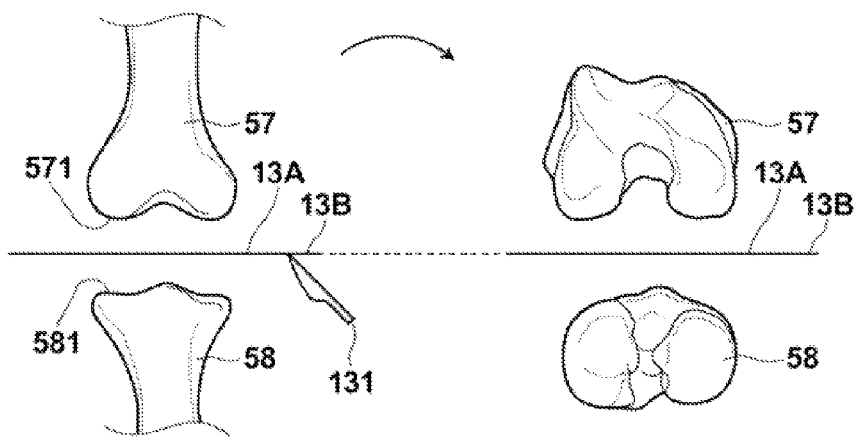

FIG.22

| ANATOMICAL STRUCTURE | BOUNDARY SURFACE / CUTTING SURFACE | MOVEMENT DIRECTION | MOVEMENT AMOUNT | ROTATION DIRECTION AND ROTATION AMOUNT |
|---|---|---|---|---|
| FEMUR | BOUNDARY SURFACE | DIRECTION IN WHICH CENTER OF GRAVITY MOVES AWAY FROM SPECIFIED SURFACE | $d_{57}$ | Rd、Ra |
| TIBIA | BOUNDARY SURFACE | DIRECTION IN WHICH CENTER OF GRAVITY MOVES AWAY FROM SPECIFIED SURFACE | $d_{58}$ | Rd、Ra |
| VERTEBRA | BOUNDARY SURFACE | DIRECTION IN WHICH CENTER OF GRAVITY MOVES AWAY FROM SPECIFIED SURFACE | $d_{62}$ | Rd、Ra |

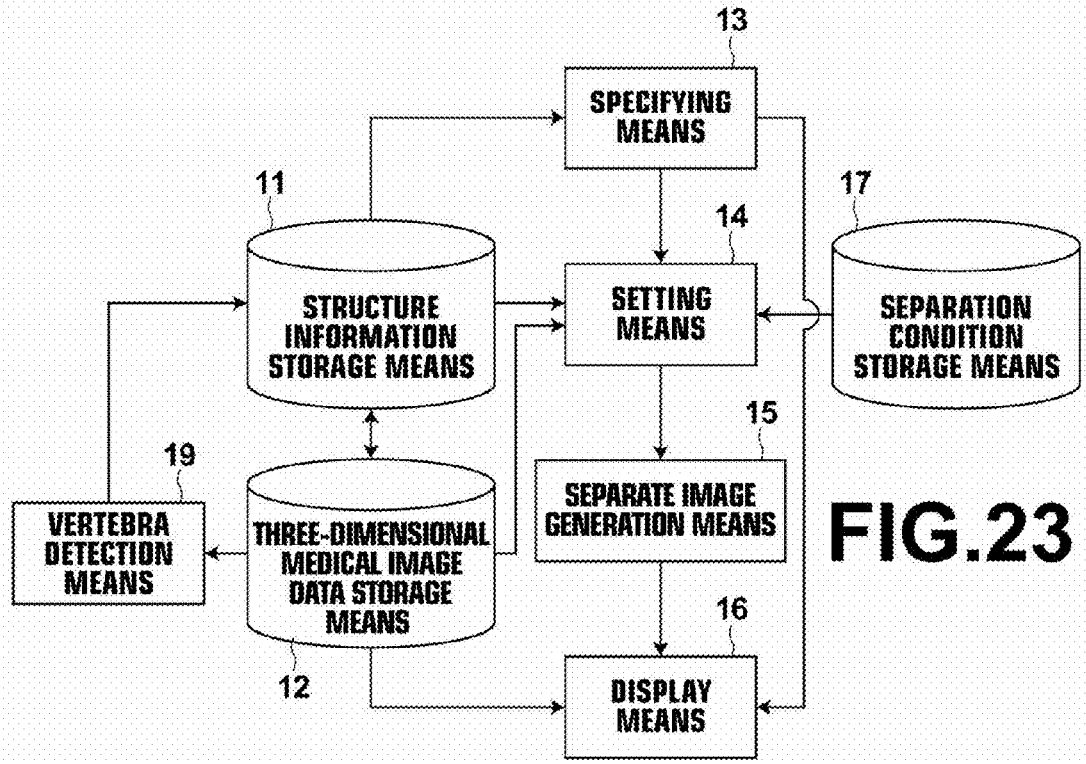
FIG.23
FIG.24
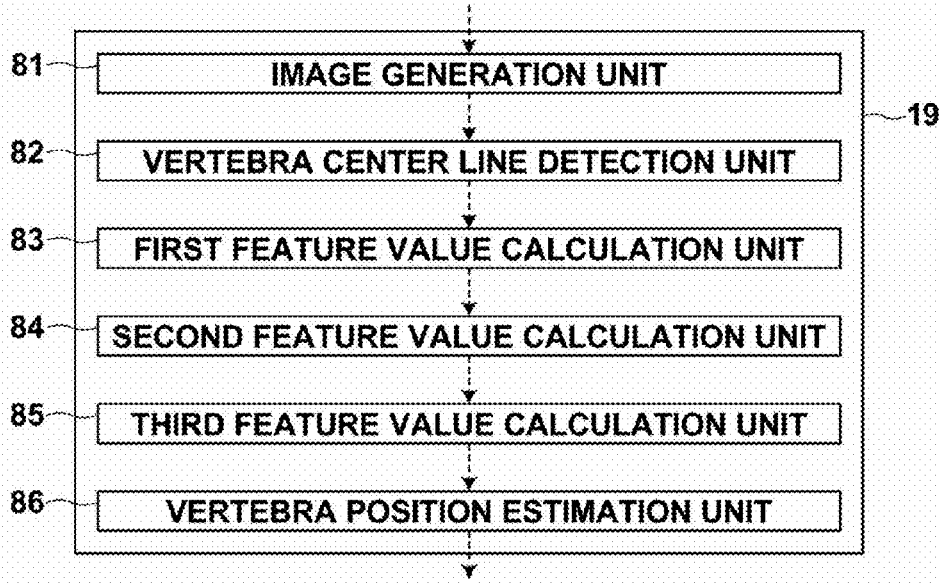

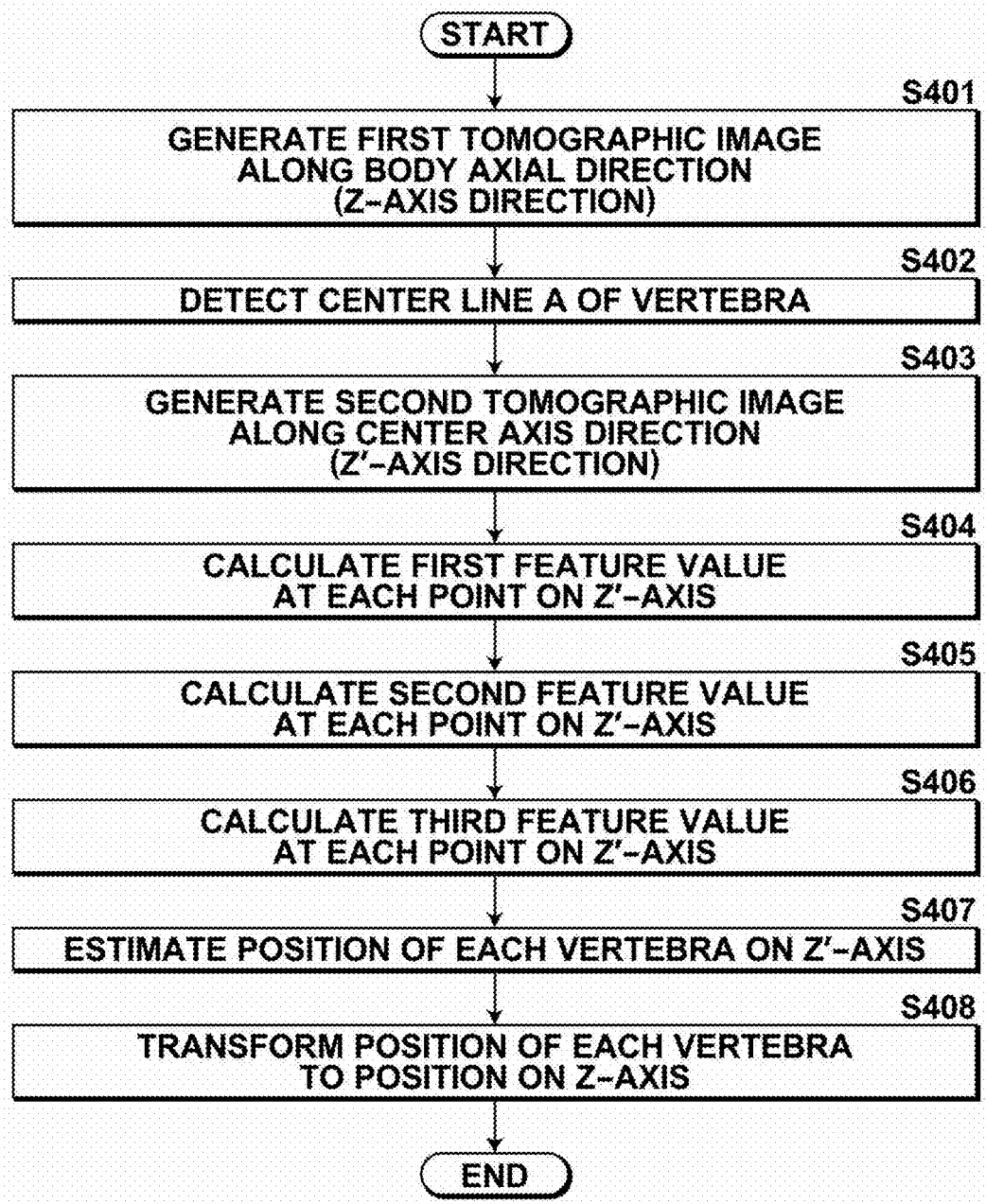

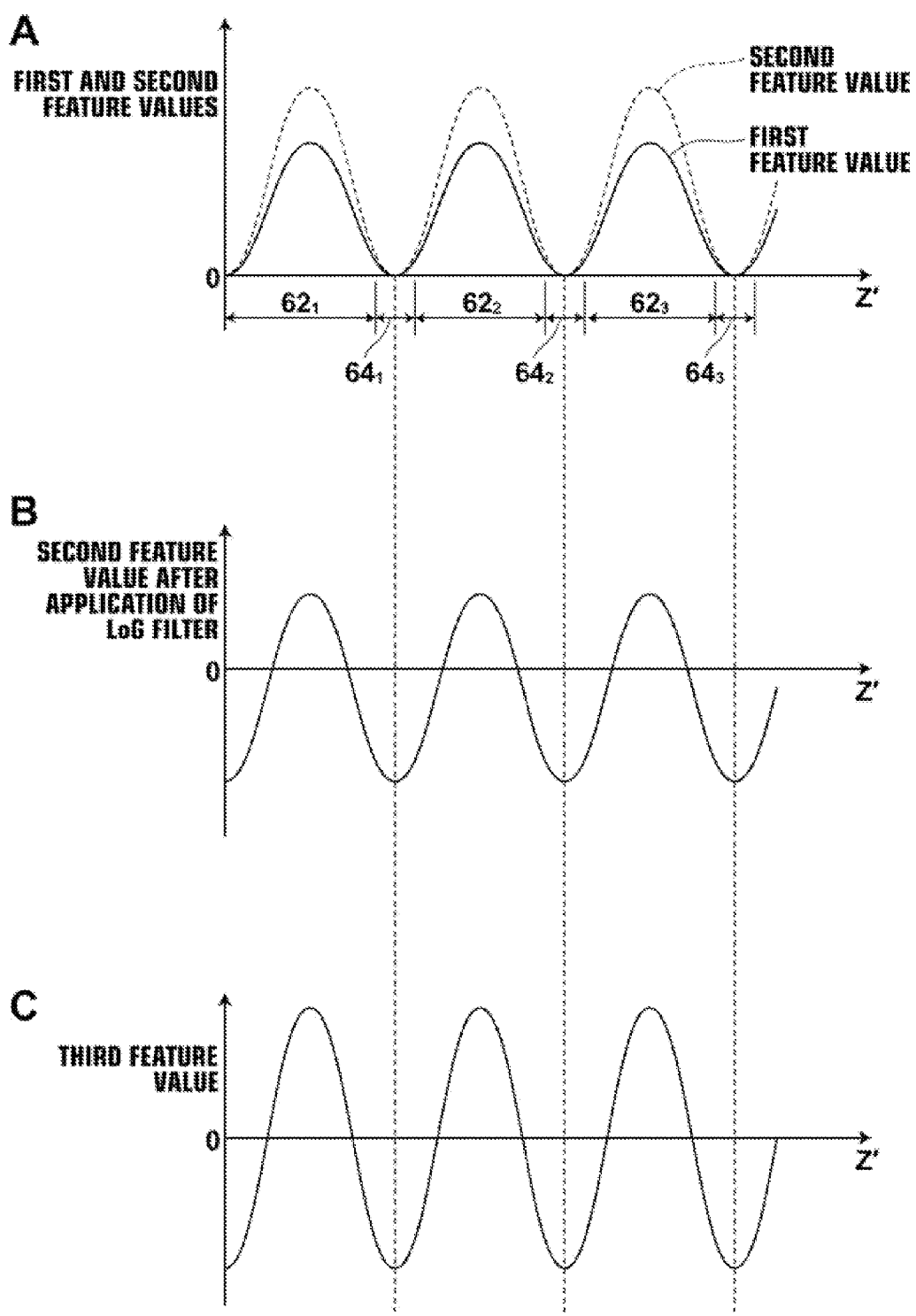

IMAGE DIAGNOSIS SUPPORT APPARATUS, METHOD AND PROGRAM

BACKGROUND OF THE INVENTION

1. Field of the Invention

The present invention relates to an image diagnosis support apparatus, an image diagnosis support method and an image diagnosis support program in which a three-dimensional medical image is displayed to support diagnosis.

2. Description of the Related Art

In recent years, medical image display techniques advanced in medical fields. In the medical image display techniques, a three-dimensional medical image reconstructed from plural sets of imaging image data obtained by imaging by an ultrasound diagnosis apparatus, a CT apparatus or an MRI apparatus, and a medical imaging apparatus, such as a PET, is displayed to support image diagnosis performed in medical fields. In such image diagnosis support techniques, a technique for visualizing a detail of a desired region in a three-dimensional medical image to satisfy the purpose of diagnosis has been drawing attention.

For example, Japanese Unexamined Patent Publication No. 2005-169120 (Patent Document 1) discloses a method for generating a result image of an anatomical structure to be examined. In Patent Document 1, a target structure in tomographic image data is obtained based on a set purpose of diagnosis, and an anatomical standard model corresponding to the target structure is selected, and the anatomical standard model is automatically matched with the target structure in the tomographic image data. Further, the tomographic image data are segmented based on the standard model, and all voxels in a partial model of the standard model are selected in the tomographic image data, thereby generating the result image visualizing the anatomical structure to be examined separated into each partial model.

However, in the method of Patent Document 1, the anatomical structure is separated only at a contour of a partial model that has been set in advance, and displayed. Therefore, it has been impossible to flexibly separate and display the anatomical structure to be diagnosed based on a desirable position required for the purpose of diagnosis. Therefore, in some cases, it was impossible to display an image that was appropriately separated for the purpose of diagnosis, such as diagnosis of an abnormal shadow. It was impossible to separately display a region that was not modeled by a partial model and the like. Further, it was necessary to manually specify a separation position for each partial model through a GUI (graphic user interface). Therefore, especially when plural anatomical structures are present in a three-dimensional image, an operation for separate display was complicated.

SUMMARY OF THE INVENTION

In view of the foregoing circumstances, it is an object of the present invention to provide an image diagnosis support apparatus, an image diagnosis support method and an image diagnosis support program for more effectively visualizing a three-dimensional medical image, by a simple operation, by displaying the three-dimensional medical image that is more flexibly separated at a position corresponding to a position specified based on a purpose of diagnosis.

An image diagnosis support apparatus of the present invention is characterized by comprising:

a three-dimensional medical image data storage means that stores three-dimensional medical image data of a subject;

a display means that displays a three-dimensional medical image based on the stored three-dimensional medical image data;

a structure information storage means that stores a plurality of anatomical structures included in the three-dimensional medical image data;

a specifying means that specifies, in the three-dimensional medical image displayed by the display means, at least one specified position and, if necessary, a cutting surface for separating the plurality of anatomical structures included in the three-dimensional medical image;

a separation condition storage means that stores a separation condition for each anatomical structure of the subject to determine, based on the specified position specified by the specifying means, a boundary surface and, if necessary, a cutting surface for separately displaying the plurality of anatomical structures;

a setting means that extracts, as structures to be separated, the plurality of anatomical structures present within a predetermined range from the specified position that has been specified, and that sets, based on the separation condition, the boundary surface corresponding to the extracted structures to be separated and the specified position that has been specified, and that sets the cutting surface if necessary; and a separate image generation means that generates, based on the boundary surface and, if necessary, the cutting surface as well as based on the three-dimensional medical image data, a three-dimensional medical image in which the structures to be separated are separated by the boundary surface and, if necessary, by the cutting surface, and that makes the display means display the three-dimensional medical image.

An image diagnosis support method of the present invention is characterized by comprising:

displaying a three-dimensional medical image based on three-dimensional medical image data of a subject stored in a three-dimensional medical image data storage means that stores the three-dimensional medical image data;

specifying, in the three-dimensional medical image displayed by the display means, at least one specified position and, if necessary, a cutting surface for separating a plurality of anatomical structures included in the three-dimensional medical image;

extracting, as structures to be separated, the plurality of anatomical structures present within a predetermined range from the specified position that has been specified by referring to a structure information storage means that stores the plurality of anatomical structures included in the three-dimensional medical image data and a separation condition storage means that stores a separation condition for each anatomical structure of the subject to determine, based on the specified position that has been specified, a boundary surface and, if necessary, a cutting surface for separately displaying the plurality of anatomical structures, and setting, based on the separation condition, the boundary surface corresponding to the extracted structures to be separated and the specified position that has been specified and, if necessary, setting the cutting surface; and generating, based on the boundary surface and, if necessary, the cutting surface as well as based on the three-dimensional medical image data, a three-dimensional medical image in which the structures to be separated are separated by the boundary surface and, if necessary, by the cutting surface, and making the display means display the three-dimensional medical image.

An image diagnosis support program is characterized by causing a computer to function as:

a three-dimensional medical image data storage means that stores three-dimensional medical image data of a subject;

a display means that displays a three-dimensional medical image based on the stored three-dimensional medical image data;

a structure information storage means that stores a plurality of anatomical structures included in the three-dimensional medical image data;

a specifying means that specifies, in the three-dimensional medical image displayed by the display means, at least one specified position and, if necessary, a cutting surface for separating the plurality of anatomical structures included in the three-dimensional medical image;

a separation condition storage means that stores a separation condition for each anatomical structure of the subject to determine, based on the specified position specified by the specifying means, a boundary surface and, if necessary, a cutting surface for separately displaying the plurality of anatomical structures;

a setting means that extracts, as structures to be separated, the plurality of anatomical structures present within a predetermined range from the specified position that has been specified, and that sets, based on the separation condition, the boundary surface corresponding to the extracted structures to be separated and the specified position that has been specified, and that sets the cutting surface if necessary; and a separate image generation means that generates, based on the boundary surface and, if necessary, the cutting surface as well as based on the three-dimensional medical image data, a three-dimensional medical image in which the structures to be separated are separated by the boundary surface and, if necessary, by the cutting surface, and that makes the display means display the three-dimensional medical image.

In the specification of the present application, an anatomical structure is not limited to a structure, such as an organ, a bone and a blood vessel, which is classified by the function or the shape of the structure as long as the anatomical structure is recognizable in a subject. For example, fat, such as subcutaneous fat and visceral fat, and a lesion, such as a tumor, are included in examples of the anatomical structure. As another example, a structure constituting a part of an anatomical structure is also included in the examples of the anatomical structure. Specifically, for example, blood vessels in a liver, a right lobe and a left lobe of the liver and the like, which constitute the liver, and a right ventricle, a right atrium, a left ventricle, a left atrium and the like, which constitute a heart, are included in the examples of the anatomical structure. Further, a region segmented based on a dominant area, which dominates an organ, is also included in the examples of the anatomical structure.

Further, the specified position may be specified by use of any one of a point, a line, a surface and a three-dimensional object. For example, when a line is used, a curved line or a straight line, or a combination thereof may be used. When a surface is used, a curved surface or a plane, or a combination thereof may be used. When a three-dimensional object is used, the three-dimensional object may consist of only curved surfaces, or only planes, or include them in combination.

Further, the expression "that sets the boundary surface and that sets the cutting surface if necessary" means that boundary surfaces may be set for all of plural anatomical structures in some cases based on a separation condition, and that a boundary surface or surfaces may be set for a part of the plural anatomical structures and a cutting surface or surfaces may be set for the other anatomical structures in some cases based on a separation condition.

The expression "extracting, as structures to be cut, the plurality of anatomical structures present within a predetermined range from the specified position" means that such structures may be defined by using various kinds of judgment method as long as anatomical structures present in the vicinity of a predetermined range from the specified position can be judged.

For example, when the specified position is specified by using a point, an anatomical structure located in a range in which a distance between the point and a specific point on or within the anatomical structure is within a predetermined range may be defined as the structure to be separated. Alternatively, an anatomical structure including the point, which is the specified position, may be defined as the structure to be separated. When the specified position is specified by using a straight line, an anatomical structure located in a range in which a shortest distance between a point on the straight line and a specific point on or within the anatomical structure is within a predetermined range may be defined as the structure to be separated. Alternatively, an anatomical structure including a part or all of the specified straight line may be defined as the structure to be separated. When the specified position is specified by using a surface, an anatomical structure located in a range in which a shortest distance between the surface and a specific point on or within the anatomical structure is within a predetermined range may be defined as the structure to be separated. Alternatively, an anatomical structure including a part or all of the specified surface may be defined as the structure to be separated. When the specified position is specified by using a three-dimensional object, an anatomical structure located in a range in which a shortest distance between a point in the three-dimensional object and a specific point on or within the anatomical structure is within a predetermined range may be defined as the structure to be separated. Alternatively, an anatomical structure including a part or all of the specified three-dimensional object may be defined as the structure to be separated.

Further, the phrase "a boundary surface for separately displaying" refers to a surface that becomes a boundary when plural anatomical structures that are structures to be cut are displayed with some distance therebetween. The boundary surface may be a plane, or a curved surface, or a combination thereof. Further, the boundary surface may be set in such a manner that plural anatomical structures are completely separated from each other. Alternatively, a boundary surface may be set only for a part of the plural anatomical structures. The boundary surface may be set in such a manner that only a part of the plural anatomical structures is separated.

In the image diagnosis support apparatus of the present invention, it is desirable that the separation condition determines, as the boundary surface, a contour of the structure to be separated.

In the image diagnosis support apparatus of the present invention, it is desirable that the separation condition determines, as the boundary surface, a contour of a predetermined anatomical structure of the plurality of anatomical structures when the predetermined anatomical structure constitutes a part of another anatomical structure. For example, the other anatomical structure may be a liver, and the predetermined anatomical structure may be blood vessels constituting the liver.

In the image diagnosis support apparatus of the present invention, the separation condition may determine the boundary surface in such a manner that only a part of the anatomical structures is separately displayed.

It is desirable that the image diagnosis support apparatus of the present invention further includes a separation condition change means that receives change of the separation condition in display of the three-dimensional medical image displayed by the display means, and that changes the separation condition stored in the separation condition storage means.

In the image diagnosis support apparatus of the present invention, the specifying means may specify the specified position in a predetermined region of the three-dimensional medical image by limiting the predetermined region.

The expression "by limiting the predetermined region" means that a specified position is specified in a confined region. The region may be limited in various kinds of shape, for example, such as a segment, a polygon, a disk, a prism, a cylinder, a polyhedron, and a hemisphere.

In the image diagnosis support apparatus of the present invention, the anatomical structures may be bones. For example, the anatomical structure may be a bone constituting each joint, such as a femur, a patella, a tibia and the like constituting a knee joint. Alternatively, the anatomical structure may be a vertebra constituting a spine.

It is desirable that the separation condition further determines a rotation direction and a rotation amount for rotating and displaying the anatomical structure. It is desirable that the separate image generation means generates a three-dimensional medical image in which the anatomical structure is separated and rotated based on the separation condition. For example, an anatomical structure may be rotated in such a manner that a boundary surface that separates the anatomical structure is displayed on a display screen. Further, the anatomical structure may be rotated in various directions by an arbitrary rotation amount.

The specifying means may specify the specified position by specifying a predetermined tomographic image of a plurality of tomographic images constituting the three-dimensional medical image instead of specifying the specified position in the three-dimensional medical image. The predetermined tomographic image may be plural slice images obtained by tomography by using a CT apparatus, or the like. Alternatively, the predetermined tomographic image may represent an arbitrary cross section generated from a three-dimensional medical image by using an MPR method or the like. Reduced images of these tomographic images may be displayed, or a tomographic image may represent a part of the tomographic images. Further, the specifying means may display a list of plural tomographic images constituting a three-dimensional medical image, and specify a predetermined tomographic image of the plural tomographic images displayed in the list. Alternatively, the specifying means may display plural tomographic images constituting the three-dimensional medical image by sequentially switching displayed images based on a position in a three-dimensional coordinate system, and when a desired tomographic image is displayed, the specifying means may specify a predetermined tomographic image by using an input device, such as a mouse.

According to the image diagnosis support apparatus, the image diagnosis support method and the image diagnosis support program of the present invention, at least one specified position and, if necessary, a cutting surface for separating plural anatomical structures included in a three-dimensional medical image are specified in the three-dimensional medical image displayed by a display means. Further, the plural anatomical structures present within a predetermined range from the specified position that has been specified are extracted, as structures to be separated, by referring to a separation condition storage means that stores a separation condition to determine, based on the specified position that has been specified, a boundary surface and, if necessary, a cutting surface for separately displaying the plural anatomical structures. Further, the boundary surface corresponding to the extracted structures to be separated and the specified position that has been specified and, if necessary, the cutting surface are set based on the separation condition. Therefore, it is possible to automatically set, for each of the plural anatomical structures, an appropriate boundary surface based on a specified position and, if necessary, a cutting surface. Further, it is possible to more flexibly display a three-dimensional medical image separated based on a desired position appropriate for the purpose of diagnosis by a simple operation of only specifying the desired position. Therefore, it is possible to more effectively visualize the three-dimensional medical image.

When the separation condition determines, as the boundary surface, a contour of the structure to be separated, it is possible to satisfy a demand for visualizing a contour of the anatomical structure. Since it is possible to easily display, based on a specified position, an image separated at a contour within a predetermined range from the specified position, it is possible to display a desired separate image by a simple operation.

The separation condition may determine, as the boundary surface, a contour of a predetermined anatomical structure of the plural anatomical structures when the predetermined anatomical structure constitutes a part of another anatomical structure. In such a case, even if the other anatomical structure is separately displayed by a boundary surface or a cutting surface, the predetermined structure is not separately displayed by a cutting surface, but displayed in such a manner that a contour of the predetermined structure is maintained. Therefore, it is possible to separately display the other anatomical structure and the predetermined structure constituting the other anatomical structure so that they are easily diagnosed respectively.

When the separation condition determines the boundary surface in such a manner that only a part of the anatomical structures is separately displayed, it is possible to separately display by separating only a desired part of the anatomical structures based on the purpose of diagnosis.

When a separation condition change means that receives change of the separation condition in display of the three-dimensional medical image displayed by the display means, and that changes the separation condition stored in the separation condition storage means is further provided, it is possible to flexibly change the separation condition based on the purpose of diagnosis. Therefore, it is possible to easily perform desired separate display.

When the specifying means specifies the specified position in a region of the three-dimensional medical image by limiting the region, it is possible to set a boundary surface and, if necessary, a cutting surface in a desired region. Therefore, it is possible to display in such a manner that separate display is performed only in the desired region.

When the separation condition further determines a rotation direction and a rotation amount for rotating and displaying the anatomical structures, and the separate image generation means generates a three-dimensional medical image in which the anatomical structures are separated and rotated based on the separation condition, it is possible to rotate an anatomical structure in such a manner that a boundary surface that separates the anatomical structure is displayed on a display screen, or the like. Since it is possible to display the anatomical structure that has been rotated in various directions by an arbitrary rotation amount, it is possible to easily perform desired separate display.

When the specifying means specifies the specified position by specifying a predetermined tomographic image of a plurality of tomographic images constituting the three-dimensional medical image instead of specifying the specified position in the three-dimensional medical image, it is possible to easily specify a desired specified position based on the position of a desired tomographic image.

BRIEF DESCRIPTION OF THE DRAWINGS

FIG. 1 a functional block diagram of an image diagnosis support apparatus according to a first embodiment;

FIG. 2 a block diagram illustrating the configuration of the first embodiment;

FIG. 3 an example of a separation condition table according to the first embodiment;

FIG. 4C an image diagram illustrating a modified example of a separate image of a liver according to the first embodiment;

FIG. 5 a flow chart illustrating a flow of image diagnosis support processing according to the first embodiment;

FIG. 10 an example of a separation condition table in the second embodiment, a third embodiment and a fourth embodiment;

FIG. 14 a diagram illustrating an example of selecting and specifying a specified position according to the fourth embodiment;

FIG. 15 a diagram illustrating an example of specifying a position of a malignant region according to the fourth embodiment (specified by curved line);

FIG. 16 a diagram illustrating an example of specifying a position of a malignant region according to the fourth embodiment (specified by three-dimensional object);

FIG. 20 an example of display on a display screen according to the fifth embodiment;

FIG. 21 an image diagram for explaining methods for specifying a position and displaying data on a display screen according to a sixth embodiment;

FIG. 22 an example of a separation condition table according to the sixth embodiment and a seventh embodiment;

FIG. 23 a functional block diagram of the seventh embodiment;

FIG. 24 a functional block diagram of a vertebra extraction means 19 according to the seventh embodiment;

FIG. 27 a flow chart of the method for extracting a vertebra according to the seventh embodiment;

FIG. 30 a diagram illustrating the profiles of first and second feature values in Z'-axis direction, and the profile of the second feature values after application of a LoG filter to the second feature values, and the profile of third feature values in Z'-axis direction.

DESCRIPTION OF THE PREFERRED EMBODIMENTS

Figure 4A:
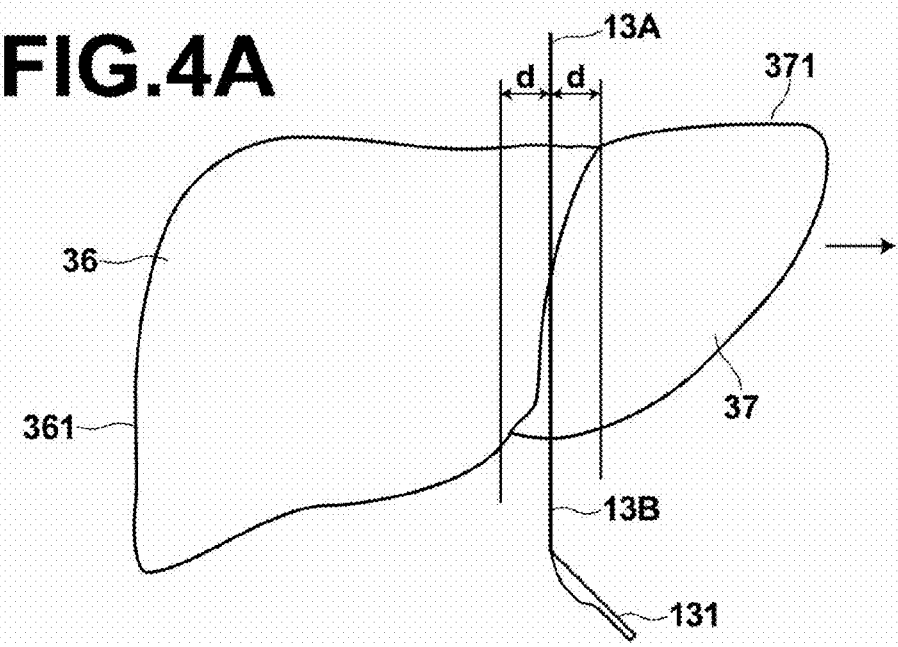
FIG. 4A a diagram illustrating an example of specifying a position in a liver according to the first embodiment.

Hereinafter, embodiments of an image diagnosis support apparatus according to the present invention will be described in detail with reference to drawings.

FIG. 1 is a block diagram illustrating the function of an image diagnosis support apparatus according to an embodiment of the present invention. The image diagnosis support apparatus illustrated in FIG. 1 includes a three-dimensional medical image data storage means 12 that stores three-dimensional medical image data about a subject, a display means 16 that displays a three-dimensional medical image based on the stored three-dimensional medical image data, a structure information storage means 11 that stores plural anatomical structures included in the three-dimensional medical image data, a specifying means 13 that specifies, in the three-dimensional medical image displayed by the display means, at least one specified position and, if necessary, a cutting surface for separating the plural anatomical structures included in the three-dimensional medical image, a separation condition storage means 17 that stores a separation condition for each anatomical structure of the subject to determine, based on the specified position specified by the specifying means 13, a boundary surface and, if necessary, a cutting surface for separately displaying the plural anatomical structures, a setting means 14 that extracts, as structures to be separated, the plural anatomical structures present within a predetermined range from the specified position that has been specified, and that sets, based on the separation condition, the boundary surface corresponding to the extracted structures to be separated and the specified position that has been specified, and that sets the cutting surface if necessary, and a separate image generation means 15 that generates, based on the boundary surface and, if necessary, the cutting surface as well as based on the three-dimensional medical image data, a three-dimensional medical image in which the structures to be separated are separated by the boundary surface and, if necessary, by the cutting surface, and that makes the display means display the three-dimensional medical image.

Next, configuration related to an image diagnosis support apparatus according to a first embodiment will be described. In the specification of the present application, the same sign will be assigned to the same part, and explanation about the same part will be omitted.

FIG. 2 is a schematic block diagram illustrating the configuration of an image processing workstation 100. As illustrated in FIG. 2, the image diagnosis support apparatus according to embodiments of the present invention is constituted by the image processing workstation 100 including a display unit 101, such as a liquid crystal monitor, which performs various kinds of display, an input unit 103 including a keyboard, a mouse and the like for performing various kinds of input, a hard disk 105 that stores various kinds of program for controlling the image diagnosis support apparatus according to the embodiments of the present invention and various kinds of data, such as image data, a CPU 107 that controls the image diagnosis support apparatus according the embodiments of the present invention by executing various kinds of program, a memory 109 that functions as a work area during execution of programs, and a communication interface 111 connected to a network through a bus 113.

In all embodiments, the function of the present invention is performed by a computer by executing programs installed from the outside. A group of information including the programs may be provided by a storage medium, such as a CD-ROM, a flash memory and an FD, or supplied from an external storage medium through a network, and installed in the computer.

The three-dimensional medical image data storage means 12 mainly includes the hard disk 105. The three-dimensional medical image data storage means 12 stores slice images obtained by a CT apparatus, an MRI apparatus, a PET, an ultrasound diagnosis apparatus, or the like, and a three-dimensional medical image reconstructed from these slice images. A typical example of the stored image is an image represented by volume rendering. However, the present invention is not limited to the embodiments of the present invention, and various pseudo-three-dimensional image generation methods may be applied to the image diagnosis support apparatus of the present invention. For example, a marching cube method or a surface rendering method may be applied. A format for storing image data and a format adopted when image data are sent to another apparatus through a network are based on a protocol, such as DICOM (Digital Imaging and Communications in Medicine).

The display means 16 includes a display unit 101 for displaying a three-dimensional medical image. The display means 16 displays, on the display unit 101, a three-dimensional medical image obtained from the three-dimensional medical image data storage means 12.

The structure information storage means 11 stores plural anatomical structure structures recognized in three-dimensional medical image data. Here, the anatomical structures are not limited to structures, such as an organ, a bone and a blood vessel, which are classified based on functions and shapes as long as the anatomical structures are recognizable in a subject. For example, fat, such as subcutaneous fat and visceral fat, and a lesion, such as a tumor, are included in the anatomical structures. As another example, a structure constituting a part of an anatomical structure is also included in the anatomical structures. Specifically, for example, blood vessels in a liver, a right lobe and a left lobe of the liver and the like, which constitute the liver, and a right atrium, a right ventricle, a left atrium, and a left ventricle and the like, which constitute a heart, are included in the anatomical structures. Further, a region segmented based on a dominant area, which dominates an organ, is also included in the anatomical structures. The expression "dominates an organ" means maintaining the normal function of an organ by supplying oxygen and nutrition to the organ. For example, if the organ is a heart, a right coronary artery and a left coronary artery (a left anterior descending branch and a left circumflex branch) correspond to blood vessels dominating the organ. If the organ is a brain, a superior sagittal sinus, an inferior sagittal sinus, a great cerebral vein and the like correspond to blood vessels dominating the organ. If the organ is a liver, a portal vein corresponds to a blood vessel dominating the organ.

Further, a dominant area obtained by calculation by using various known methods may be included in anatomical structures. For example, for the heart, a dominant area estimated by using a method disclosed in "Diagnosis Support Apparatus, Diagnosis Support Program, and Diagnosis Support Method" (Japanese Application No. 2009-158534), filed by the applicant of this application, and the like may be included in the anatomical structures. Specifically, in the method disclosed in "Diagnosis Support Apparatus, Diagnosis Support Program, and Diagnosis Support Method" (Japanese Application No. 2009-158534), filed by the applicant of this application, plural coronary artery regions that dominate the heart are extracted from a three-dimensional image. Further, a coordinate point away from each of plural candidate points constituting a center line of each coronary artery is obtained based on each of the coronary arteries. The coordinate point is away from the candidate point, by distance Δd, in a direction that is perpendicular to the principal axis direction of each coronary artery and that extends along the surface of a cardiac muscle. The plural coordinate points obtained by this processing represent a tentative boundary line of a dominant area of the coronary artery. In other words, a dominant area of the coronary artery with width Δd is tentatively set. Further, with respect to the plural dominant areas of coronary arteries (LAD region, LCX region, and RCA region) that have been tentatively set, judgment is made, based on the positional relationship between the tentative boundary lines set for respective coronary arteries, whether an overlapping region is present. When no overlapping region of the dominant areas of the coronary arteries is present, a new tentative boundary line is set again at a position that is away, by distance 2Δd, from the candidate point. Similar processing is repeated until overlap between the dominant areas of the coronary arteries occurs. If the width of a region when overlap occurs is nΔd (n is a positive integer), a region with width (n−1)Δd that was tentatively set in a step immediately before this step is estimated as a dominant area of the coronary artery. Alternatively, a region that was tentatively set two or more steps before this step may be estimated as a dominant area of the coronary artery.

For the liver, anatomical structures may include a dominant area obtained, for example, by using a method for identifying a dominant area of each blood vessel, as a liver segment. The liver segment is identified by extracting blood vessels in a liver region, and by identifying a blood vessel dominating a region (hepatic parenchyma or the like) other than the blood vessels in the liver region by using a Voronoi diagram (Voronoi diagram) (please refer to Japanese Unexamined Patent Publication No. 2003-033349, R. Beichel et al., "Liver Segment Approximation in CT Data for Surgical Resection Planning", Medical Imaging 2004: Image Processing, edited by J. M. Fitzpatrick; M. Sonka, Proceedings of the SPIE, Vol. 5370, pp. 1435-1446, 2004, and the like).

Further, for the lung field, anatomical structures may include a dominant area, such as a dominant area of a small region of bronchi. Specifically, a set of voxels in the bronchus region is extracted by using a region growing method, and thinning is performed on the extracted bronchus region. Further, each voxel on the thinned lines is classified, based on connection relationship between the obtained thin lines representing the bronchi, into an end point, an edge (edge) or a branching point. Accordingly, tree structure data representing the bronchi are obtained (for detail, please refer to D. Kobayashi at al., "Trial of Branch Base Tree Structure Model Construction for Blood Vessel Geometric Representation", [on line], RIKEN, RIKEN Symposium "Digitization and Database Construction Research of Organism Shape Information", pp. 84-92, 2005, [Search on Jan. 6, 2010], Internet URL:http://www.comp-bio.riken.jp/keijyo/products/2005 1 files/kobayashi print.pdf, S. Nakamura et al., "Automated Classification of Pulmonary Artery and Vein from Chest X-ray CT Images by Tree Structure Analysis", Technical Research Report of the Institute of Electronics, Information and Communication Engineers, Technical Report of IEICE, Vol. 105, No. 580, pp. 105-108, 2006 [Searched on Nov. 20, 2009], Internet URL:http://www.murase.nuie.nagoya-u.ac.jp/~ide/res/paper/J05-kenkyukai-snaka-1.pdf, and the like). Further, the obtained bronchi structure is used as a set of kernel points, and three-dimensional Voronoi division is performed to obtain to which bronchus of the bronchi, which constitute the bronchus structure, each voxel in the lung field is closest. In other words, a bronchus dominating each voxel in the lung field is obtained. Further, a region dominated by the same bronchus is determined as a dominant area of the bronchus (for detail, please refer to Y. Hirano et al., "Quantification of shrinkage of lung lobes in chest CT images using the 3D Voronoi division and application to tumor discrimination", [online], Proceedings of 20th Annual Meeting of the Japanese Society of Medical Imaging Technology, pp. 315-316, 2001, [Searched on Nov. 20, 2009], Internet URL:http://mase.itc.nagoya-u.ac.jp/~hirano/Papers/JAMIT2001.pdf, and the like).

In the specification of the present application, anatomical structures may be structures recognized by using various known techniques. For example, the anatomical structures may be extracted by computer-aided image diagnosis (CAD: Computer Aided Diagnosis). As specific examples of extraction of each organ in each anatomical structure, techniques disclosed in Japanese Unexamined Patent Publication No. 2001-137230 and Japanese Unexamined Patent Publication No. 2008-253293 may be used for the lung field. Further, techniques disclosed in Japanese Unexamined Patent Publication No. 2001-283191 and Japanese Unexamined Patent Publication No. 2002-345807 may be used for extraction of the liver. The technique disclosed in Japanese Examined Patent Publication No. 2008-043564 may be used for bones, and the technique disclosed in Japanese Examined Patent Publication No. 2004-141612 may be used for the heart. Further, other organ recognition techniques are adoptable as long as an organ to which the specified position of a lesion belongs is extractable.

As techniques for detection of a lesion region, the following techniques may be adopted. Specifically, techniques for detecting a lung cancer disclosed in Japanese Unexamined Patent Publication No. 2003-225231, Japanese Unexamined Patent Publication No. 2003-271924, and K. Kubota et al., "Evaluation of Computer-Aided Diagnosis system for Lung Cancer based on Helical CT images", Technical Report of IEICE, Vol. 101, No. 310, pp. 41-46, 2001 are applicable. Further, detection techniques of diffuse lung diseases, such as consolidation, Ground-Glass Opacity (GGO), Crazy-Paving, honeycomb-shaped shadow, pulmonary emphysema shadow and particle-shaped shadow, disclosed in S. Kido et al., "Intelligent CAD for diffuse lung diseases", Grant-in-Aid for Scientific Research, granted by the Ministry of Education, Culture, Sports, Science and Technology, Study in Specific Field, "Intellectual Diagnosis Aid of Multi-Dimensional Medical Image", Proceedings of 4th Symposium, pp. 45-54, 2007 are applicable. Further, a technique for detecting a liver cancer disclosed in Y. Wakida et al., "Liver Cancer Detection based on a Temporal Density Feature from Abdominal Dynamic X-ray CT Images", Proceedings of Journal of Computer Aided Diagnosis of Medical Image, Vol. 10, No. 1, pp. 1-10, 2007 is applicable. Further, a technique for detecting hepatocellular carcinoma, hepatic cyst, hepatic hemangioma, bleeding in a liver region and bleeding in a brain region disclosed in H. Fujita et al., "Intelligent Computer-aided Diagnosis Based on Normal Structure Recognition of Human Body", Grant-in-Aid for Scientific Research, granted by the Ministry of Education, Culture, Sports, Science and Technology, Study in Specific Field, "Intellectual Diagnosis Aid of Multi-Dimensional Medical Image", Proceedings of 4th Symposium, pp. 55-60, 2007 is applicable.

Further, a technique for detecting an abnormality in a blood vessel, as disclosed in Japanese Unexamined Patent Publication No. 2004-329929, a technique for detecting an abnormal shadow candidate, as disclosed in Japanese Unexamined Patent Publication No. 10 (1998)-097624, which was filed by the applicant of this application, and a technique for detecting a calcified region, as disclosed in Japanese Unexamined Patent Publication No. 8 (1996)-215183, may be used.

The specifying means 13 includes an input tool, such as a mouse, a pentouch tool, and a touch panel. The specifying means 13 specifies, in a three-dimensional medical image displayed by the display means 16, at least one specified position and, if necessary, a cutting surface for separating plural anatomical structures included in the three-dimensional medical image.

A method for specifying a position is not limited to the first embodiment of the present invention. Various known methods may be used as long as a position is specifiable. The position may be specified by only one of a point, a line, a surface and a three-dimensional object. An operation for specifying a position by a line may be performed by using a curved line or a straight line, or by using a curved line and a straight line in combination. An operation for specifying a position by a surface may be performed by using a curved surface or a plane, or by using a curved surface and a plane in combination. Further, an operation for specifying a position by a three-dimensional object may be performed by using a three-dimensional object composed of only curved surfaces or a three-dimensional object composed of only planes, or by using a three-dimensional object composed of a curved surface or surfaces and a plane or planes in combination.

The separation condition storage means 17 mainly includes a hard disk 105. A separation condition is determined for each anatomical structure of a subject. The separation condition determines, based on a specified position that is specified by the specifying means 13, a boundary surface and, if necessary, a cutting surface for separately displaying the plural anatomical structures. Further, in the first embodiment, the separation condition includes a movement condition composed of information representing a movement amount and a movement direction of an anatomical structure of a subject. The movement condition determines a movement amount and a movement direction of an anatomical structure for each anatomical structure. The movement condition is not limited to the embodiments described in the specification of the present application. The movement condition may be stored in a movement condition storage means composed of a storage means, such as a hard disk, separately from the separation condition. Further, the setting means or the separate image generation means may determine a movement condition corresponding to each anatomical structure by referring to the movement condition storage means. However, when the movement amount in the movement condition is zero, in other words, when the anatomical structure is not moved, the movement condition may represent only the movement distance. The movement amount should directly or indirectly represent an amount of movement. For example, the movement amount may be represented by a distance of movement, an angle of movement, and the like. In principle, the movement condition is composed of a movement amount based on a specified position and a movement direction based on the specified position. However, when the anatomical structure is not moved, the movement condition may represent only the movement amount.

Further, the separation condition may be defined by using various known methods as long as each anatomical structure is related to a boundary surface or a cutting surface for separating the anatomical structure. Further, various known methods for setting a surface are adoptable as the method for specifying the cutting surface. Further, the movement condition may be set by using various known methods as long as a movement amount and a movement direction are indirectly or directly settable.

The separation condition may be set by using, as a boundary surface, various kinds of shape settable for an anatomical structure. It is desirable that a contour of a structure to be separated is determined as the boundary surface. When the contour of the structure to be cut is determined as the boundary surface, it is possible to display the anatomical structure that is separated at the contour only by specifying a specified position to satisfy a demand for visualizing the contour of the anatomical structure. Therefore, efficient image diagnosis is possible by a simple operation. Further, when a user wants to observe a cutting surface, or when it is not appropriate to set a contour as a boundary surface, a specified surface may be set as a cutting surface in the separation condition, if necessary.

A separation condition table 170 in the first embodiment describes, as an example, only a case of specifying a position for each anatomical structure by the specifying means 13 by using a surface. However, each anatomical structure may be related to a boundary surface or a cutting surface for separating anatomical structures in such a manner that a part or all of the boundary surface or the cutting surface for separating the anatomical structure differs for each specified position, such as a point and a three-dimensional object.

The setting means 14 mainly includes a CPU 307. The setting means 14 refers to the structure information storage means 11, and extracts, as structures to be separated, plural anatomical structures present in a predetermined range from a specified position that has been specified by the specifying means 13. Further, the setting means 14 sets, based on a separation condition, a boundary surface corresponding to the extracted structures to be separated and the specified position that has been specified and, if necessary, a cutting surface.

The present invention is not limited to the first embodiment. When plural anatomical structures present within a predetermined range from the specified position are extracted as structures to be cut, such structures may be defined by using various judgment methods as long as it is possible to judge anatomical structures present in the predetermined range from the specified position.

For example, when the specified position is specified by using a point, an anatomical structure located in a range in which a distance between the point and a specific point on or within the anatomical structure is within a predetermined range may be defined as the structure to be cut. Alternatively, an anatomical structure including the point, which is the specified position, may be defined as the structure to be cut. When the specified position is specified by using a straight line, an anatomical structure located in a range in which a shortest distance between a point on the straight line and a specific point on or within the anatomical structure is within a predetermined range may be defined as the structure to be cut. Alternatively, an anatomical structure including a part or all of the specified straight line may be defined as the structure to be cut. When the specified position is specified by using a surface, an anatomical structure located in a range in which a shortest distance between the surface and a specific point on or within the anatomical structure is within a predetermined range may be defined as the structure to be cut. Alternatively, an anatomical structure including a part or all of the specified surface may be defined as the structure to be cut. When the specified position is specified by using a three-dimensional object, an anatomical structure located in a range in which a shortest distance between a point in the three-dimensional object and a specific point on or within the anatomical structure is within a predetermined range may be defined as the structure to be cut. Alternatively, an anatomical structure including a part or all of the specified three-dimensional object may be defined as the structure to be cut.

The setting means 14 determines, based on the aforementioned separation condition, a boundary surface or if necessary a cutting surface for each structure to be cut. The setting means 14 may set in such a manner that an anatomical structure is separately displayed only by a part of a boundary surface or a cutting surface. Alternatively, the setting means 14 may set in such a manner that an anatomical structure is separately displayed by all of a boundary surface or a cutting surface.

The separate image generation means 15 mainly includes a CPU 307. The separate image generation means 15 generates, based on the boundary surface and, if necessary, a cutting surface and three-dimensional medical data, a three-dimensional medical image in which a structure to be separated is separated by the boundary surface and, if necessary, the cutting surface, and makes a display means display the three-dimensional medical image.

In separate display in which plural anatomical structures, which are structures to be separated, are moved, the separate image generation means 15 calculates the position of each voxel of plural anatomical structures, which are structures to be separated, after movement. The separate image generation means 15 copies voxel values or the like, and reconstructs a three-dimensional medial image after separation. Here, known methods may be used to reconstruct a new three-dimensional medical image in which structures in the three-dimensional medical image are separately displayed by using three-dimensional medical image data. In the specification of the present application, the reconstructed three-dimensional medical image will be referred to as "separate image" in some cases. It is not necessary that the reconstructed image is displayed by the display means 16 immediately after generation of the reconstructed image. The reconstructed image may be displayed after being temporarily stored in a storage means, such as a hard disk, or after being sent or received through a network or the like.

Only a part of a boundary surface or a cutting surface of an anatomical structure may be moved parallel, or rotated and moved, and a three-dimensional medical image in which the anatomical structure is not separately displayed at a part of the boundary surface or the cutting surface may be reconstructed. In this case, a separate image may be generated by appropriately storing density values or the like of voxels into a portion connecting a portion that has been separated and a portion that has not been separated by using a known method, such as linear interpolation, if necessary.

It is desirable that the separate image is constructed further in such a manner that the position of an anatomical structure is movable and the anatomical structure is rotatable in the separate image by a known edit tool or the like, and that the scale and the color of a structure or the like included in the separate image are changeable. Further, it is desirable that the separate image is editable based on other various demands.

Next, with reference to FIGS. 3 to 5, the flow of image diagnosis support processing according to the first embodiment will be described using a specific example. FIG. 3 illustrates a separation condition table 170 in the first embodiment. FIG. 4A is a diagram illustrating a specified position in a liver according to the first embodiment. FIG. 43 is a diagram illustrating an example of a separate image of the liver in the first embodiment. FIG. 5 is a flow chart illustrating the flow of image diagnosis support processing in the first embodiment.

First, the specifying means 13 specifies a specified position (S101). As illustrated in FIG. 4A, the specifying means 13 includes a knife-type tool 131 for specifying a straight line. The knife-type tool 131 is a pointer for indicating a current input position by an input tool, such as a mouse, on an operation monitor screen of a computer, which is displayed on the display means 16. When a mode that enables setting of specified position in a three-dimensional medical image displayed by the display means 16 is selected, the knife-type tool 131 is displayed as a pointer in the three-dimensional medical image. A desired straight line 131A may be specified by the knife-type tool 131, for example, by specifying a start point in the three-dimensional medical image by a single click of a left button of a mouse at the start point and then by specifying an end point in the three-dimensional medical image by a single click of the left button of the mouse at the end point.

Next, the setting means 14 extracts, as an anatomical structure to be cut, an anatomical structure present in a predetermined range from the specified position (S102).

As illustrated in FIG. 4A, a straight line 13A is specified in the three-dimensional medical image representing a liver by an operation of the knife-type tool 131. A user operates the knife-type tool 131 by a mouse. A surface 13B that includes the straight line 13A and extends in a direction perpendicular to a display screen on the three-dimensional medical image is a specified position. Hereinafter, in the specification of the present application, a surface that is a specified position will be referred to as a specified surface in some cases. In FIG. 4A, a part of a right lobe 36 of a liver, a left lobe 37 of the liver, and blood vessels 38 in the liver is present within predetermined range d from the specified surface 13B. Therefore, the right lobe 36 of the liver, the left lobe 37 of the liver, and the blood vessels 38 in the liver are extracted as structures to be cut.

Further, the setting means 14 refers to the separation condition table 170, and sets a boundary surface and, if necessary, a cutting surface based on the anatomical structure and the specified position (S103).

FIG. 3 illustrates an example of the separation condition table 170 about anatomical structures in a subject. In the example illustrated in FIG. 3, a boundary surface or, if necessary, a cutting surface, which includes a movement direction and a movement amount, is related to each anatomical structure based on a specified position for separating the anatomical structure. As FIGS. 3 and 4A illustrate, with respect to the right lobe 36 of the liver, the setting means 14 sets, based on the separation condition table 170, the contour of the right lobe 36 of the liver, as a boundary surface. Further, the setting means 14 sets no movement of the right lobe 36 of the liver. With respect to the left lobe 37 of the liver, the setting means 14 sets the contour 371 of the left lobe 37 of the liver, as a boundary surface. Further, the setting means 14 sets a movement distance of $d_{37}$ in a direction perpendicularly away from the specified surface 13B. With respect to the blood vessels 38 in the liver, the setting means 14 sets the contour 381 of the blood vessels 38 in the liver, as a boundary surface. Further, the setting means 14 sets no movement of the contour 381 of the blood vessels 38 in the liver. Here, a movement condition may be stored in a movement condition storage means composed of a storage means, such as a hard disk, separately from the separation condition. For example, a movement amount and a movement direction may be stored for each anatomical structure. In the aforementioned step S103, the setting means 14 may set a boundary surface and, if necessary, a cutting surface, and also set a movement condition corresponding to each anatomical structure by separately referring to the movement condition storage means.

Next, the separate image generation means 15 reconstructs a three-dimensional medical image that is a separate image, which has been moved based on the set movement condition, at the boundary surface or the cutting surface (S104). Finally, the display means 16 displays the reconstructed separate image (S105).

Figure 4B:
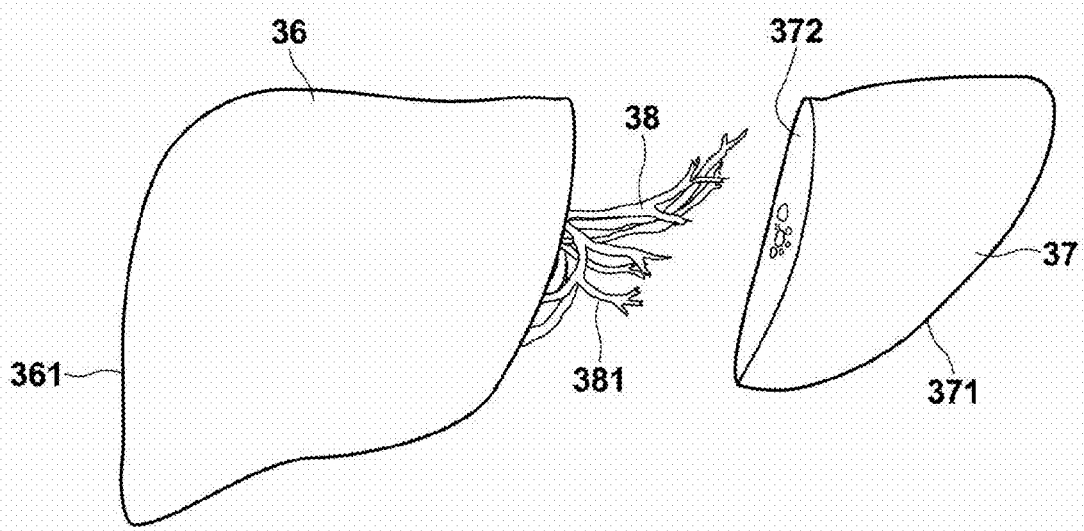
FIG. 4B an image diagram illustrating a separate image of a liver according to the first embodiment.

In the first embodiment of the present invention, a three-dimensional medical image as illustrated in FIG. 4B is reconstructed. In FIG. 4B, only the contour 371 of the left lobe 37 of the liver is set as a boundary surface, and the boundary surface 371 is perpendicularly moved, by $d_{37}$, in a direction away from the specified surface 13B to reconstruct and display the three-dimensional medical image. In the example illustrated in FIG. 4B, only the left lobe 37 of the liver is moved. Meanwhile, FIG. 4C is a modified example in which the right lobe 36 of the liver is also moved. In this modified example, the separation condition table 170 sets the contour 361 of the right lobe 36 of the liver, as a boundary surface, and movement of the right lobe 36 of the liver, by $d_{37}$, in the same direction as the movement of the left lobe 37 of the liver. The left lobe 37 of the liver and the right lobe 36 of the liver move, by the same distance, in the same direction. Further, the setting means 14 sets the contour 381 of the blood vessels 38 in the liver, as a boundary surface, and movement of the blood vessels 38 in the liver, by $d_{38}$, in a direction perpendicularly away from the selected surface 135. The blood vessels 38 in the liver move in an opposite direction to the movement direction of the left lobe 37 of the liver and the right lobe 36 of the liver.

Further, as another modified example, the separation condition may be set in such a manner that the contour of the left lobe 37 of the liver and the contour of the left lobe 37 of the liver are set as boundary surfaces, respectively, and moved in opposite directions from each other perpendicularly to the specified surface, and that the contour of the blood vessels 38 in the liver is set as a boundary surface, and not moved. Alternatively, the separation condition may be set in such a manner that a specified surface 13B traversing the left lobe 37 of the liver is set as a cutting surface only for the left lobe 37 of the liver. The boundary surface and, if necessary, the cutting surface may be set in various kinds of combination.

In the first embodiment, the movement condition that determines a movement amount and a movement direction of each anatomical structure is included in the separation condition for each anatomical structure of the subject. The movement condition may be stored in a movement condition storage means composed of a storage means, such as a hard disk, separately from the separation condition. Further, in the aforementioned step S104, the separate image generation means may refer to the movement condition storage means to determine the movement condition corresponding to each anatomical structure, and generate a separate image.

Next, various specific examples to which separate display of anatomical structures by the image diagnosis support apparatus 1 according to the present embodiment has been applied will be described.

Figure 6A:
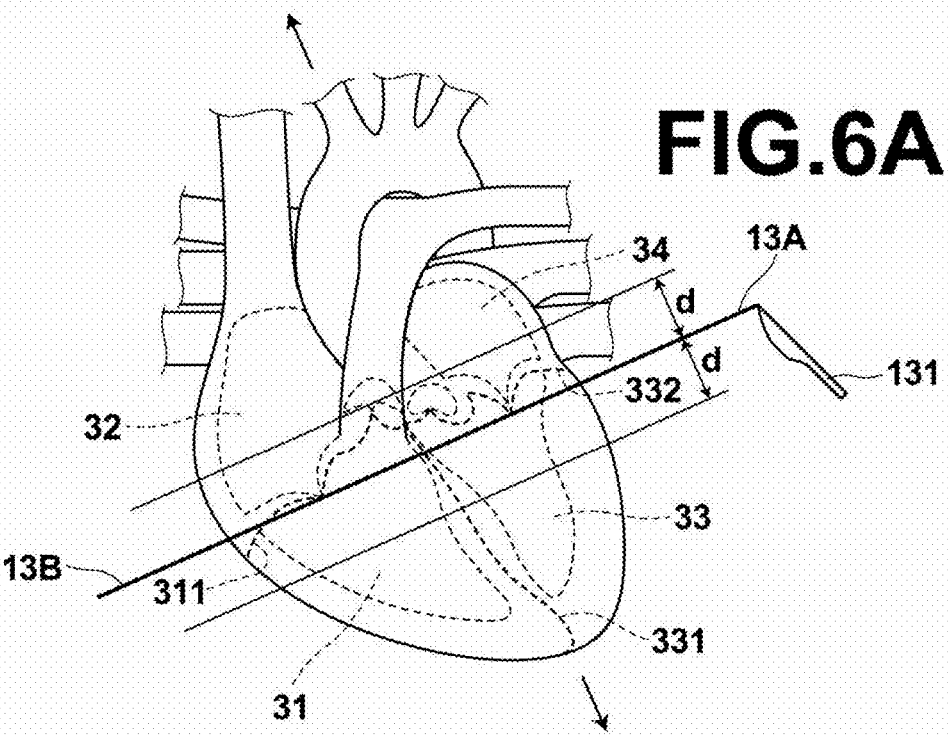
FIG. 6A an image diagram illustrating a method for specifying a position in a heart according to the first embodiment.
Figure 6B:
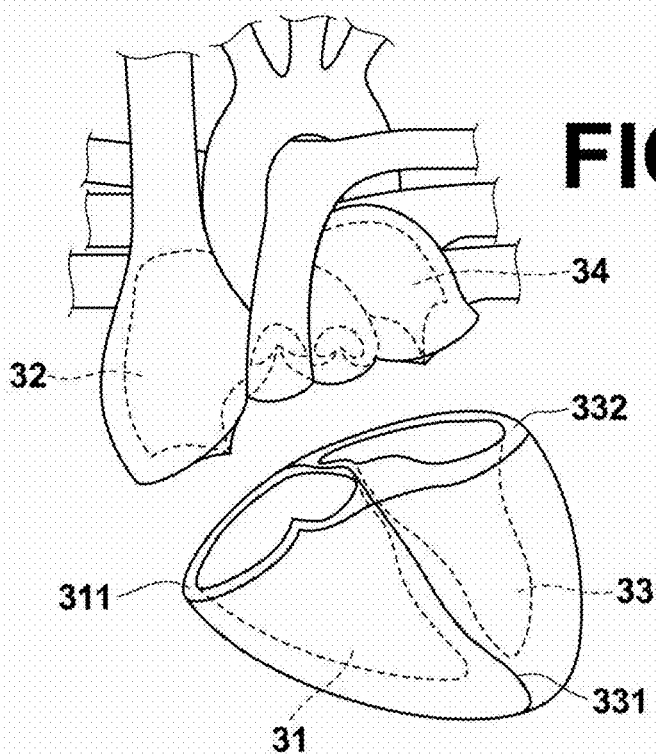
FIG. 6B an image diagram illustrating a separate image of a heart according to the first embodiment.

FIGS. 6A and 6B are diagrams illustrating an example of separate display of a heart according to an embodiment of the present invention. FIG. 6A is an image diagram of a three-dimensional medical image before separate display, and FIG. 6B is an image diagram of a separate image of the heart. In FIG. 6A, broken lines represent the internal contour of the heart. A contour 311 between a right ventricle 31 and a right atrium 32, a contour 331 between a right ventricle 31 and a left ventricle 33, and a contour 332 between the left ventricle 33 and a left atrium 34 are recognized in advance. Further, it is assumed that a contour between the right atrium 32 and the left atrium 34, which is not illustrated, is recognized by using known techniques as described already.

In FIG. 6A, a straight line 13A is specified by the knife-type tool 131, and the specified surface 13B, which is a specified position, is specified.

Next, the setting means 14 extracts, as structures to be cut, the right atrium 32, the right ventricle 31, the left atrium 34 and the left ventricle 33, a part of each of which is present in a range of predetermined distance d from the specified surface 13B (within predetermined range d).

Next, the setting means 14 refers to the separation condition table 170 illustrated in FIG. 3, and sets a movement amount and a movement direction for each of the right atrium 32, the right ventricle 31, the left atrium 34 and the left ventricle 33. Further, the setting means 14 sets contours of the right atrium 32, the right ventricle 31, the left atrium 34 and the left ventricle 33, as boundary surfaces, respectively.

Further, the separate image generation means 15 reconstructs a three-dimensional medical image that is a separate image by moving the boundary surface or the cutting surface based on the set movement condition. As illustrated in FIG. 68, both of the right atrium and the left atrium 34 are moved by distance $d_{32}$ ($d_{34}$) perpendicularly to the specified surface 13B. Further, both of the right ventricle 31 and the left ventricle 33 are moved by distance $d_{31}$ ($d_{32}$) perpendicularly to the specified surface 13B. Here, distance $d_{31}$ and distance $d_{32}$ are the same, and distance $d_{32}$ and distance $d_{34}$ are the same. Therefore, the left atrium 34 and the right atrium 32 are moved in the same direction (the direction of an arrow at an upper left side of FIG. 6A) by the same distance. Further, the right ventricle 31 and the left ventricle 33 are moved in the same direction (the direction of an arrow at a lower right side of FIG. 6A) by the same distance. Further, in the first embodiment of the present invention, the movement direction is based on the center of gravity of each anatomical structure, and the center of gravity of each anatomical structure moves in a direction away from the specified surface 13B. Finally, the display means 16 displays the separate image generated by the separate image generation means 15. At the end, a separate image of the heart, as illustrated in FIG. 6B, is displayed.

Figure 7:
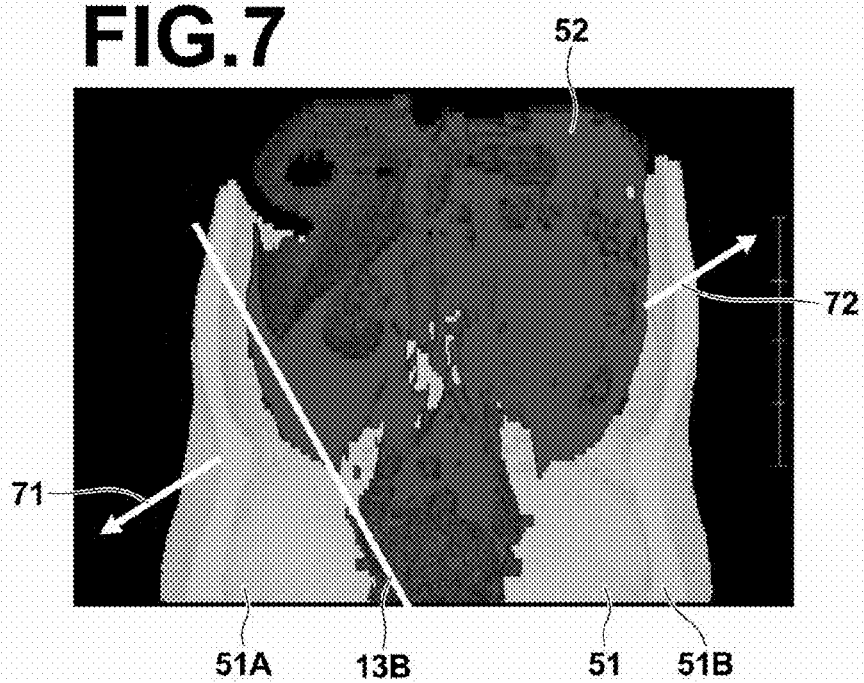
FIG. 7 a diagram illustrating an example of specifying a position to separate subcutaneous fat according to the first embodiment.

FIG. 7 is an image diagram illustrating an example of specifying a position for separating subcutaneous fat according to an embodiment of the present invention. In FIG. 7, the specifying means 13 specifies a specified surface 13B in a similar manner to already described examples. The setting means 14 refers to the separation condition table 170, and sets the specified surface 13B as a cutting surface for subcutaneous fat 51. Further, the setting means 14 sets in such a manner that subcutaneous fat 51A of the subcutaneous fat 51, which is segmented into the subcutaneous fat 51A and subcutaneous fat 515 by the specified surface 13B, is moved by movement distance $d_{51}$ in a direction (the direction of arrow 71) in which the subcutaneous fat 51A moves perpendicularly away from the specified surface 13B, and that the subcutaneous fat 51B of the subcutaneous fat 51 is moved by movement distance $d_{51}$ in a direction (the direction of arrow 72) in which the subcutaneous fat 51B moves perpendicularly away from the specified surface 13B, and that a contour of visceral fat 52 is a boundary surface, and the visceral fat 52 is not moved. The separate image generation means 15 generates a separate image in which the subcutaneous fat 51A is moved in the direction of arrow 71, and the subcutaneous fat 51B is moved in the direction of arrow 72, and the visceral fat 52 is not moved. Further, the separate image generation means 15 makes the display means 16 display the separate image. Here, the direction in which the subcutaneous fat 51A, 51B moves perpendicularly away from the specified surface 13B is based on the center of gravity of the subcutaneous fat 51A or 51B, and the center of gravity of the subcutaneous fat 51A or 51B moves away from the specified surface 13B.

Figure 8:
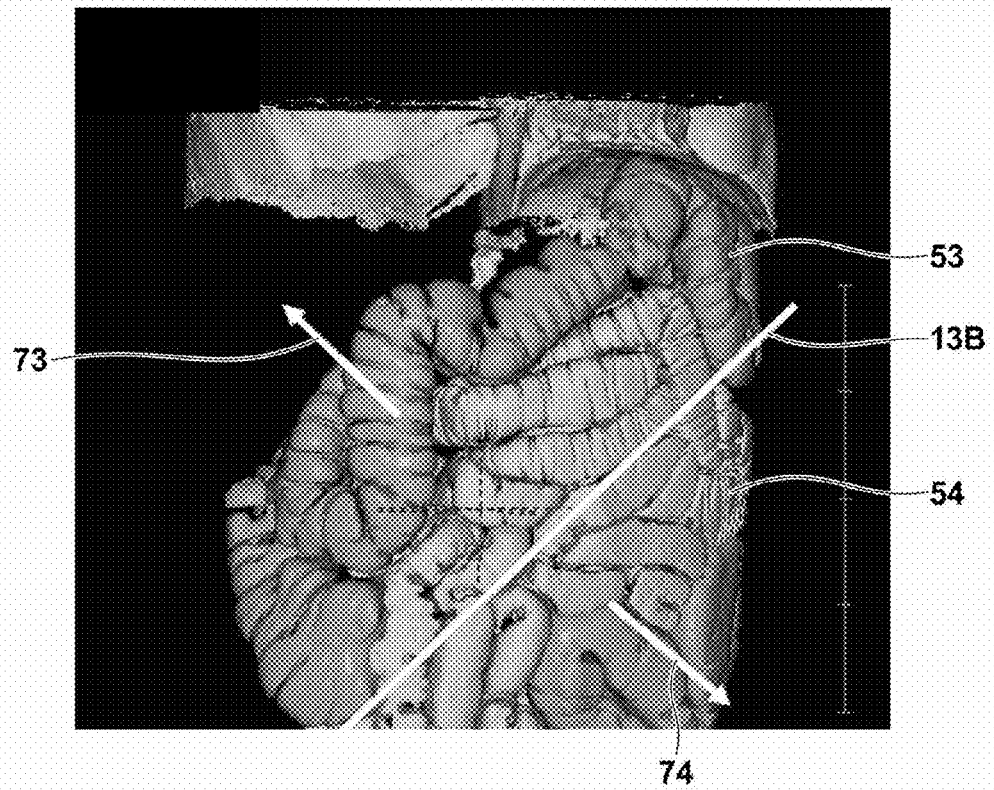
FIG. 8 a diagram illustrating an example of specifying a position in intestines according to the first embodiment.

FIG. 8 is an image diagram of an example of specifying a position in intestines in an embodiment of the present invention. In FIG. 8, the specifying means 13 specifies a specified surface 13B. The setting means 14 refers to the separation condition table 170, and sets, as a boundary surface, a contour of a large intestine 53 for the large intestine 53. Further, the setting means 14 sets, as a boundary surface, a contour of a small intestine for the small intestine 54. The setting means 14 sets a movement direction (the direction of arrow 73) of the large intestine 53, in which the large intestine 53 moves away from the specified surface 13B, a movement direction (the direction of arrow 74) of the small intestine 54, in which the small intestine 54 moves away from the specified surface 13B, movement distance $d_{53}$ of the large intestine 53, and movement distance $d_{54}$ of the small intestine 54. The direction in which the large intestine 53 or the small intestine 54 moves away from the specified surface 13B is judged based on the center of gravity of an anatomical structure in a similar manner to the aforementioned example of subcutaneous fat. Further, the separate image generation means 15 generates a separate image in which the large intestine 53 has been moved by the movement distance $d_{53}$ in the direction of arrow 73 and the small intestine 54 has been moved by the movement distance $d_{54}$ in the direction of arrow 74 in a similar manner to the aforementioned example. Further, the separate image generation means 15 makes the display means 16 display the separate image.

As described above, the image diagnosis support apparatus according to the present embodiment sets, based on a specified position, a boundary surface and, if necessary, a cutting surface for each structure. Therefore, it is possible to automatically set an appropriate boundary surface and, if necessary, an appropriate cutting surface based on the specified position for each of plural anatomical structures. Further, it is possible to more flexibly display a three-dimensional medical image that is separated based on a desired position appropriate for the purpose of diagnosis by a simple operation of only specifying the desired position. Hence, it is possible to more effectively support image diagnosis.

In the example of separately displaying the blood vessels in the liver constituting a part of the right lobe 36 and the left lobe of the liver in the first embodiment, the separation condition about a predetermined anatomical structure constituting a part of another anatomical structure of plural anatomical structures is set in such a manner to determine, as a boundary surface, a contour of the predetermined anatomical structure. When the separation condition is set in such a manner, even if the other anatomical structure is displayed in such a manner to be separated by a boundary surface or a cutting surface, the predetermined anatomical structure is displayed without being separated by the boundary surface or the cutting surface, and the predetermined anatomical structure is displayed in such a manner that the contour of the predetermined anatomical structure is maintained. Therefore, it is possible to separately display each of the other anatomical structure and the predetermined anatomical structure constituting the other anatomical structure based on relative positions of the plural anatomical structures so that diagnosis on each of the anatomical structures is easily performed. Therefore, it is possible to effectively support diagnosis so that precise image diagnosis is possible. Further, as in the example of separately displaying the subcutaneous fat and the visceral fat in the first embodiment, when the separation condition about an anatomical structure enclosed by another anatomical structure is set in such a manner to determine, as a boundary surface, a contour of the anatomical structure, a similar effect is remarkable.

In the image diagnosis support apparatus according to the first embodiment of the present invention, it is possible to arbitrarily determine, in the separation condition, whether a specified surface traversing an anatomical structure is used as a cutting surface to separate, and whether a contour of an anatomical structure is used as a boundary surface to separate. Further, it is possible to easily display the anatomical structure that is separated by a boundary surface or, if necessary, a cutting surface based on a separation condition only by specifying a position by the specifying means 13. Therefore, it is possible to easily realize a demand for observing a cutting surface and a demand for separately displaying each anatomical structure. Hence, it is possible to effectively support image diagnosis.

As a modified example of the first embodiment, the image diagnosis support apparatus may further include a database that stores relative arrangement of anatomical structures by using various known methods. Further, the separation condition about an anatomical structure and an anatomical structure enclosed by the anatomical structure may be automatically set in such a manner that a surface specified by the specifying means 13 is used as a cutting surface for the outer-side anatomical structure and that a contour of the inner-side anatomical structure is used as a boundary surface. Further, the separation condition may be automatically set in such a manner that a contour of an anatomical structure constituting a part of another anatomical structure is used as a boundary surface, and that a surface specified by the specifying means 13 is used as a cutting surface for an anatomical structure constituting the other anatomical structure. Since it is possible to separately display images, step by step, without performing complicated setting of separation condition, it is possible to effectively support diagnosis based on images.

Further, as a modified example of the first embodiment, 4D display of the separate image may be performed so that plural anatomical structures are displayed in time series. In such a case, it is possible to display a temporal change in an anatomical structure at a desired boundary or cutting surface, and to support image diagnosis so that precise diagnosis is possible. For example, as illustrated in FIG. 4B, when the right lobe 36 of the liver, the left lobe 37 of the liver and the blood vessels 38 in the liver are separately displayed in a separate image of the liver, a contrast medium may be projected into the liver, and 4D display in which a change of the contrast agent in the liver in the separate image is displayed in time series may be performed. Further, 4D display may be performed in the state as illustrated in FIG. 6B, in which the heart is separated, so that motion of the heart can be checked in time series.

In a second embodiment of embodiments of the present invention, the separation condition according to the first embodiment further includes hierarchical display option. In the hierarchical display option, plural anatomical structures in which respective ranks of hierarchical display are set are displayed, step by step, from a low rank.

Figure 9A:
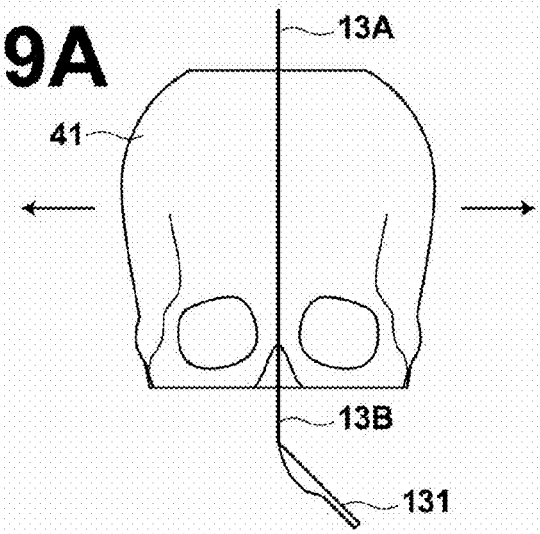
FIG. 9A a diagram illustrating an example of specifying a position in a head according to a second embodiment.
Figure 9B:
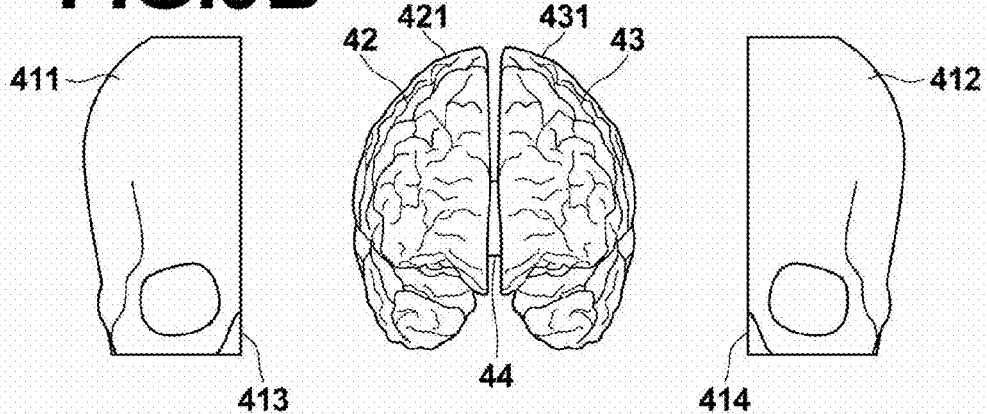
FIG. 9B an image diagram illustrating a separate image of a head according to the second embodiment (Rank 1)
Figure 9C:
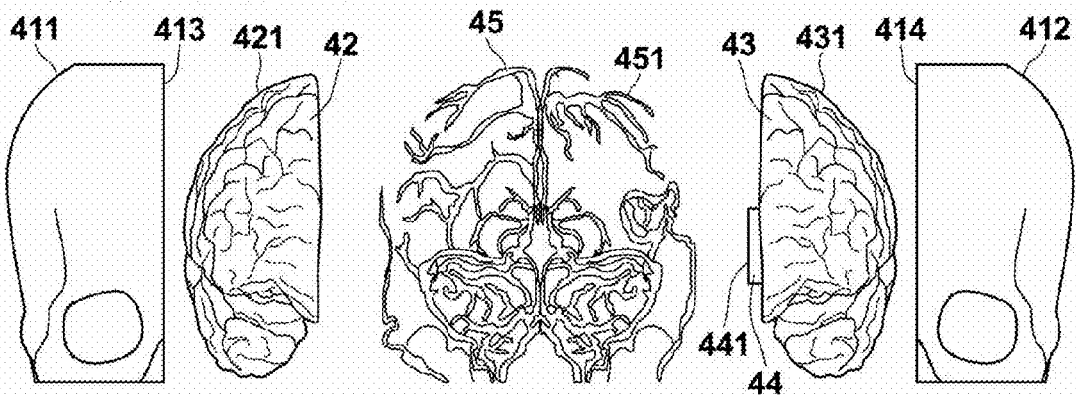
FIG. 9C an image diagram illustrating a separate image of a head according to the second embodiment (Rank 2)
Figure 11:
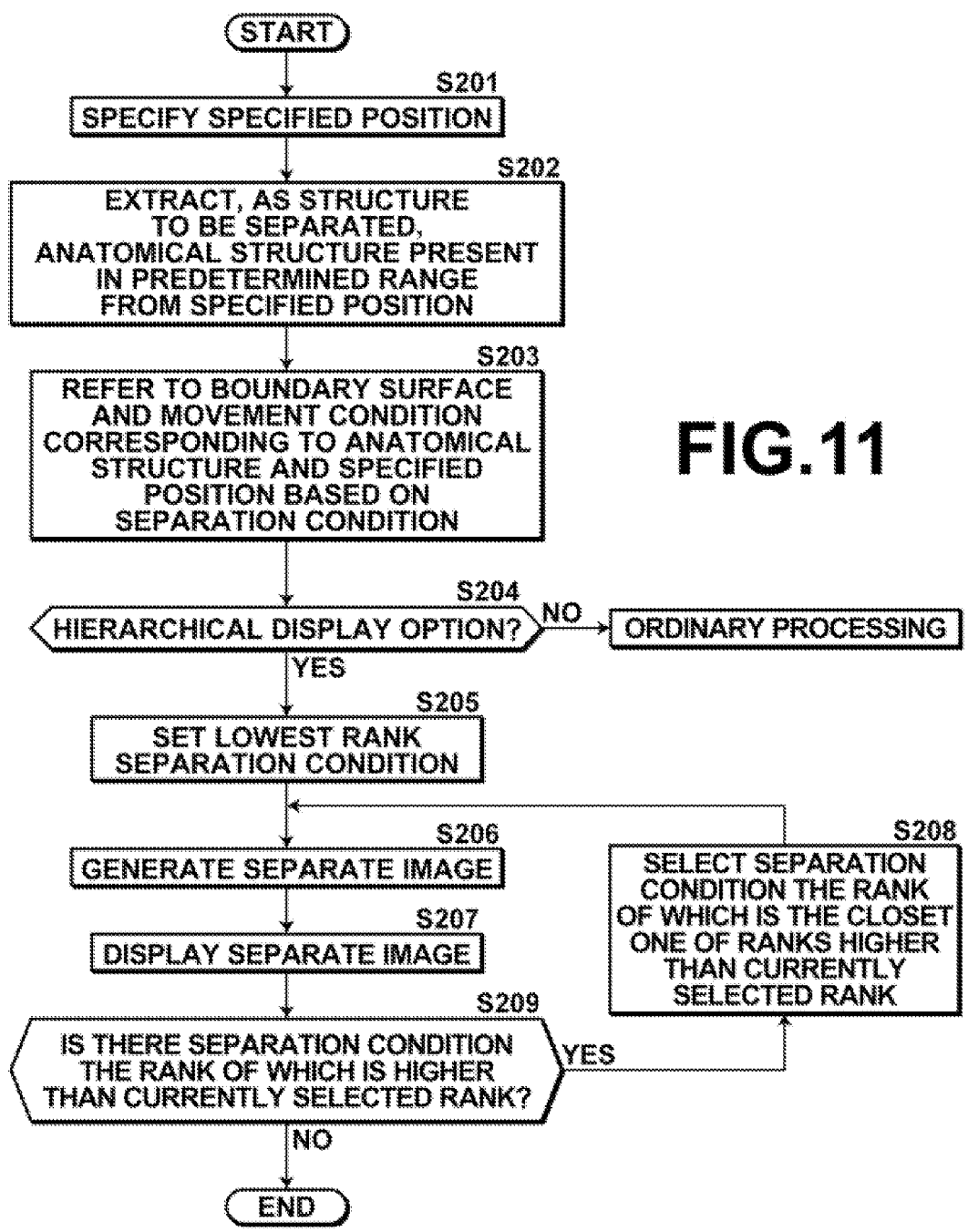
FIG. 11 a flow chart illustrating a flow of multi-layer display processing in the second embodiment.

FIGS. 9A through 9C are diagrams illustrating examples of hierarchical display of a head according to an embodiment of the present invention. FIG. 9A is an image diagram of a three-dimensional medical image of the head before separate display. FIG. 9B is a diagram illustrating an example of separate display of the head in rank 1 by hierarchical display option. FIG. 9C is a diagram illustrating an example of separate display of the head in rank 2 by hierarchical display option. FIG. 10 is a diagram illustrating a separation condition table 171 including examples of separation conditions with hierarchical display option. FIG. 11 is a flow chart representing a flow of processing of hierarchical display option by an image diagnosis support apparatus of the second embodiment.

Separate display processing by hierarchical display option will be described based on the flow chart illustrated in FIG. 11. Processing of S201 is similar to processing of S101, and processing of S202 is similar to processing of S102. Specifically, the specifying means 13 specifies a specified position (S201). Next, the setting means 14 extracts, as a structure to be cut, an anatomical structure present in a predetermined range from the specified position (S202). In the second embodiment, the setting means 14 extracts, as structures to be cut, cranial bones 41, a right cerebral hemisphere 42, a left cerebral hemisphere 43, a corpus callosum 44 and blood vessels 45 in a cerebrum, which are present in a predetermined range from a specified surface 13B. The specified surface 13B includes a straight line 13A specified by a knife-type tool 131, and the specified surface 13B is perpendicular to a display screen illustrated in FIG. 9A. Next, the setting means 14 refers to the separation condition table 171, and refers to a boundary surface, and if necessary, a cutting surface based on an anatomical structure and a specified position (S203).

Then, whether hierarchical display option has been set in the separation condition is checked (S204). As illustrated in the column of option in FIG. 10, the separation condition table 171 sets hierarchical display option for the cranial bones 41, the right cerebral hemisphere 42, the left cerebral hemisphere 43, the corpus callosum 44 and the blood vessels 45 in the cerebrum 1. Further, a movement condition and a boundary surface or a cutting surface for separating an anatomical structure are related to each rank of each anatomical structure. For example, a movement condition and a boundary surface or a cutting surface for separating an anatomical structure that are used in display of rank 1, and a movement condition and a boundary surface or a cutting surface for separating an anatomical structure that are used in display of rank 2 are separately set for the right cerebral hemisphere 42.

When the column of option is checked, if hierarchical display option is not set, ordinary separate image display processing in S103 through S105, as described in the first embodiment, is performed (S204 is N). When the column of option is checked, if hierarchical display option is set, the movement condition and the boundary surface or the cutting surface for separating the anatomical structure at the lowest rank are set (S205). In other words, a movement condition and a boundary surface or a cutting surface for separating an anatomical structure at rank 1 are set for each of the left cerebral hemisphere 43, the right cerebral hemisphere 42, the corpus callosum 44 and the blood vessels 45 in the cerebrum based on the separation condition table 171 illustrated in FIG. 10. Specifically, with respect to the left cerebral hemisphere 43, the right cerebral hemisphere 42, the corpus callosum 44 and the blood vessels 45 in the cerebrum, a contour of an anatomical structure is set as a boundary surface, and a movement amount (movement distance) is set to 0 (zero), and a movement direction is set as no setting. The cranial bones 41 are segmented to cut segments 411, 422 by a cutting surface. Further, a movement condition and a boundary surface or a cutting surface for separating an anatomical structure are set for each of the cut segments. With respect to the cut segment 411, a surface 413, in which a specified surface 13B traverses the cranial bones 41, is set as a cutting surface, and movement by movement amount (movement distance) $d_{41}$ in a direction away from the specified surface 13B is set. With respect to the cut segment 412, a surface 414, in which a specified surface 13B traverses the cranial bones 41, is set as a cutting surface, and movement by movement amount (movement distance) $d_{41}$ in a direction away from the specified surface 13B is set.

Next, the separate image generation means 15 reconstructs a three-dimensional medical image that is a separate image moved at a boundary surface or a cutting surface based on a set movement condition (S206). Finally, the display means 16 displays the separate image generated by the separate image generation means 15 (S207). Processing of S205 is similar to processing of S104, and processing of S206 is similar to processing of S105. As illustrated in FIG. 9B, an image is displayed based on the separation condition at rank 1 for each anatomical structure that has been set by the setting means 14. Only the cranial bones 41 are segmented into cut segments 411, 412 by using surfaces 413, 414, as cutting surfaces, and each of the cut segments 411, 412 is moved by movement amount (movement distance) $d_{41}$ in a direction away from the specified surface 13B. The left cerebral hemisphere 43, the right cerebral hemisphere 42, the corpus callosum 44 and the blood vessels 45 in the cerebrum are not moved.

Next, the setting means 14 checks the separation condition table 171 as to whether any rank higher than rank 1, which is currently displayed, has been set for each anatomical structure (S209). When plural ranks have been set (S209 is Y), separation condition and a boundary surface or a cutting surface for separating an anatomical structure at the lowest one of ranks higher than the current rank are set. In other words, the separation condition and the boundary surface or the cutting surface for separating an anatomical structure at a rank closest to the current rank are set (S208). Here, step of S208 is performed as long as setting at a higher rank remains for a part of anatomical structures to be cut. In this case, a separation condition at a current rank is maintained for an anatomical structure to be cut without any higher rank setting.

With respect to the cranial bones 41, the right cerebral hemisphere 42, the left cerebral hemisphere 43 and the corpus callosum 44, a condition up to rank 2 has been set. Therefore, separation information and a boundary surface or a cutting surface for separating an anatomical structure at rank 2 are set for each of the structures. With respect to the blood vessels 45 in the cerebrum, only rank 1 is set. Therefore, separation information and a contour, as a boundary surface for separating, at rank 1 are set. Setting is performed based on the separation condition table 171 illustrated in FIG. 10. Specifically, the cranial bones 41 are segmented to cut segments 411, 422 by using, as cutting surfaces, surfaces 413, 414 in which a specified surface 13B traverses the cranial bones 41. Further, movement of each of the cut segments 411, 422 by movement amount (movement distance) $d_{411}$ in a direction away from the specified surface 13B is set. With respect to the left cerebral hemisphere 43, a contour of the left cerebral hemisphere 43 is set as a boundary surface, and movement by movement amount (movement distance) $d_{43}$ in a direction away from the specified surface 13B is set. With respect to the right cerebral hemisphere 42, a contour of the right cerebral hemisphere 42 is set as a boundary surface, and movement by movement amount (movement distance) $d_{42}$ in a direction away from the specified surface 13B is set. With respect to the corpus callosum 44, a contour of the corpus callosum 44 is set as a boundary surface, and movement by movement amount (movement distance) $d_{44}$ in a direction away from the specified surface 13B is set. With respect to the blood vessels 45 in the cerebrum, an movement amount (movement distance) is set to 0 (zero), and a movement direction is set to no setting. In the second embodiment, a direction perpendicularly away from a specified surface 13B is a direction in which the center of gravity of an anatomical structure moves perpendicularly away from the specified surface 13B. Further, it is assumed that the center of gravity of the left cerebral hemisphere 43 and the center of gravity of the corpus callosum 44 are present on the same side of the specified surface 13B, and that the movement distance $d_{43}$ and the movement distance $d_{44}$ are set at the same distance.

The separate image generation means 15 reconstructs, based on the movement condition and the boundary surface or the cutting surface for separating an anatomical structure at rank 2, a three-dimensional medical image that is a separate image at rank 2, which is moved at the boundary surface or the cutting surface based on the set movement condition (S205). Further, the display means 16 displays the separate image at rank 2 generated by the separate image generation means 15 (S206). As illustrated in FIG. 9C, a movement amount (movement distance) of the right cerebral hemisphere 42 is 0 (zero) at rank 2. Therefore, the right cerebral hemisphere 42 is displayed without being moved. Meanwhile, the left cerebral hemisphere 43 and the corpus callosum 44 are moved by the same distance $d_{43}$ ($d_{44}$) toward the right side of the display screen, and displayed. Further, the right cerebral hemisphere 42 is moved by distance $d_{42}$ toward the left side of the display screen, and displayed. Each of the cut segments 411, 422 of the cranial bones 41 is moved by distance $d_{411}$, which is longer than the movement distance at rank 1, away from the specified surface 13B, and displayed.

Next, the setting means 14 checks the separation condition table 171 as to whether any rank higher than rank 2, which is currently displayed, has been set for each anatomical structure (S209). When a higher rank than rank 2 is set for no anatomical structure of the structures to be cut in the separation condition table 171 (S209 is N), processing ends. As illustrated in FIG. 10, a higher rank than rank 2 is set for no anatomical structure of the structures to be cut in the separation condition table 171. Therefore, processing ends.

The present invention is not limited to the second embodiment of the present invention. The hierarchical display option may be realized by using various known methods as long as it is possible to set a separation condition for each anatomical structure and for each rank. In the second embodiment, a case of displaying a separate image of each rank immediately after generation of the separate image was described. However, it is not necessary that the separate image is displayed immediately after generation. The apparatus may be structured in such a manner that separate images are stored in a storage medium, such as a hard disk, and a selected rank may be displayed based on selection by a mouse or the like.

When the hierarchical display option is provided, it is possible to display, based on a purpose of diagnosis, a separate image of an anatomical structure at each set rank by a simple operation. Therefore, it is possible to efficiently support diagnosis using images.

The hierarchical display is especially effective for a separation condition about a predetermined anatomical structure present in another anatomical structure of plural anatomical structures. As in separate display of a head described at the beginning of the second embodiment, it is possible to separately display plural anatomical structures sequentially from an anatomical structure located on the outer side, or the like. It is possible to separately display plural anatomical structures, step by step, based on relative positions of the plural anatomical structures by a simple operation in such a manner to be appropriate for the purpose of diagnosis. Therefore, it is possible to efficiently support diagnosis using images.

Further, a storage means, such a database, that stores relative arrangement of anatomical structures by using various known methods may be further provided to set hierarchical display option of the separation condition. The database records relative positions of plural anatomical structures obtained by learning image data including a three-dimensional medical image representing the plural anatomical structures. The hierarchical display option may be automatically set for a boundary surface or a cutting surface for separating an anatomical structure in such a manner that different ranks are sequentially set from the outer-side anatomical structure toward the inner-side anatomical structure. Since it is possible to separately display, step by step, without setting complicated separation condition, it is possible to efficiently support diagnosis using images.

In a third embodiment of embodiments of the present invention, the separation condition includes partial separation option in which separate display is performed only at a part of a boundary surface.

Figure 12A:
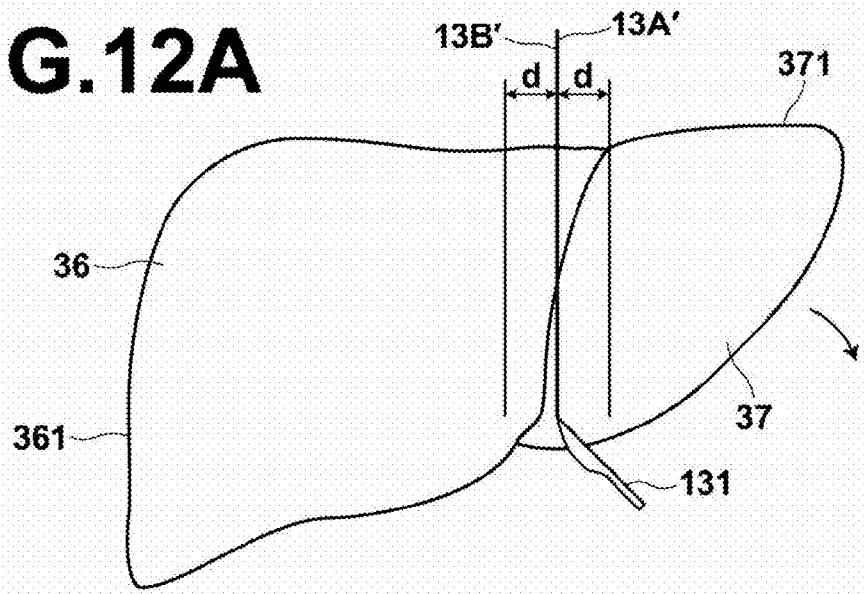
FIG. 12A a diagram illustrating an example of specifying a position in a liver according to the third embodiment.
Figure 12B:
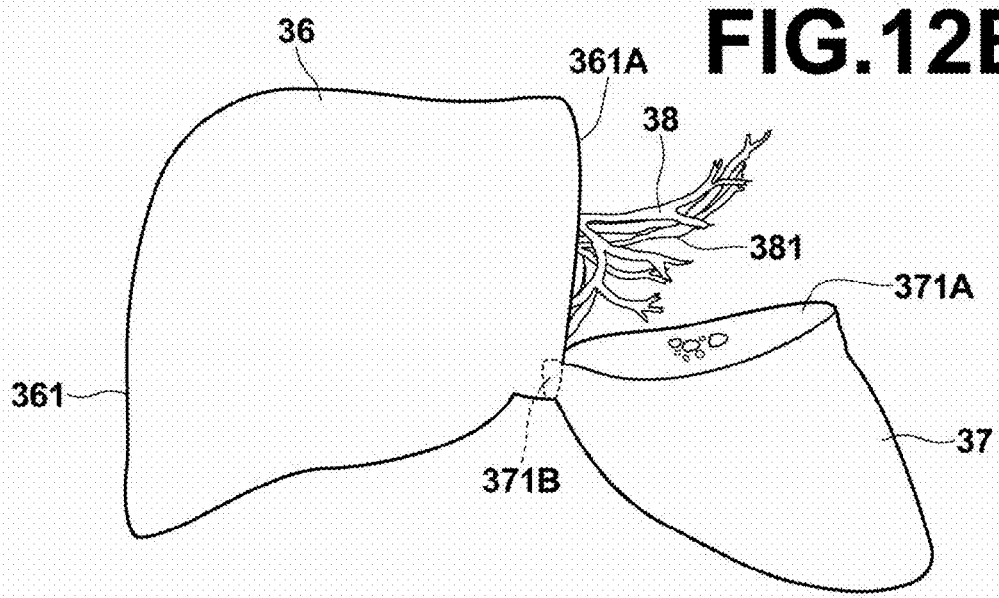
FIG. 12B an image diagram of a separate image of a liver according to the third embodiment.
Figure 13:
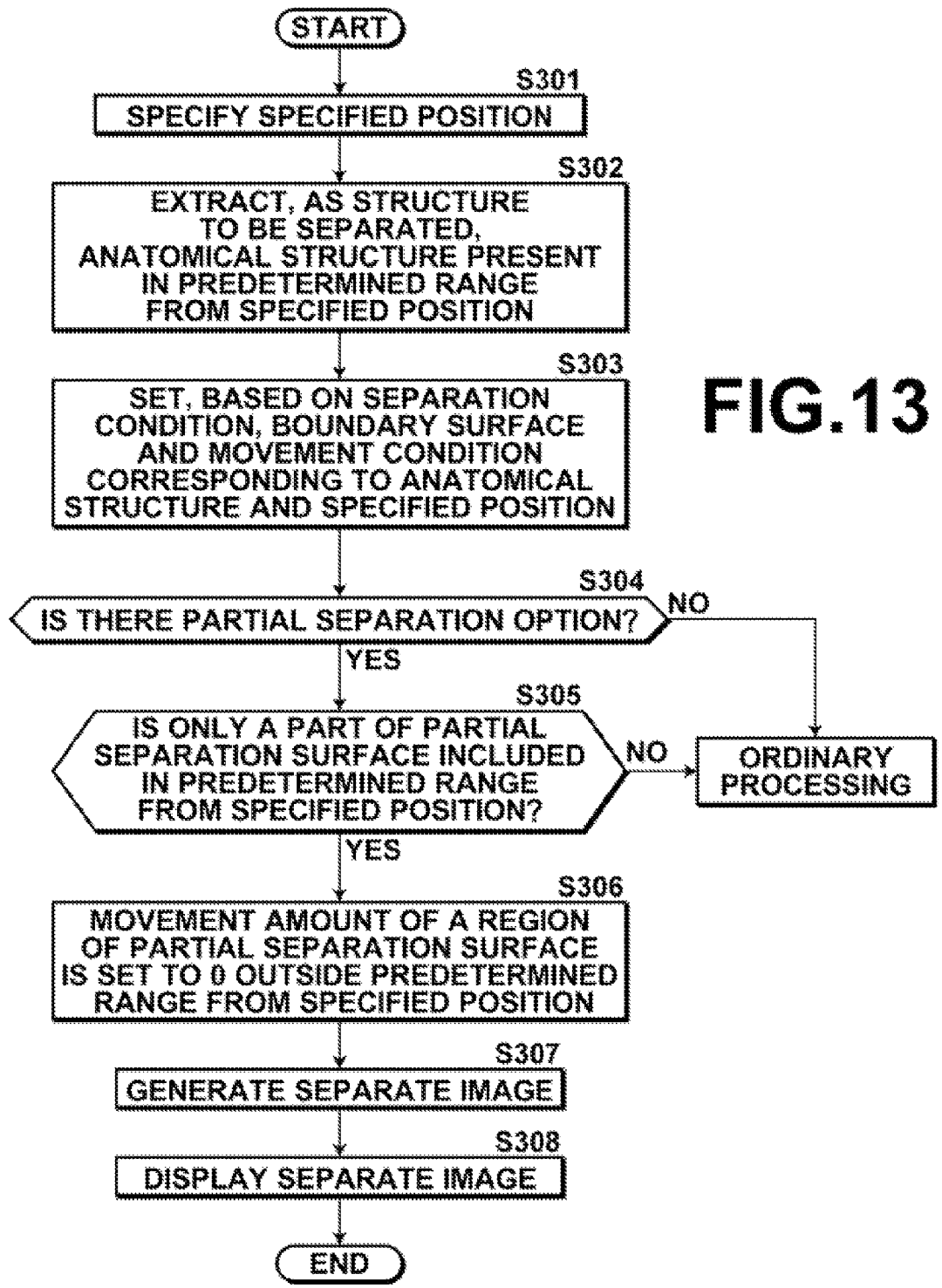
FIG. 13 a flow chart illustrating a flow of partial separate display processing according to the third embodiment.

FIGS. 12A, 12B are diagrams illustrating examples of separate display of a liver according to the third embodiment of the present invention. FIG. 12A is an image diagram of specifying a specified position for partial separate display in a three-dimensional medical image. FIG. 12B is an image diagram of separate display by the partial separate display option. FIG. 13 is a flow chart representing a flow of processing of partial separate display according to the third embodiment.

First, the partial separate display option in the separation condition will be described with reference to FIG. 12A. In the third embodiment of the present invention, straight line 13A' is specified by a knife-type tool 131 in a manner similar to the method described in the first embodiment with reference to FIG. 4A. Consequently, specified surface 13B' is specified. In contrast to FIG. 4A, the specifying means 13 specifies the straight line 13A' extending through the liver only to a certain point within the liver.

With reference to FIG. 13, processing for partial separate display according to the third embodiment will be described.

Processing of S301 is similar to processing of S101, and processing of S302 is similar to processing of S102. Specifically, the specifying means 13 specifies a specified position (S301). Next, the setting means 14 extracts, as a structure to be cut, an anatomical structure present in a predetermined range from the specified position (S302). Further, the setting means 14 refers to the separation condition table 171, and sets a movement condition, a boundary surface and, if necessary, a cutting surface based on the anatomical structure and the specified position (S303). Specifically, the setting means 14 extracts, as structures to be cut, the right lobe 36 of the liver, the left lobe 37 of the liver and blood vessels 38 in the liver. Further, the setting means 14 selects, for each anatomical structure, a movement condition, and a boundary surface or a cutting surface for separating the anatomical structure.

Next, the setting means 14 refers to the separation condition table 171 illustrated in FIG. 10, and checks whether partial separate option is set (S304). In the third embodiment of the present invention, partial separate display option is set only for the left lobe 37 of the liver. The setting means 14 sets, based on the separation condition table 171, a contour of the left lobe 37 of the liver as a boundary surface, and rotation, with respect to a predetermined center axis, by $r_{37}$ in a direction away from the right lobe 36 of the liver. The separation condition table 171 sets the same conditions as the separation condition table 170 as for the right lobe 36 of the liver and the blood vessels 38 in the liver. Therefore, the same movement condition and the same boundary surface for separating an anatomical structure as those of separate display processing in the first embodiment are set for the right lobe 36 of the liver and the blood vessels 38 in the liver.

Next, when partial separation option has been set for a structure to be cut (S304 is Y), the setting means 14 checks whether a predetermined range from the specified position includes only a part of a partial separation surface (S305). The partial separation surface is a surface at which only a part is separated and displayed. It is assumed that the partial separation surface has been set, in advance, in the column of option in the separation condition. Further, the partial separation surface is a surface adjacent to another anatomical structure. In the third embodiment of the present invention, a curved surface composed of a region 371A and a region 371B in the left lobe 37 of the liver is a partial separation surface. In the region 371A and the region 371B, the right lobe 36 of the liver and the left lobe 37 of the liver are adjacent to each other. In the third embodiment of the present invention, a relative distance between a surface 361A of the right lobe of the liver and the region 371A in the left lobe of the liver is changed, and partial separate display is performed.

When a predetermined range from the specified position includes only a part of a partial separation surface (S305 is Y), the setting means 14 extracts, based on the specified position, a region to be separately displayed and a region to be displayed without being separated from the partial separation surface. Further, the setting means 14 sets a movement condition so that the region to be separately displayed is displayed in such a manner to be relatively separated from another anatomical structure adjacent to the partial separation surface. Further, the setting means 14 sets a movement condition so that the region to be displayed without being separated is displayed in such a manner that a relative movement amount with respect to the other anatomical structure adjacent to the partial separation surface is zero (S306).

In the third embodiment, a movement amount of a region of a partial separation surface that is not located within a predetermined range from a specified position is set to zero. Further, a movement condition of a region of the partial separation surface that is located within the predetermined range from the specified position is set to a movement amount that is not zero. Specifically, according to the separation condition table 171, a curved surface constituting a contour 371 of the left lobe 37 of the liver adjacent to the right manner 36 of the liver is set as a partial separation surface, as illustrated in FIGS. 10 and 12A. A region 371A of the contour 371 is located within predetermined range d from the specified surface 13B, and a movement amount, i.e., a relative movement amount between the left lobe 37 of the liver and the right lobe 36 of the liver that is not zero and a movement direction are set for the region 371A. A region 371B of the contour 371 is not located within predetermined range d from the specified surface, and a condition that a movement amount, i.e., a relative movement amount between the left lobe 37 of the liver and the right lobe 36 of the liver is zero is set for the region 371B. With respect to the region 371A of the contour 371, which is a partial separation surface, a movement direction of rotating around a predetermined rotation axis and rotation by a predetermined angle $r_{36}$, as a movement amount, in a direction away from the right lobe 36 of the liver have been set. An arbitrary predetermined rotation axis may be determined. However, in the present embodiment, it is assumed that a straight line that passes a midpoint of a boundary line between the region 371B, which is not within a predetermined range from the specified surface, and the region 371A, which is within a predetermined range from the specified surface, and that extends from the display screen of the three-dimensional medical image perpendicularly toward the depth direction of the display screen is set as the rotation axis. A view point of FIG. 12B differs from a view point of FIG. 12A so that the region 371A is easily recognizable.

In partial separate display, it is desirable that a movement direction and a movement amount of an anatomical structure in which a partial separation surface has been set is set so that the partial separate image is easily recognized. For example, in a modified example of this example, a rotation axis may be slightly inclined from a direction extending from the display screen of the three-dimensional medical image toward the depth direction of the display screen, and the left lobe 37 of the liver may be rotated by predetermined angle $r_{36}$ so that the partial separation surface is recognized in the display screen.

When partial separation option has not been set for the structure to be cut (S304 is N), or when all of the partial separation surface is included in a predetermined range from the specified position (S305 is N), ordinary separate display processing as described in the first embodiment is performed. Since the separation condition table 171 sets the partial separation option neither for the right lobe 36 of the liver nor for the blood vessels 38 in the liver, ordinary separate display processing as described in the first embodiment is performed.

Next, the separate image generation means 15 reconstructs a three-dimensional medical image that is a separate image obtained by movement, based on the set movement condition, at the boundary surface or the cutting surface (S307). Finally, the display means 16 displays the separate image generated by the separate image generation means 15 (S308). Processing in S307 is similar to processing in S104, and processing in S308 is similar to processing in S105.

As described above, when partial separate display option is provided, and the separation condition determines the boundary surface so that only a desired part of an anatomical structure is separately displayed, it is possible to separately display the anatomical structure by separating only a part of the anatomical structure based on the purpose of diagnosis. Accordingly, it is possible to separately display the anatomical structure in such a manner that the cutting surface or the boundary surface of the anatomical structure only in the desired region is easily observable. Further, it is possible to display the inside of the structure in such a manner that the inside of the structure is easily observable from the boundary surface or the cutting surface. Further, it is possible to prevent more than necessary separation of the anatomical structure. Consequently, it is possible to prevent observation of the separate image from becoming difficult. Hence, it is possible to effectively support diagnosis based on an image.

The present invention is not limited to the third embodiment. The partial separate surface may be either a boundary surface or a cutting surface. Further, plural partial separation surfaces may be set in an anatomical structure. Alternatively, a single partial separation surface may be structured in such a manner that plural regions to be separated can be set. It is possible to display the three-dimensional medical image in such a manner that the three-dimensional medical image is partially separated at a more desirable position. Therefore, it is possible to effectively support diagnosis based on an image.

A region to be separated may be set in advance. However, it is more desirable that the specifying means 13 can specify a region to be separated. When the region to be separated is set in advance, it is possible to separately display a partial region by a simple operation without selecting a region to be separated by the specifying means 13. When the specifying means 13 can select a region to be separated, it is possible to display the anatomical structure in such a manner that the anatomical structure is appropriately separated based on the purpose.

The present invention is not limited to the third embodiment. A region to be separated in a partial separation surface may be specified by using various methods for specifying a position. In the separation condition, a movement condition about a region to be separated and a region that is not separated may be set by using various methods as long as partial separate display is possible.

In a fourth embodiment of embodiments of the present invention, the specifying means 13 is configured in such a manner that an operation for specifying various positions is further possible.

As illustrated in FIG. 14, in the fourth embodiment, various position specifying tools are provided. The various position selection tools include knife-type tools 131, 132 for specifying a straight line, spoon-type tools 133, 134 for specifying a curved surface, syringe-type tools 135, 136 for specifying a cylinder, which is a three-dimensional object, a fist-type tool 137 for specifying a point, a disk-type tool 138 for specifying a surface segmented into a disk-shape region, and a Z-type tool 139 for specifying a zigzag line composed of three straight lines. The knife-type tool 131 is the same as the one described in the first embodiment. Further, multi-layer separation options corresponding to the knife-type tool 131, the spoon-type tool 133, and the syringe-type tool 135, respectively, are specifiable. The multi-layer separation options are selectable by the knife-type tool 132, the spoon-type tool 134, and the syringe-type tool 136. When these multi-layer separation option tools are used to specify, if separation conditions about plural anatomical structures to be cut include a condition in which multi-layer separation option has been set, multi-layer display is performed. These position specifying tools may be operated by any one of a mouse, a pen touch tool, and a touch panel.

Positions specified by various position specifying tools of the present embodiment will be described by using a specific example.

FIGS. 15 and 16 are image diagrams illustrating an operation for specifying the position of an abnormal region 56 in a large intestine according to an embodiment of the present invention. FIG. 15 is a diagram illustrating a specified position specified by the spoon-type tool 133. FIG. 16 is a diagram illustrating a specified position specified by the syringe-type tool 135.

The spoon-type tools 133, 134 are tools for displaying a desired anatomical structure in such a manner that the anatomical structure is separated by being scooped by a curved surface specified by the spoon-type tool 133. An operation of the spoon-type tools 133, 134 in the three-dimensional medical image can specify a surface that curves out toward one side of the surface like a spoon. As illustrated in FIG. 15, a curved surface 133A is specified as a specified position in such a manner that the curved surface 133A scoops an abnormal region 56 of the large intestine 53. The setting means 14 extracts, as a structure to be cut, the abnormal region 56 present in a predetermined range from the specified curved surface 133A on the concave side of the specified curved surface 133A. Here, it is assumed that a region in a contour 561 has been automatically extracted as the abnormal region 56 in advance. Further, as the separation condition table 171, illustrated in FIG. 10, shows, a movement direction of the abnormal region is set in the direction of an arrow in FIG. 15, and a movement distance $d_{56}$ is set.

The syringe-type tool 135 is a tool for separately displaying only an anatomical structure extracted, based on a specified position, as illustrated in FIG. 16. A cylinder 135D is specified as the specified position by perpendicularly moving a circle 135A at the leading end of the syringe, and the anatomical structure is extracted from another anatomical structure in such a manner to suck the anatomical structure. The setting means 14 extracts, as a structure to be cut, an abnormal region 56 that is an anatomical structure included in the inside of the specified cylinder 135D. Line 135B is an intersection line between the inside of the cylinder 135D and the surface of the large intestine 53 on the upper side of FIG. 16. Line 135C is an intersection line between the inside of the cylinder 135D and the surface of the large intestine 53 on the lower side of FIG. 16.

With respect to the abnormal region 56, the setting means 14 sets, based on the separation condition table 171 illustrated in FIG. 10, a contour 561 of the abnormal region 56 as a boundary surface. Further, the setting means 14 sets, as a movement direction, a direction in which the circle 135A at the leading end of the syringe is moved by the specifying means 13. Specifically, the setting means 14 sets, as a movement direction, a direction from a start specifying position of the cylinder 135D to an end specifying position of the cylinder 135D with respect to the center of the circle 135A at the leading end of the syringe-type tool 135. The separate image generation means 15 generates a separate image by moving, by movement distance $d_{56}$ to be set, the abnormal region 56 at the contour 561 in the direction of an arrow illustrated in FIG. 16. Further, the separate image generation means 15 makes the display means 16 display the generated image.

When the specifying means specifies the specified position in a three-dimensional medical image by limiting a predetermined region by a curved line or a three-dimensional object, it is possible to extract, as a structure to be cut, only a region based on the predetermined region. Therefore, an anatomical structure that does not need to be separated is not separated, and only an anatomical structure that needs to be separated is separately displayed. Hence, it is possible to prevent generation of a separate image in which plural structures that do not need to be separated are separated, and to prevent observation of an image from becoming difficult. Consequently, a separate image is efficiently visualized.

Figure 17:
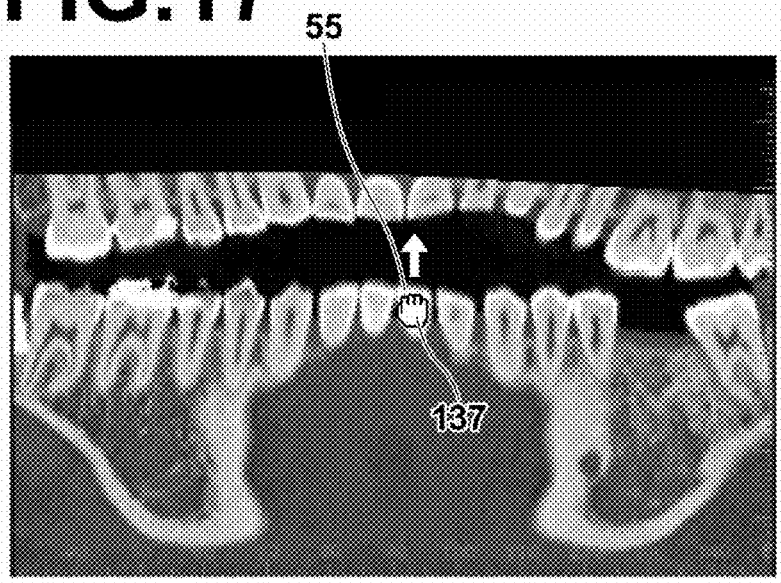
FIG. 17 a diagram illustrating an example of specifying a position of a tooth according to the fourth embodiment (specified by point)

With respect to the fist-type tool 137, a point specified by the fist-type tool 137 is a specified position. FIG. 17 is an image diagram illustrating an example of an operation for specifying a position of a tooth according to an embodiment of the present invention. The setting means 14 extracts, as a structure to be cut, a tooth 55 present in a predetermined range from the specified point. The setting means 14 uses a contour of a tooth as a boundary surface based on the separation condition table 171 illustrated in FIG. 10. Further, the setting means 14 moves the boundary surface, by $d_{55}$, in a direction (the direction of an arrow in FIG. 17) from the center of gravity of the tooth toward the specified point. When a method for specifying a specified position by using a point is used, it is possible to easily specify a very small anatomical structure, and that is desirable.

Figure 18:
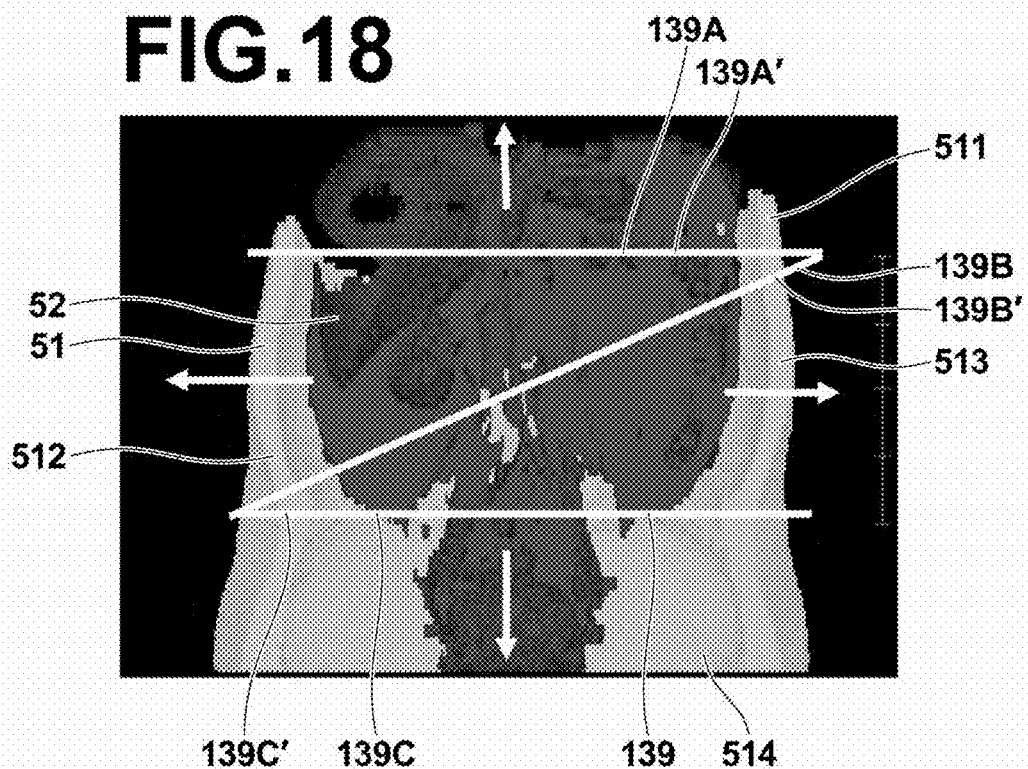
FIG. 18 a diagram illustrating an example of specifying a position in subcutaneous fat according to the fourth embodiment (specified by Z)

FIG. 18 is an image diagram illustrating an example of an operation for specifying a position of subcutaneous fat according to an embodiment of the present invention. The Z-type tool 139 can specify a zigzag line composed of three straight lines 139A, 139B and 1390 that are connected to each other in Z shape, as illustrated in FIG. 18. Specified positions are three planes, i.e., surfaces 139A', 139B' and 139C'. The surface 139A' includes the straight line 139A and extends in a direction perpendicular to a display screen on the three-dimensional medical image. The surface 139B' includes the straight line 139B and extends in a direction perpendicular to the display screen on the three-dimensional medical image. The surface 139C' includes the straight line 139C and extends in a direction perpendicular to the display screen on the three-dimensional medical image.

When the Z-type tool 139 has specified positions, a movement condition and a boundary surface or, if necessary, a cutting surface are set for each of four regions segmented by the surfaces 139A', 139B' and 139C' constituting the Z shape.

The setting means 14 extracts an anatomical structure that is present in a predetermined range from each of the specified surfaces 139A', 139B' and 139C'. Consequently, subcutaneous fat 51 and visceral fat 52 are extracted as structures to be cut. A separation condition table that is not illustrated sets, as a boundary, a contour of the visceral fat 52, and no movement. With respect to the subcutaneous fat 51, the separation condition table sets, as a boundary, a cutting surface. Further, the separation condition table sets a different movement direction for each of plural regions 511, 512, 513 and 514 segmented by the Z-shaped specified positions. Further, the separation condition table sets the same movement distance $d_{51}$ for each of all the regions 511, 512, 513 and 514. Here, the four regions are segmented regions with respect to a midpoint of the line 139B, which is a straight line located in the middle of the Z shape, as a center. The region 511 is far from the center than the plane 139A'. The region 514 is far from the center than the plane 139C'. The region 512 is limited by the plane 139A' and the plane 139B'. The region 513 is limited by the plane 139B' and the plane 1390'.

The separation condition table sets, as a movement direction of the region 511, a direction (a direction toward the upper side of the display screen in FIG. 18) extending from the center perpendicularly toward the straight line 139A. The separation condition table sets, as a movement direction of the region 514, a direction (a direction toward the lower side of the display screen in FIG. 18) extending from the center perpendicularly toward the straight line 139C. The separation condition table sets, as a movement direction of the region 512, a direction (a direction toward the left side of the display screen in FIG. 18) extending from an end of the straight line 139A connected to the straight line 139B toward an unconnected end of the straight line 139A. The separation condition table sets, as a movement direction of the region 513, a direction (a direction toward the right side of the display screen in FIG. 18) extending from an end of the straight line 1390 connected to the straight line 139B toward an unconnected end of the straight line 139C.

The separate image generation means 15 generates a separate image, based on the separation condition table that is not illustrated. The separate image generation means 15 moves each of the regions 511, 512, 513 and 514, by $d_{51}$, toward the upper side of FIG. 18, toward the left side of FIG. 18, toward the right side of FIG. 18, and toward the lower side of FIG. 18, respectively. Further, the separate image generation means 15 makes the display means 16 display the separate image.

Regarding the disk-type tool 138, a movement direction is specified by the specifying means 13 in the three-dimensional medical image, and the disk-type tool 138 can be moved in the specified direction as if the tool is thrown. Directions from the front side of the three-dimensional medical image toward the depth direction of the three-dimensional medical image may be specified for the disk-type tool 138, and the directions are arbitrary directions with respect to the vertical direction and the horizontal direction of the three-dimensional medical image. A plane that is the path of the disk-type tool 138 is a specified position (specified surface). A movement condition based on the specified surface and a method for separate display are the same as the case of the knife-type tool.

Further, the specifying means 13 in the present embodiment is configured in such a manner that a position specifying tool that a user wants to use can be selected from many position specifying tools on GUI. As the method for selecting the position specifying tool, a selection method disclosed in Japanese Patent No. 4179661 may be appropriately used. Specifically, a cursor representing a position specifying tool is sequentially switched in the order of the knife-type tool 131, the knife-type tool 132, the spoon-type tool 133 and the spoon-type tool 134 by every click of the left button of a mouse, and a position specifying tool represented by the displayed cursor is selected. The method is appropriate because it is not necessary to display various selectable tools on GUI in a complicated manner, and the tools are switchable only by an operation by a mouse or the like, and the operation characteristic is high.

The present invention is not limited to the present embodiment. Various known methods are adoptable as long as the methods can select a position specifying tool. For example, as in a known method, a tool bar or a tool selection palette in which position specifying tools are selectably displayed may be displayed on GUI. Further, a position specifying tool may be selected by click of a mouse or the like with the cursor of the mouse placed on a position specifying tool that a user wants to use.

When such various methods for specifying a position are selectably provided for the specifying means 13, it is possible to specify a specified position at a desired position and with a desired shape. Therefore, it is possible to more accurately extract a structure to be cut, which is extracted based on the specified position. Further, it is possible to more accurately and easily perform separate display based on a purpose. The present invention is not limited to the fourth embodiment. Various position specifying tools are adoptable as long as the specifying means 13 is configured in such a manner that a position is specifiable by at least two of a point, a line, a surface and a three-dimensional object.

As illustrated in FIG. 14, the position specifying tool may be configured in such a manner that selection is possible by using the position specifying tool in combination with an edit tool or the like. Here, the image diagnosis support apparatus according to the present embodiment includes an edit tool that can further edit, on GUI, the position of an anatomical structure in the three-dimensional medical image before separation or the position of a separated anatomical structure after separate display. These edit tools are not always necessary. However, it is desirable that the edit tool is provided because it becomes easy to freely observe an anatomical structure in a three-dimensional image based on the purpose of diagnosis in medical fields. FIG. 14 illustrates one of examples, and an arrow tool 140, a rotation tool 141, and a magnifying glass tool 142 are provided. The arrow tool 140 can perform editing, such as selecting or moving an anatomical structure. The rotation tool 141 rotates the anatomical structure selected by the arrow tool or the like. The magnifying glass tool 142 changes the display size of the three-dimensional medical image before separation or after separation.

Figure 19:
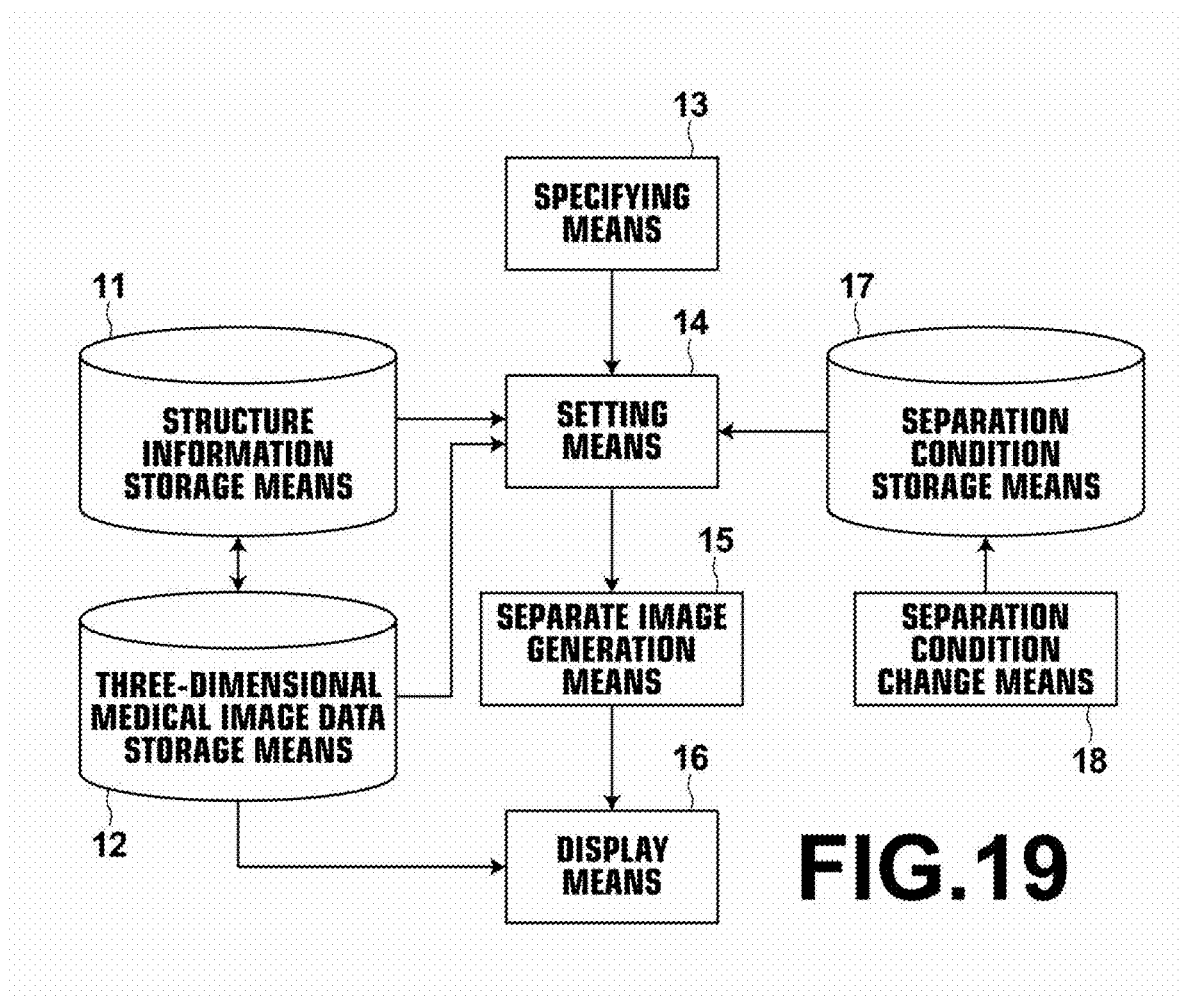
FIG. 19 a block diagram illustrating the configuration of an image diagnosis support apparatus according to a fifth embodiment.

With reference to FIGS. 19 and 20, a fifth embodiment of the present invention will be described. FIG. 19 is a schematic diagram illustrating the configuration of an image diagnosis support apparatus according to the fifth embodiment of the present invention. FIG. 20 is an image diagram illustrating an example of display on a display screen according to the fifth embodiment of the present invention.

The fifth embodiment differs from the image diagnosis apparatus of the first embodiment only in that a separation condition change means 18 is further provided in the fifth embodiment. The separation condition change means 18 receives a change of a separation condition in a three-dimensional medical image displayed by the display means 16, and changes a separation condition stored in the separation condition storage means. Therefore, descriptions on the same features as those of the first embodiment will be omitted.

The separation condition change means 18 mainly includes a CPU. The separation condition change means 18 receives a change of a separation condition by a user in an image displayed on the display means 16. FIG. 20 is a diagram illustrating, as an example, a display-screen display example 190 of the image diagnosis support apparatus according to the fifth embodiment. The display-screen display example 190 of the image diagnosis support apparatus of the fifth embodiment includes a separation condition change area 181 in which information in the separation condition table 170 is changeable. The separation condition change area 181 includes an anatomical structure selection box 182, a boundary surface selection box 183, a movement amount selection box 184, and a movement direction selection box 185. When a triangle button on the right side of the display screen is clicked in the anatomical structure selection box 182, an anatomical structure is selectable by a pull-down method. The boundary surface selection box 183 is used to select a boundary surface or a cutting surface for separating the selected anatomical structure. The movement amount selection box 184 can set a movement amount. When a triangle button on the right side of the display screen is clicked in the movement direction selection box 185, a movement direction is selectable by a pull-down method. In FIG. 20, a left lobe of a liver is selected as an anatomical structure, and a contour is selected as a boundary. Further, a distance of 4 mm from a specified surface on both sides of the specified surface is selected as the distance from the specified surface. Further, a direction perpendicularly away from the specified surface is selected as a movement direction. The present invention is not limited to the fifth embodiment. The separation condition change means 18 may adopt various known methods for receiving a change as long as the separation condition change means 18 is configured in such a manner that a separation condition is changeable.

As the display on a display screen of the image diagnosis support apparatus of the fifth embodiment, various known edit tools, buttons or the like may be further displayed. Further, the position specifying tool described in the fourth embodiment may be further displayed. It is assumed that a work area 191 for specifying a specified position in a three-dimensional medical image, various edit tools and the like are appropriately displayed in the display-screen display example 190, as an example. In FIG. 20, the display-screen display example 190 includes an original image display selection area 192, a separate image display selection area 193 and an area 194, as edit tools and the like. The original image display selection area 192 is used to display an original image in the work area 191. The separate image display selection area 193 is used to display a separate image in the work area 191. The area 194 can select storage or cancellation of a separate image and the content of an operation in an operation window.

As the fifth embodiment of the present invention shows, when the separation condition change means 18 that receives a change of a separation condition in a three-dimensional medical image displayed on the display means 16, and that changes a separation condition stored in the separation condition storage means is further provided, it is possible to flexibly change the separation condition based on the purpose of diagnosis. Therefore, it is possible to easily perform separate display in a desired manner. For example, after a user checks a generated separate image by using an input device, such as a mouse, the user can change a desired separation condition, and generate and display a new separate image. It is possible to flexibly generate a separate image of a three-dimensional medical image based on a user's demand any number of times until a desirable separate image is obtained. Therefore, it is possible to efficiently generate a separate image based on the medical purpose.

With reference to FIGS. 21 and 22, a sixth embodiment of the present invention will be described. FIG. 21 is an image diagram illustrating examples of a method for specifying a specified position and a method for displaying a separate image according to the sixth embodiment. FIG. 22 is a diagram illustrating an example of a separation condition table 172 of the sixth embodiment. The sixth embodiment differs from the first embodiment in that the separation condition further determines a rotation direction and a rotation amount for rotating and displaying an anatomical structure, and that the separate image generation means 15 generates a three-dimensional medical image by separating an anatomical structure based on the separation condition and by rotating the anatomical structure. Next, a femur 57 and a cervical bone 58 constituting a knee joint will be used as an example, and features of the sixth embodiment different from the first embodiment will be mainly described. Descriptions of the same features as the first embodiment will be omitted.

The specifying means 13 detects an operation of a mouse or the like by a user, and specifies a specified surface 13B in the display screen by the knife-type tool 131 in a manner similar to the first embodiment, as illustrated on the left side of FIG. 21. The specified surface 13B is a surface extending from the straight line 13A orthogonally to the display screen. The setting means 14 extracts, as structures to be cut, the femur 57 and the cervical bone 58 that are anatomical structures extracted based on the specified position.

With respect to the femur 57, the setting means 14 sets, based on the specified surface 13B and the separation condition table 172 illustrated in FIG. 22, a contour 571 of the femur 57 as a boundary surface for the femur 57. Further, the setting means 14 sets, as a movement direction, a direction in which the center of gravity of the femur 57 is away from the specified surface 13B along a perpendicular to the specified surface 13B. The setting means 14 sets a movement amount of $d_{57}$. Further, the setting means 14 sets rotation in predetermined rotation direction Rd by rotation amount Ra. In the present embodiment, the predetermined rotation direction Rd is a direction with respect to a rotation axis, as an axis, that includes the center of gravity of a structure to be separated and is parallel to the specified surface, and the predetermined rotation direction Rd displays a specified-surface-side boundary surface on the display screen. Specifically, the predetermined direction Rd is calculated by detecting a voxel the distance of which to the specified surface is the shortest among voxels constituting the structure to be separated, and by calculating a direction in which the voxel the distance of which to the specified surface is the shortest is displayed on the front side of the display screen. Further, the predetermined rotation amount Ra is 90 degrees.

Here, the setting means 14 sets rotation in predetermined rotation direction Rd by rotation amount Ra. The predetermined rotation direction Rd is a direction with respect to a rotation axis, as an axis, that includes the center of gravity of the femur 57, as a structure to be separated, and is parallel to the specified surface 13B, and the predetermined rotation direction Rd displays a specified-surface-side boundary surface 571 on the display screen.

Next, with respect to the cervical bone 58, the setting means 14 sets a contour 581 of the cervical bone 58 as a boundary surface 13B. Further, the setting means 14 sets, as a movement direction, a direction in which the center of gravity of the cervical bone 58 is away from the specified surface 13B along a perpendicular to the specified surface 13B. The setting means 14 sets a movement amount of $d_{56}$. Further, the setting means 14 sets rotation in predetermined rotation direction Rd by rotation amount Ra. The predetermined rotation direction Rd is a direction with respect to a rotation axis, as an axis, that includes the center of gravity of the cervical bone 58 and is parallel to the specified surface 13B, and the predetermined rotation direction Rd displays a specified-surface-side boundary surface 581 on the display screen. Further, as illustrated in FIG. 21B, the separate image generation means 15 generates a separate image in such a manner that specified-surface-side boundary surfaces of the femur 57 and the cervical bone 58, respectively, are displayed on the display screen, and displays the generated separate image on the display means 16.

According to the sixth embodiment, the separation condition further determines a rotation direction and a rotation amount for displaying a rotated anatomical structure. Further, the separate image generation means 15 generates, based on the separation condition, a three-dimensional medical image obtained by separating and rotating an anatomical structure. Therefore, it is possible to rotate the anatomical structure in various directions by an arbitrary rotation amount in such a manner that a separated boundary surface is displayed on the display screen or the like, and to display the rotated anatomical structure. Hence, it is possible to easily perform separate display in a desired manner.

Further, according to the sixth embodiment of the present invention, it is possible to separate, based on a specified position, a bone to be separated at a joint part, and to rotate and display the separated bone in such a manner that the joint part between bones is easily recognizable. It is possible to easily separate and display the joint part. Therefore, doctors or the like can efficiently observe a joint of bones based on a medical purpose.

The sixth embodiment is applicable to any other kind of joint, such as plural vertebrae constituting a spine. Further, the sixth embodiment may be applied to plural anatomical structures of the same kind in a manner similar to each embodiment in the specification of the present application. Alternatively, the sixth embodiment may be applied to different kinds of plural anatomical structures, such as a bone and an organ. Further, as the method for extracting a bone, various known extraction methods are applicable in a manner similar to each embodiment in the specification of the present application.

Figure 25:
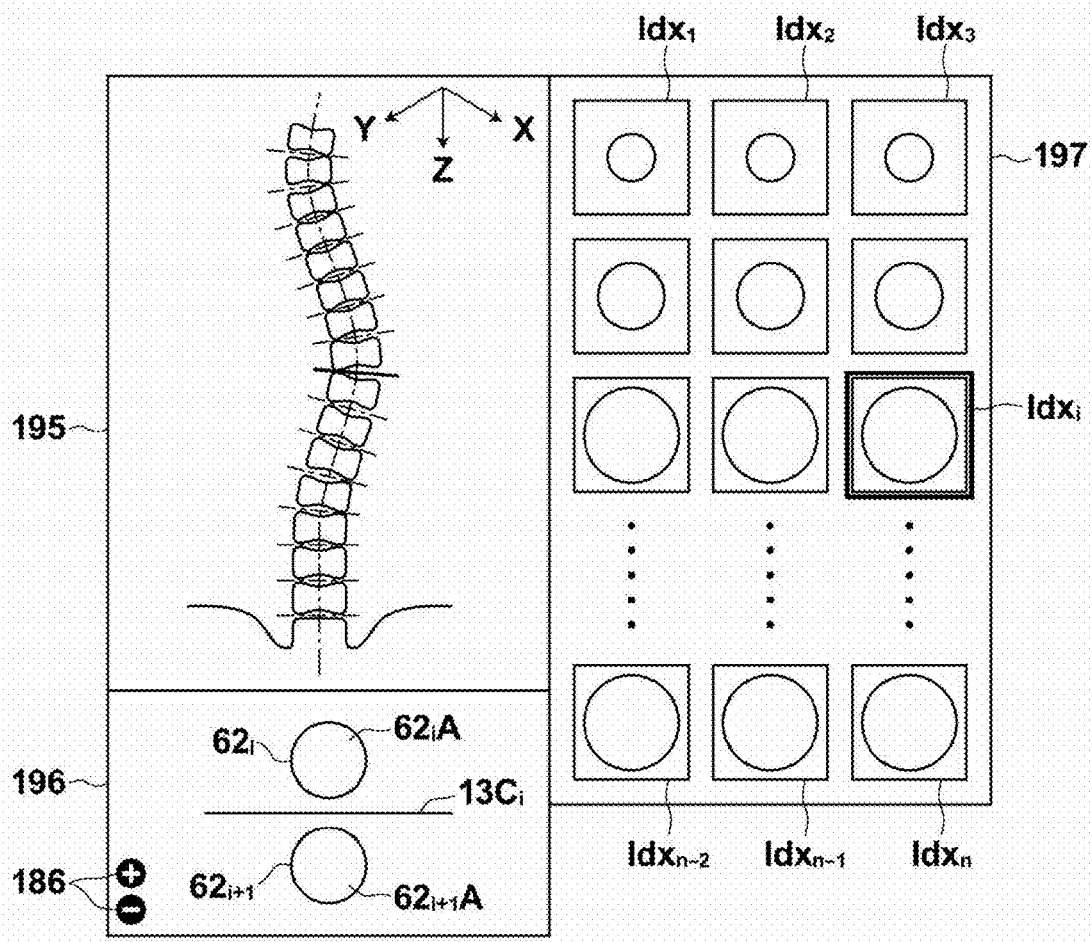
FIG. 25 an image diagram for explaining a method for specifying a specified position according to the seventh embodiment.
Figure 26:
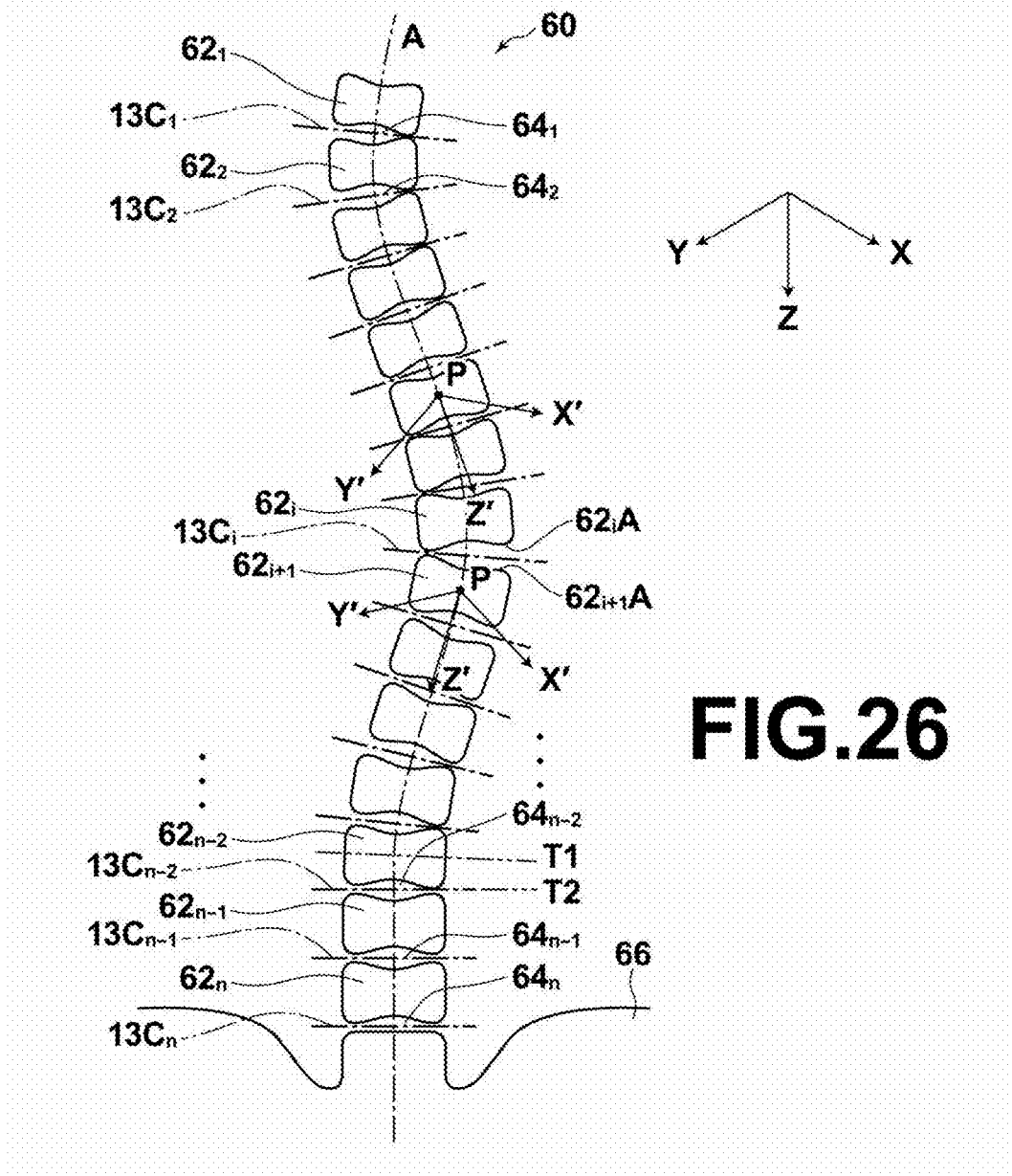
FIG. 26 an image diagram for explaining a method for extracting a vertebra according to the seventh embodiment.

With reference to FIGS. 23 through 26, a seventh embodiment of the present invention will be described by using a vertebra of a human body, as an example. FIG. 23 is a schematic diagram illustrating the configuration of an image diagnosis support apparatus according the seventh embodiment. FIG. 24 is a schematic diagram illustrating the configuration of a vertebra extraction means 19 in the image diagnosis support apparatus according to the seventh embodiment. FIG. 25 is an image diagram for explaining a method for specifying a position according to the seventh embodiment. FIG. 26 is an image diagram for explaining a method for extracting a vertebra in the seventh embodiment. FIG. 26 is a schematic diagram illustrating a sagittal image showing arrangement of each vertebra.

As illustrated in FIG. 26, a vertebral body group 60 is composed of 15 vertebrae 62, each having a substantially hollow-cylinder-shaped cortex. The vertebrae 62 are arranged in such a manner to form an S-shaped curve with respect to the body axis (Z-axis) direction. In other words, the vertebrae 62 are arranged along S-shaped center line A (hereinafter, a coordinate axis along the center line A will be referred to as "Z'-axis"). Further, an intervertebral disk 64 is present between the vertebrae 62 that are adjacent to each other. For the purpose of explanation, in FIG. 26, illustration of the intervertebral disk 64 by line drawing is omitted, and the intervertebral disk 64 is represented as a space between the vertebrae 62.

Further, a number is attached to the end of each of the reference signs 62, 64 to distinguish the vertebrae 62 and the intervertebral disks 64. Specifically, the vertebrae are $62_1$-$62_n$, and the intervertebral disks are $64_1$-$64_n$ sequentially from the top. Further, the lower surface side of the lowest intervertebral disk $64_n$ is connected to the pelves 66.

The seventh embodiment differs from the image diagnosis apparatus according to the first embodiment in that the specifying means 13 specifies a specified position by specifying a predetermined tomographic image of plural tomographic images constituting a three-dimensional medical image instead of specifying a position in the three-dimensional medical image, and that a vertebra extraction means 19 is provided in the seventh embodiment. Next, features different from the first embodiment will be mainly described, and descriptions about the same features as the first embodiment will be omitted.

The vertebra extraction means 19 mainly includes a CPU and a memory. The vertebra extraction means 19 obtains three-dimensional medical image V including a vertebra of a patient from the three-dimensional medical image data storage means 12, and extracts a vertebra 62 from the obtained three-dimensional medical image V, and stores information for identifying the extracted vertebra 62 in the structure information storage means 11. As a method for extracting a vertebra in the present embodiment, a method disclosed in Japanese Patent Application No. 2009-270837, filed by the applicant of the present application, is adopted. Such a method will be described later in detail. Further, the present invention is not limited to the present embodiment. Various known methods are adoptable as long as the methods can extract a vertebra.

In the seventh embodiment, first, the vertebra extraction means 19 extracts, from a three-dimensional medical image including vertebrae, plural vertebrae 62, vertebra center line A, and intervertebral 64. Further, the vertebra extraction means 19 stores information for identifying the vertebrae 62, the vertebra center line A, and the intervertebral 64 in the structure information storage means 11.

Next, as illustrated in FIG. 26, the specifying means 13 obtains information for identifying a vertebra $62_i$, the vertebra center line A, and an intervertebral 64 from the structure information storage means 11. The specifying means 13 sets n number of specified surfaces $13C_i$, along the extracted center axis, in the intervertebral 64 between the vertebra $62_i$ and the vertebra $62_{i+1}$, which are adjacent to each other. The specifying means 13 repeats setting of the specified surface $13C_i$ n number of times, and n is the number of intervertebral $64_i$ (0<i≤n is a natural number). The n number of cross sections $13C_1$, $13C_2$, ..., $13C_{n-1}$, $13C_n$ are cross sections orthogonal to the vertebra center line A, and located along the vertebra center line A. Each of the cross sections is stored in the structure information storage means 11, as a specified surface $13C_i$ (0<i≤n) for each of plural vertebrae constituting a spine. In the present embodiment, a user can arbitrarily set a position in an anatomical structure at which a specified position is set, the shape (a surface, a line, a point, or a three-dimensional object) of the specified position, and the number of specified positions. It is assumed that a user has set, in advance, specified surfaces $13C_i$ in n intervertebral $64_i$ along the vertebra enter line A. Further, the setting means 14 extracts, based on the separation condition table 172 illustrated in FIG. 22, a vertebra $62_i$ and a vertebra $62_{i+1}$, which are adjacent to each other with a specified surface $13C_i$ therebetween, as structures to be cut that are present in predetermined range d from the specified surface $13C_i$. With respect to the vertebra $62_i$, the setting means 14 sets a contour of the vertebra 62; as a boundary surface. Further, the setting means 14 sets, as a movement direction, a direction in which the center of gravity of the vertebra $62_i$ moves away along a perpendicular to the specified surface $C_i$ from the specified surface $13C_i$, and a movement amount $d_{62}$. Further, the setting means 14 sets a rotation direction Rd and a rotation amount Ra that are the same rotation condition as the sixth embodiment. Specifically, the setting means 14 sets rotation with respect to a rotation axis, as an axis, that includes the center of gravity of the vertebra 62, and is parallel to the specified surface $13C_i$. Further, the setting means 14 sets a rotation amount Ra in a predetermined direction Rd in such a manner that a specified-surface-side boundary surface $62_i$A is displayed on the display screen. Further, with respect to the vertebra $62_{i+1}$, the setting means 14 sets a contour of the vertebra $62_{i+1}$ as a boundary surface. Further, the setting means 14 sets, as a movement direction, a direction in which the center of gravity of the vertebra $62_{i+1}$ moves away along a perpendicular to the specified surface $C_i$ from the specified surface $13C_i$, and a movement amount $d_{62}$. Further, the setting means 14 sets a predetermined rotation direction Rd and a predetermined rotation amount Ra. Specifically, the setting means 14 sets rotation with respect to a rotation axis, as an axis, that includes the center of gravity of the vertebra $62_{i+1}$ and is parallel to the specified surface $13C_i$. Further, the setting means 14 sets a rotation amount Ra in a predetermined direction Rd in such a manner that a specified-surface-side boundary surface $62_{i+1}A$ is displayed on the display screen.

Further, the separate image generation means 15 generates a separate image, as illustrated in an area 196 of FIG. 25, in which boundary surfaces $62_iA$ and $62_{i+1}A$ of the vertebrae $62_i$ and $62_{i+1}$, respectively, are displayed in the display screen. Further, the separate image generation means 15 stores the generated image in a hard disk 105.

In the present embodiment, the setting means 14 extracts structures $62_i$, $62_{i+1}$ to be cut for each of n number of specified surfaces $13C_i$ illustrated in FIG. 26. Further, the setting means 14 sets a boundary surface and a separation condition based on the boundary surface. The separate image generation means 15 generates, based on each set boundary surface and each separation condition, n number of separate images for n number of specified surfaces $13C_i$, respectively. Further, the separate image generation means 15 stores the generated separate images in the hard disk 105.

Further, the separate image generation means 15 generates index image $Idx_i$, which is a tomographic image of each of n number of specified surfaces $13C_i$, together with a separate image corresponding to each of the n number of specified surfaces $13C_i$. The separate image generation means 15 stores the index image $Idx_i$ in the hard disk 105. In the present embodiment, the index image $Idx_i$ is a reduced image of a tomographic image representing a subject at a specified surface $13C_i$ in a direction from the vertebra $62_i$ toward the vertebra $62_{i+1}$ so that plural index images are displayed as a list on the display screen.

The specifying means 13 specifies a specified position by specifying a predetermined tomographic image of plural tomographic images constituting a three-dimensional medical image, instead of specifying a specified position in the three-dimensional medical image. Specifically, the specifying means 13 detects selection of position specifying option (position specifying option by a tomographic image) of the present embodiment by a manual operation on a display screen by a user. The specifying means 13 displays n number of index images $Idx_i$ (0<i≤n) on the display means 16, as illustrated in an area 197 in FIG. 25.

An example of display on a display screen illustrated in FIG. 25 schematically illustrates a work area 195, an index image selection area 197 and a separate image display area 196, as an example of display of an image according to the present embodiment. The work area 195 displays a three-dimensional medical image representing vertebrae of a patient. The index image selection area 197 receives selection of an index image $Idx_i$ by a user for specifying a specified position. The separate image display area 196 displays a separate image corresponding to a specified surface that has been specified.

The specifying means 13 detects an index image $Idx_i$ that has been selected by a manual operation by a user at an input device. The specifying means 13 loads an image to be separated at a specified surface $13C_i$ corresponding to the index image from the hard disk 105 into the memory. Further, the specifying means 13 displays the image in the separate image display area 196, as illustrated in FIG. 25.

According to the seventh embodiment, the specifying means 13 specifies a specified position by specifying a predetermined tomographic image $Idx_i$ of plural tomographic images constituting a three-dimensional medical image, instead of specifying a specified position in the three-dimensional medical image. Therefore, it is possible to easily specify a desired specified position $13C_i$ based on the position of the desired tomographic image $Idx_i$.

Further, in the seventh embodiment, the setting means 14 automatically sets plural specified surfaces $13C_i$, and the separate image generation means 15 automatically generates a tomographic image corresponding to a specified position. Since it is possible to specify a desired tomographic image $Idx_i$ of plural tomographic images, even if a user is not accustomed to an operation of specifying a specified position, the user can easily specify a specified surface. Therefore, it is possible to support an improvement in the accuracy and the efficiency of image diagnosis.

Here, setting of positions for generating plural tomographic images may be manually performed by a user. For example, a user may click an arbitrary position on a vertebra center line by a mouse or the like. Further, a clicked position may be detected, and a tomographic image at the position may be used as an index image $Idx_i$ (0<i≤k, k is the number of specified positions that have been specified by a user). Plural tomographic images constituting a three-dimensional medical image in the seventh embodiment may be tomographic images obtained by tomography, such as CT. Alternatively, the plural tomographic images may be tomographic images at arbitrary cross sections obtained by an MPR method or the like.

Plural tomographic images in the seventh embodiment are tomographic images of vertebrae along the vertebra center axis A. Therefore, it is possible to efficiently and easily observe, especially, a disease of an intervertebral disk, and that is useful.

In the seventh embodiment, a list of plural index images $Idx_i$ (0<i≤n), representing tomographic images of plural specified surfaces respectively, is displayed. Further, a specified position is specified by specifying a predetermined tomographic image of the index images $Idx_i$, displayed as a list. Therefore, a user can easily specify a specified surface, recognizing a position at which the user wants to perform separate display. Hence, it is possible to support an improvement in the accuracy and the efficiency of image diagnosis. The present invention is not limited to the present embodiment. When a list of plural tomographic images is displayed, when the list is displayed, only a part of n number of index images $Idx_i$ (0<i≤n) may be displayed.

Further, as a modified example of the specifying means 13 of the seventh embodiment of the present invention, a plus minus button 186 for changing a specified surface $13C_i$ may be further provided in the area 196, as illustrated in FIG. 25. A change in the specified position by a user may be received by the plus minus buttons 186. For example, in a state in which a separate image corresponding to a specified surface $13C_i$ is displayed in the area 196 by specifying an index image $Idx_i$ as described above, the specifying means 13 detects the number h of times of click of a plus button by a user. Then, the specifying means 13 displays a separate image corresponding to a specified surface $13C_{i+h}$, which has been shifted by the number h of times of click, on the display means 16. Similarly, in a state in which a separate image corresponding to a specified surface $13C_i$ is displayed in the area 196, the specifying means 13 detects the number h of times of click of a minus button by a user. Then, the specifying means 13 displays a separate image corresponding to a specified surface $13C_{i-h}$, which has been shifted by the number h of times of click, on the display means 16. Accordingly, it is possible to specify consecutive tomographic images in the order of positions along the vertebra center axis. A user can easily specify a specified surface at which the user wants to perform separate display, while gradually changing a physical position.

Therefore, it is possible to support an improvement in the accuracy and the efficiency of image diagnosis. Further, after a specified tomographic image is specified by displaying a list of index images $Idx_i$, fine adjustment of the specified position is easily performed.

The method for specifying a specified position according to the seventh embodiment may be any method as long as a tomographic image can be specified. In addition to displaying a list of plural index images, as in the aforementioned modified example, the specifying means 13 may display index images $Idx_i$ ($0<i\leq n$) of vertebrae orthogonal to the vertebra center axis A along the vertebra center axis A by sequentially switching them from each other. Alternatively, in the seventh embodiment, the specifying means 13 may display an index image $Idx_i$ of a vertebra orthogonal to the vertebra center axis A in the area 197, instead of displaying a list of plural index images. Further, the specifying means 13 may display a vertical scroll bar at the right edge of the area 197, and display index images $Idex_i$ along the vertebra center axis A based on a scroll operation by a user within the range of $0<i\leq n$ by sequentially switching the index images from each other. In this case, the position of a knob (handle) of a vertical scroll bar corresponds to the position of a specified surface $13C_i$. The highest-end scroll position of the vertical scroll bar corresponds to the position of a specified surface $13C_i$. The lowest-end scroll position of the vertical scroll bar corresponds to the position of a specified surface $13C_n$.

Next, vertebra extraction processing in the present embodiment will be described in detail. As illustrated in FIG. 24, the vertebra extraction means 19 includes an image generation unit 81, a vertebra center line detection unit 82, a first feature value calculation unit 83, a second feature value calculation unit 84, a third feature value calculation unit 85, and a vertebra position estimation unit 86. The image generation unit 81 obtains a three-dimensional medical image from the three-dimensional medical image data storage means 12, and generates, along each vertebra center axis of a subject, plural tomographic images orthogonal to the center axis. The vertebra center line detection unit 82 detects a vertebra center line based on plural tomographic images. The first feature value calculation unit 83 calculates, based on a tomographic image, a first feature value representing a profile in a direction orthogonal to a center axis for each point on the center axis. The second feature value calculation unit 84 calculates, based on a tomographic image, a second feature value representing a profile in a direction of the center axis for each point on the center axis. The third feature value calculation unit 85 calculates, based on the calculated first feature value and second feature value, a third feature value representing the regularity of arrangement of each vertebra for each point on the center axis. The vertebra position estimation unit 86 estimates the position of each vertebra on the center axis based on the third feature value calculation unit 85.

The image generation unit 81 generates, based on a three-dimensional medical image including a vertebral body obtained by the image generation unit 81, plural first tomographic images (for example, axial tomographic images) along a predetermined axial direction (for example, the direction of a body axis). The image generation unit 81 records the generated plural first tomographic images in the memory 109. Further, the image generation unit 81 generates, based on the obtained three-dimensional medical image, plural second tomographic images along the center axis of each vertebra. The image generation unit 81 may appropriately change the range of the space region of an image to be generated.

The vertebra center line detection unit 82 detects the center line of each vertebra included in each of the plural first tomographic images generated by the image generation unit 81.

When the center line A of each vertebra 62 is directly detected by using the plural first tomographic images, extremely high image processing techniques are required. Therefore, various detection techniques focusing on the structural characteristic of the vertebral body may be adopted. For example, the center line of the spinal cord, which is not illustrated, may be obtained in advance, because detection of the center line of the spinal cord by image processing is relatively easy. Then, it is possible to accurately detect the center line A of each vertebra 62 based on a relative positional relationship between the spinal cord and the vertebra 62 (for detail, please refer to Japanese Unexamined Patent Publication No. 2009-207886).

As a method for detecting the center line of the spinal cord, a template matching method or a demarcation method may be adopted. Alternatively, a learning method based on Adaboost, which is a method for generating an integrated learning machine, may be used.

The first feature value calculation unit 83 calculates a first feature value representing the sharpness of the shape of a cross section orthogonal to the direction of Z'-axis with respect to vertebra 62 (please refer to FIG. 26). As the first feature value, for example, a feature value extracting a ring-shaped pattern with respect to a predetermined point P on the Z'-axis, as a center, is used. An eigenvalue analysis method of Hessian matrix, which will be described later, is used to calculate this feature value. The first feature value calculation unit 83 records the calculated first feature value in the memory 109.

The second feature value calculation unit 84 calculates a second feature value representing the sharpness of the shape of a cross section parallel to the direction of Z'-axis with respect to vertebra 62 (please refer to FIG. 26). As the second feature value, for example, a feature value extracting a disk-shaped pattern extending in the direction of the Z'-axis with respect to a predetermined point P on the Z'-axis, as a center, is used. An eigenvalue analysis method of Hessian matrix, which will be described later, is used to calculate this feature value. The second feature value calculation unit 84 records the calculated second feature value in the memory 109.

The third feature value calculation unit 85 calculates a third feature value representing the regularity of arrangement of each vertebra 62. As the third feature value, for example, a weighted sum of the first and second feature values is used. The third feature value calculation unit 85 records the calculated third feature value in the memory 109.

The vertebra position estimation unit 86 estimates, based on the third feature value, the position of each vertebra 62 in XYZ coordinate. The vertebra position estimation unit 86 records the estimated position of each vertebra 62 in the memory 109. The vertebra position estimation unit 86 outputs the position of each vertebra 62 that has been estimated by the vertebra position estimation unit 86 to the outside. In the present embodiment, the position of each vertebra 62 is stored in the structure information storage means 11. Here, plural base positions (an end point, a center position or the like of a vertebra 62 or an intervertebral disk 64) are set in advance for the vertebrae, and a base position of each vertebra is stored.

Next, an operation of the vertebra extraction means 19 will be described with reference to a flow chart illustrated in FIG. 27.

First, the image generation unit 81 generates, based on a three-dimensional medical image including a vertebral body obtained by the image generation unit 81, X-Y tomographic images along the direction of a body axis (Z-axis), in other words, plural first tomographic images (S401).

Here, when the image generation unit 81 has obtained plural first tomographic images that are axial cross sections, the image generation unit 81 obtains the plural first tomographic images obtained by the image generation unit 81.

Next, the vertebra center line detection unit 82 detects center line A of a vertebra 62 included in each of the plural first tomographic images obtained in S401 (S402). The vertebra center line detection unit 82 detects the center line A of the vertebra 62 illustrated in FIG. 2 by using the aforementioned detection method. After then, the center line A is set as a new coordinate axis (Z'-axis).

Next, the image generation unit 81 generates, based on the three-dimensional medical image obtained in S401, X'-Y' tomographic images along the center line A (Z'-axis) detected in S402, in other words, plural second tomographic images (S403). The image generation unit 81 should generate plural second tomographic images without using all of image information about the obtained three-dimensional medical image. The image generation unit 81 should generate the plural second tomographic images by using only image information reconstructable in a partial area in the vicinity of Z'-axis including an entire region in which the vertebral body group 60 is present. Then, it is possible to reduce the usage amount of the memory 109 and the operation time by the CPU 107.

Next, the first feature value calculation unit 83 calculates a first feature value based on the plural second tomographic images obtained in S403 (S404).

The spine is composed of a cervical vertebra, a thoracic vertebra, a lumbar vertebra, a sacrum and a coccyx. Among them, the outer shape of the cervical vertebra, the thoracic vertebra and the lumbar vertebra is cylindrical. Further, the surfaces of the cervical vertebra, the thoracic vertebra and the lumbar vertebra are composed of a cortex (Cortical bone), and the insides the cervical vertebra, the thoracic vertebra and the lumbar vertebra are composed of cancellous bone (Spongy bone). Further, both ends of the cylindrical shape of a vertebral body are substantially flat. Further, an intervertebral disk is present between vertebral bodies.

Therefore, a hollow-cylinder-shaped area with high voxel values (CT values) appears, because the cortex on the surface of the vertebra forms a hollow-cylindrical shape in the body part of the vertebra excluding the two ends of the cylindrical shape of the vertebral body. The first feature value should represent this hollow-cylindrical pattern quantitatively. In the present embodiment, the hollow-cylindrical pattern is regarded as a ring-shaped pattern that appears in a tomographic image orthogonal to the vertebra center line. Further, a feature value orthogonal to a vector connecting the vertebra center line is quantified as represented by formula (1), and the value is used as the first feature value.

The first feature value is represented by the following formula (1):

[Formula1]

$$f_1(z') = \int\int_{(x',y',z')\in R} \frac{\lambda_1(x', y', z')}{|\lambda_2(x', y', z')| + |\lambda_3(x', y', z')| + \varepsilon} \quad (1)$$
$$|\vec{E_1}(x', y', z') \cdot \vec{p}| dx' dy'.$$

Here, (x', y', z') represents a position in an X'Y'Z' coordinate system. Further, domain R of integration is points on the second tomographic image, and represents the cortex region of the vertebra 62.

Further, an eigenvalue and an eigenvector in 3×3 Hessian matrix are (λ1, λ2, λ3), and (E1, E2, E3), respectively. Further, λ1≤λ2≤λ3. Vector p is a vector from point (0,0,z') on Z'-axis toward (x', y', z'), and p=(x', y', 0). Further, ε is a very small positive integer provided to prevent division by 0.

Figure 28A:
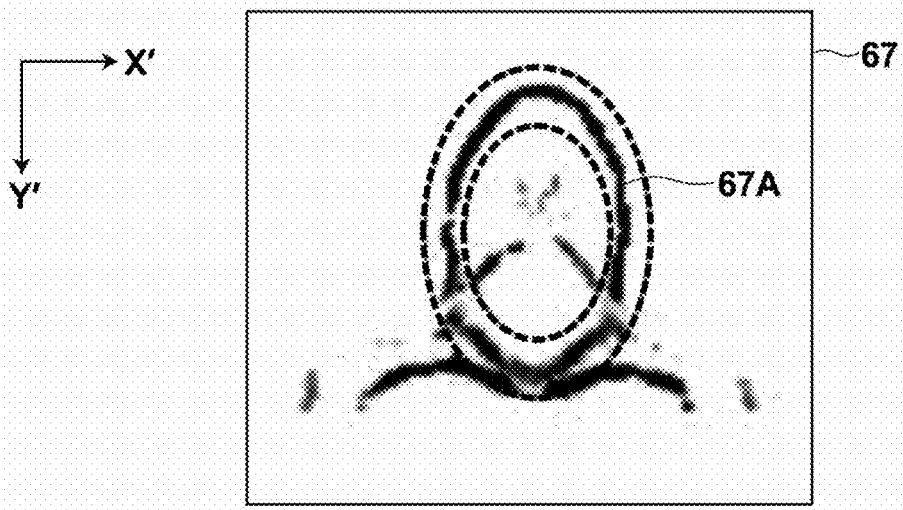
FIG. 28A a schematic diagram illustrating two-dimensional distribution of first feature values (integrand) at each cross-section position according to the seventh embodiment (vertebra center position)
Figure 28B:
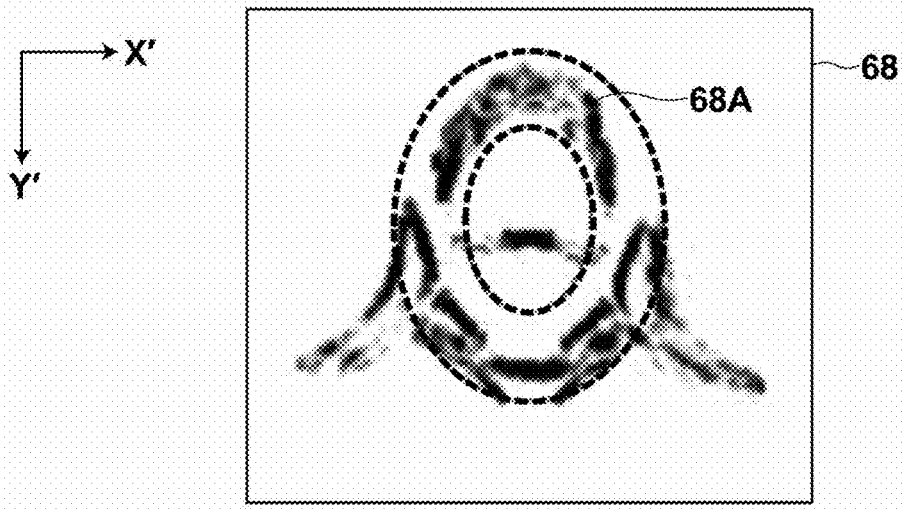
FIG. 28B a schematic diagram illustrating two-dimensional distribution of first feature values (integrand) at each cross-section position according to the seventh embodiment (intervertebral position)

FIGS. 28A and 28B are schematic diagrams illustrating two-dimensional distribution of first feature values (integrand) at each cross-sectional position. Specifically, numerical values of the first feature values (integrand) in the second tomographic image are visualized as the grayscale of an image. The image is displayed in such a manner that the density level is high at a position in which the first feature value is large, and that the density level is low at a position in which the first feature value is small.

FIG. 28A is a schematic diagram illustrating a visible image 67 representing calculated values of the first feature value at cross section position T1 (please refer to FIG. 26). Since the cross section position T1 is a middle position of a vertebra 62, a second tomographic image at the cross section position T1 includes a cross-sectional shape of the cortex of the vertebra 62. Therefore, a ring-shaped black pattern 67A sharply appears in the visible image 67. Consequently, the first feature value that is the sum of integrand in domain R of integration becomes large. Here, the domain R of integration represents a surface (cortex) region of a vertebra.

Meanwhile, FIG. 28B is a schematic diagram illustrating a visible image 68 representing calculated values of the first feature value at cross section position T2 (please refer to FIG. 2). Since the cross section position T2 is a position in an intervertebral disk $64_{n-2}$, a second tomographic image at the cross section position T2 does not include a cross-sectional shape of the cortex of the vertebra 62. Instead, the second tomographic image includes a peripheral region of the intervertebral disk $64_{n-2}$. Therefore, a ring-shaped low-gray level pattern 68A slightly appears in the visible image 68. Consequently, the first feature value that is the sum of integrand in domain R of integration becomes small.

As another example of calculation of the first feature value, for example, a Laplacian filter (second order differential filter) for detecting edge intensity may be used. Alternatively, a Laplacian of Gaussian filter (Laplacian Of Gaussian Filter; hereinafter, referred to as "LOG filter") may be used. The LOG filter applies Laplacian after a local area is smoothed by performing weighting of Gauss distribution on voxels in the local area, and detects its zero crossing, as an edge.

Next, the second feature value calculation unit 84 calculates a second feature value based on plural second tomographic images obtained in S403 (S405).

With respect to the second feature value, a disk-shaped (disk-shaped) area with low voxel values (CT values) representing an intervertebral disk appears between vertebrae, because a vertebra has a cylindrical shape with two disk-shaped ends, and the intervertebral disk is present between vertebral bodies. The pattern appears as a low voxel value area, because the voxel value of the intervertebral disk is lower than the voxel value of a vertebra. The second feature value should represent this disk-shaped pattern quantitatively.

In the present embodiment, a pattern on a disk that appears in the vicinity of a vertebra center line of a tomographic image orthogonal to the vertebra center line is quantified, along each vertebra center line, as a feature value of a cross section perpendicular to Z-axis in the vicinity of the vertebra center line, as represented by formula (2), and the feature value is used as the second feature value.

The second feature value is represented by the following formula (2):

[Formula 2]

$$f_2(z') = \iint_{(x',y',z') \in C} \frac{\lambda_1(x', y', z')}{|\lambda_2(x', y', z')| + |\lambda_3(x', y', z')| + \varepsilon} |\vec{E_1}(x', y', z') \cdot \vec{e_z}| dx' dy'. \quad (2)$$

Here, (x', y', z') represents a position in an X'Y'Z' coordinate system. Further, domain C of integration represents a region in the vicinity of the center line A (Z'-axis).

In a manner similar to the formula (1), an eigenvalue and an eigenvector in 3×3 Hessian matrix are (λ1, λ2, λ3), and (E1, E2,E3), respectively. Further, λ1≤λ2≤λ3. Vector ez is a unit vector (0,0,1) on Z'-axis. Further, ε is a very small positive integer provided to prevent division by 0.

Figure 29:
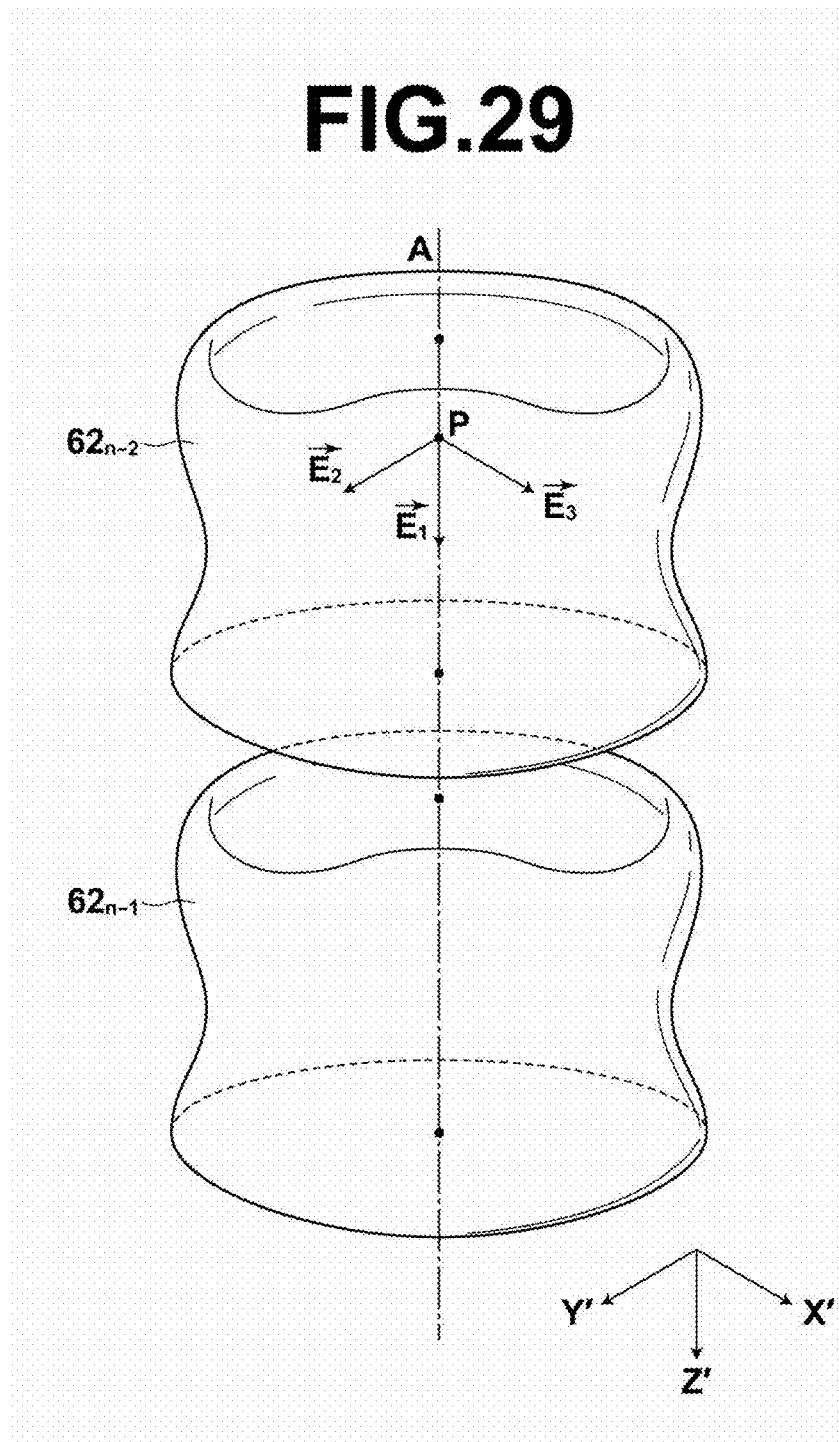
FIG. 29 a schematic diagram illustrating a corresponding relationship between the three-dimensional shape of a vertebral body and an eigenvector of a Hessian matrix at an internal point of the three-dimensional shape according to the seventh embodiment.

FIG. 29 is a schematic diagram illustrating a corresponding relationship between the three-dimensional shape of vertebra $62_{n-1}$ and eigenvectors E1-E3 of Hessian matrix at internal point P in the three-dimensional shape. The eigenvector E1 corresponding to smallest eigenvalue λ1 of Hessian matrix is directed in a direction (the direction of Z'-axis) in which the vertebra $62_{n-2}$ extends. Therefore, as understood from the shape of the integrand represented by the formula (2), a flat shape without density gradient with respect to point P, especially, only vector components in the direction of Z'-axis are extracted as the second feature value. In other words, the second feature value is a feature value extracting a disk-shaped pattern extending in the direction of Z'-axis.

Next, the third feature value calculation unit 85 calculates a third feature value based on the first feature value calculated in S404 and the second feature value calculated in S405 (S406).

The first feature value clearly represents the body part on a cylindrical shape of the vertebral body. The second strong-point value clearly represents the intervertebral disk portion. Therefore, if the two values are used in combination, it is possible to more clearly represent the repetition frequency of the vertebral body and the intervertebral disk. Further, the signs of the two feature values of the first feature value and the second feature value are opposite to each other. Therefore, when they are used in combination, it is possible to more remarkably represent its frequency characteristic.

The third feature value is represented by the following formula (3):

[Formula 3]

$$f_3(z') = f_1(z') + \alpha \max_{\sigma \in [\sigma_0, \sigma_1]} \left[ \frac{d^2 G(z', \sigma)}{dz'^2} \otimes f_2(z') \right]. \quad (3)$$

Here, α is an arbitrary weighting coefficient, and G(z', σ) is a Gauss function using σ as standard deviation.

FIG. 30 is a diagram illustrating profiles of the first through third feature values in the direction of Z'-axis.

In FIG. 30, the profiles of the first and second feature values in the direction of Z'-axis are illustrated in section A. The first feature value (solid line) and the second feature value (broken line) exhibit the maximum values at the center position of a vertebra 62 (cross section position T1 illustrated in FIG. 26), and they exhibit the minimum values at the position of an intervertebral disk 64 (cross section position T2 illustrated in FIG. 26).

In FIG. 30, the profile of the second feature value after application of a LOG filter is illustrated in section B. A part of the profile of the second feature value (please refer to the section A of FIG. 30) in which the second order differential is 0 is extracted. Therefore, the profile illustrated in section B of FIG. 30 has a periodic function shape. This profile exhibits the maximum value at the center position of a vertebra 62 (cross section position T1 illustrated in FIG. 26), and it exhibits the minimum value at the position of an intervertebral disk 64 (cross section position T2 illustrated in FIG. 26).

Meanwhile, the shape of a profile illustrated in FIG. 6B changes based on the value of σ in Gauss function (z', σ). In the present embodiment, the value of o is selected so that the value of the profile becomes the highest in a predetermined range of σ0 to σ1.

In FIG. 30, the profile of a third feature value in the direction of Z'-axis is illustrated in section C. The third feature value is a value obtained by adding first feature value f1 (z') and a feature value obtained by applying a LOG filter to second feature value together.

Accordingly, third feature value f3 (z') representing the regularity of the arrangement of each vertebra 62 is generated.

Next, the position of each vertebra 62 on Z'-axis is estimated (S407). The third feature value exhibits the maximum value at the center position of a vertebra 62 (cross section position T1 illustrated in FIG. 26), and it exhibits the minimum value at the position of an intervertebral disk 64 (cross section position T2 illustrated in FIG. 26). Therefore, it is possible to estimate the position of each vertebra 62 on the Z'-axis.

Finally, the position of each vertebra 62 on Z-axis is transformed (S408). The vertebra position estimation unit 86 transforms the position of each vertebra 62 on the Z'-axis that has been estimated in S408 to a position in XYZ coordinate. Since the positional relationship between point P on the Z'-axis and the XYZ coordinate is known, such coordinate transformation is easy. Accordingly, the vertebra extraction means 19 extracts the position of each vertebra 62.

In the seventh embodiment, it is possible to accurately extract the position of each vertebra along the vertebra center line by adopting the aforementioned vertebra extraction method. Therefore, it is possible to accurately specify an intervertebral position along the vertebra center line and to accurately perform separate display at a boundary surface. All of the described embodiments may be applied to other embodiments without departing from the gist of the invention.

The invention claimed is:

1. An image diagnosis support apparatus comprising:
   a three-dimensional medical image data storage unit that stores three-dimensional medical image data of a subject;
   a display unit that displays a three-dimensional medical image based on the stored three-dimensional medical image data;
   a structure information storage unit that stores a plurality of anatomical structures included in the three-dimensional medical image data;
   a specifying unit that specifies, in the three-dimensional medical image displayed by the display unit, at least one specified position and, if necessary, a cutting surface for separating the plurality of anatomical structures included in the three-dimensional medical image;
   a separation condition storage unit that stores a separation condition for each anatomical structure of the subject to determine, based on the specified position specified by the specifying unit, a boundary surface and, if necessary, a cutting surface for separately displaying the plurality of anatomical structures;

a setting unit that extracts, as structures to be separated, the plurality of anatomical structures present within a predetermined range from the specified position that has been specified, and that sets, based on the separation condition, the boundary surface corresponding to the extracted structures to be separated and the specified position that has been specified, and that sets the cutting surface if necessary; and a separate image generation unit that generates, based on the boundary surface and, if necessary, the cutting surface as well as based on the three-dimensional medical image data, a three-dimensional medical image in which the structures to be separated are separated by the boundary surface and, if necessary, by the cutting surface, and that makes the display unit display the three-dimensional medical image.

2. An image diagnosis support apparatus, as defined in claim 1, wherein the separation condition determines, as the boundary surface, a contour of the structure to be separated.

3. An image diagnosis support apparatus, as defined in claim 1, wherein the separation condition determines, as the boundary surface, a contour of a predetermined anatomical structure of the plurality of anatomical structures when the predetermined anatomical structure constitutes a part of another anatomical structure.

4. An image diagnosis support apparatus, as defined in claim 1, wherein the separation condition determines the boundary surface in such a manner that only a part of the anatomical structures is separately displayed.

5. An image diagnosis support apparatus, as defined in claim 1, further comprising:

a separation condition change unit that receives change of the separation condition in display of the three-dimensional medical image displayed by the display unit, and that changes the separation condition stored in the separation condition storage unit.

6. An image diagnosis support apparatus, as defined in claim 1, wherein the specifying unit specifies the specified position in a predetermined region of the three-dimensional medical image by limiting the predetermined region.

7. An image diagnosis support apparatus, as defined in claim 3, wherein the other anatomical structure is a liver, and wherein the predetermined anatomical structure is blood vessels constituting the liver.

8. An image diagnosis support apparatus, as defined in claim 2, wherein the anatomical structures are bones.

9. An image diagnosis support apparatus, as defined in claim 1, wherein the separation condition further determines a rotation direction and a rotation amount for rotating and displaying the anatomical structures, and wherein the separate image generation unit generates a three-dimensional medical image in which the anatomical structures are separated and rotated based on the separation condition.

10. An image diagnosis support apparatus, as defined in claim 1, wherein the specifying unit specifies the specified position by specifying a predetermined tomographic image of a plurality of tomographic images constituting the three-dimensional medical image instead of specifying a position in the three-dimensional medical image.

11. An image diagnosis support method comprising:

displaying a three-dimensional medical image based on three-dimensional medical image data of a subject stored in a three-dimensional medical image data storage unit that stores the three-dimensional medical image data;

specifying, in the three-dimensional medical image displayed by a display unit, at least one specified position and, if necessary, a cutting surface for separating a plurality of anatomical structures included in the three-dimensional medical image;

extracting, as structures to be separated, the plurality of anatomical structures present within a predetermined range from the specified position that has been specified by referring to a structure information storage unit that stores the plurality of anatomical structures included in the three-dimensional medical image data and a separation condition storage unit that stores a separation condition for each anatomical structure of the subject to determine, based on the specified position that has been specified, a boundary surface and, if necessary, a cutting surface for separately displaying the plurality of anatomical structures, and setting, based on the separation condition, the boundary surface corresponding to the extracted structures to be separated and the specified position that has been specified and, if necessary, setting the cutting surface; and generating, based on the boundary surface and, if necessary, the cutting surface as well as based on the three-dimensional medical image data, a three-dimensional medical image in which the structures to be separated are separated by the boundary surface and, if necessary, by the cutting surface, and making the display unit display the three-dimensional medical image.

12. A computer-readable non-transitory recording medium having stored therein an image diagnosis support program for causing a computer to function as:

a three-dimensional medical image data storage unit that stores three-dimensional medical image data of a subject;

a display unit that displays a three-dimensional medical image based on the stored three-dimensional medical image data;

a structure information storage unit that stores a plurality of anatomical structures included in the three-dimensional medical image data;

a specifying unit that specifies, in the three-dimensional medical image displayed by the display unit, at least one specified position and, if necessary, a cutting surface for separating the plurality of anatomical structures included in the three-dimensional medical image;

a separation condition storage unit that stores a separation condition for each anatomical structure of the subject to determine, based on the specified position specified by the specifying unit, a boundary surface and, if necessary, a cutting surface for separately displaying the plurality of anatomical structures;

a setting unit that extracts, as structures to be separated, the plurality of anatomical structures present within a predetermined range from the specified position that has been specified, and that sets, based on the separation condition, the boundary surface corresponding to the extracted structures to be separated and the specified position that has been specified, and that sets the cutting surface if necessary; and a separate image generation unit that generates, based on the boundary surface and, if necessary, the cutting surface as well as based on the three-dimensional medical image data, a three-dimensional medical image in which the structures to be separated are separated by the boundary surface and, if necessary, by the cutting surface, and that makes the display unit display the three-dimensional medical image.

* * * * *